(12) United States Patent
Zhao

(10) Patent No.: US 11,986,808 B2
(45) Date of Patent: May 21, 2024

(54) SYNTHETIC CATALYSTS FOR CARBOHYDRATE PROCESSING

(71) Applicant: Iowa State University Research Foundation, Inc., Ames, IA (US)

(72) Inventor: Yan Zhao, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 400 days.

(21) Appl. No.: 17/368,257

(22) Filed: Jul. 6, 2021

(65) Prior Publication Data

US 2022/0016612 A1 Jan. 20, 2022

Related U.S. Application Data

(60) Provisional application No. 63/048,370, filed on Jul. 6, 2020.

(51) Int. Cl.
| | |
|---|---|
| *B01J 31/00* | (2006.01) |
| *B01J 31/06* | (2006.01) |
| *B01J 35/23* | (2024.01) |
| *B01J 37/04* | (2006.01) |
| *C13K 1/02* | (2006.01) |

(52) U.S. Cl.
CPC ............ *B01J 31/067* (2013.01); *B01J 35/23* (2024.01); *B01J 37/04* (2013.01); *C13K 1/02* (2013.01)

(58) Field of Classification Search
None
See application file for complete search history.

(56) References Cited

U.S. PATENT DOCUMENTS

| 8,241,575 B2 * | 8/2012 | Murray | G01N 21/78 |
| | | | 422/50 |
| 2012/0136180 A1 * | 5/2012 | Roth | B01J 21/08 |
| | | | 502/232 |

OTHER PUBLICATIONS

Aden, Andy, et al., "Lignocellulosic Biomass to Ethanol Process Design and Economics Utilizing Co-Current Dilute Acid Prehydrolysis and Enzymatic Hydrolysis for Corn Stover", NREL, National Renewable Energy Laboratory, Department of Energy, Golden, CO, (May 30, 2002), 153 pgs.

Almeida, Joao R. M, et al., "Metabolic effects of furaldehydes and impacts on biotechnological processes", Appl. Microbiol. Biotechnol., 82, (2009), 625-638.

Arifuzzaman, M. D., et al., "Artificial Zinc Enzymes with Fine-Tuned Catalytic Active Sites for Highly Selective Hydrolysis of Activated Esters", ACS Catal., 8, (2018), 8151-8161 (8 pgs.).

Awino, J. K., et al., "Protein-Mimetic, Molecularly Imprinted Nanoparticles for Selective Binding of Bile Salt Derivatives in Water", J. Am. Chem. Soc., 135, (2013), 12552-12555.

Awino, J. K., et al., "Sequence-Selective Binding of Oligopeptides in Water through Hydrophobic Coding", J. Am. Chem. Soc., 139, (2017), 2188-2191.

Bérubé, Marie, et al., "Benzoboroxoles as Efficient Glycopyranoside-Binding Agents in Physiological Conditions: Structure and Selectivity of Complex", J. Org. Chem., 73(17), (2008), 6471-6479.

(Continued)

*Primary Examiner* — Stefanie J Cohen
(74) *Attorney, Agent, or Firm* — Schwegman Lundberg & Woessner, P.A.

(57) ABSTRACT

The disclosure relates to molecularly-imprinted cross-linked micelles that can selectively hydrolyze carbohydrates.

20 Claims, 34 Drawing Sheets

(56) References Cited

OTHER PUBLICATIONS

Binder, Joseph B., et al., "Fermentable sugars by chemical hydrolysis of biomass", Proc. Natl. Acad. Sci. USA, 107, (20110), 4516-4521.

Brogen, Alex P. S., et al., "Non-aqueous homogenous biocatalytic conversion of polysaccharides in ionic liquids using chemically modified glucosidase", Nat. Chem. 10, (2018), 859-865.

Chen, Kaiqian, et al., "Effects of nano-confinement and conformational mobility on molecular imprinting of cross-linked micelles", Org. Biomol. Chem., 17(37), (2019), 8611-8617.

De Oliveira, H. F. N., et al., "Beyond a solvent: the roles of 1-butyl-3-methylimidazolium chloride in the acid-catalysis for cellulose depolymerisation", Chem. Sci., 6, (2015), 5215-5224.

Dowlut, Meenakshi, et al., "An improved class of sugar-binding boronic acids, soluble and capable of complexing glycosides in neutral water", J. Am. Chem. Soc., 128, (2006), 4226-4227.

Gunasekara, Roshan W., et al., "A General Method for Selective Recognition of 40 Monosaccharides and Oligosaccharides in Water", J. Am. Chem. Soc., 139, (2017), 829-835.

Himmel, M. E., et al., "Biomass Recalcitrance: Engineering Plants and Enzymes for Biofuels Production", Science, 315(5813), (2007), 804-807.

Hu, Lan, et al., "A Bait-and-Switch Method in the Construction of Artificial Esterases for Substrate-Selective Hydrolysis", Chemistry—Eur. J., 25(32), (2019), 7702-7710.

Hu, Lan, et al., "Controlling Product Inhibition through Substrate-Specific Active Sites in Nanoparticle-Based Phosphodiesterase and Esterase", ACS Catal., 9, (2019), 5019-5024.

Hu, Lan, et al., "Molecularly Imprinted Artificial Enzymes with Highly Specific Active Sites and Precisely Installed Catalytic Groups", Org. Biomol. Chem., 16, (2018), 5580-5584.

Huang, Yao-Bing, et al., "Hydrolysis of cellulose to glucose by solid acid catalysts", Green Chem., 15, (2013), 1095-1111.

Huber, G. W, et al., "Synthesis of Transportation Fuels from Biomass: Chemistry, Catalysts, and Engineering", Chem Rev., 106(9), (Sep., 2006), 4044-4098.

Jurick II, W. M., et al., "Application of the 2-Cyanoacetamide Method for Spectrophotometric 5 Assay of Cellulase Enzyme Activity", Plant Pathol. J., vol. 11(1), (2012), 48-41.

Lin, Po-Chiao, et al., "Ethylene Glycol-Protected Magnetic Nanoparticles for a Multiplexed Immunoassay in Human Plasma", Small, 2(4), (2006), 485-489.

Luterbacher, J. S., et al., "Targeted chemical upbringing of lignocellulosic biomass to platform molecules", Green Chem., 16, (2014), 4816-4838.

Luterbacher, Jeremy S., et al., "Nonenzymatic Sugar Production from Biomass Using Biomass-Derived y-Valerolactone", Science 343(6168), (2014), 277-280.

Rinaldi, Roberto, et al., "Depolymerization of Cellulose Using Solid Catalysts in Ionic Liquids", Angew. Chem. Int. Ed., 47(42), (2008), 8047-8050.

Rinaldi, Roberto, et al., "Instantaneous dissolution of cellulose in organic electrolyte solutions", Chem. Commun., 47(1), (2011), 511-513.

Robertson, G. Philip, et al., "Cellulosic biofuel contributions to a sustainable energy future: Choices and outcomes", Science, 356(6345), (2017), p. 1349.

Rostovtsev, Vsevolod V., et al., "A Stepwise Huisgen Cycloaddition Process: Copper(I)-Catalyzed Regioselective Ligation' of Azides and Terminal Alkynes", Angew. Chem. Int. Ed., 41(14), (2002), 2596-2599.

Turner, Megan B., et al., "Ionic liquid salt-induced inactivation and unfolding of cellulase from *Trichoderma reesei*", Green Chem., 5, (2003), 443-447.

Wahlstrom, R. M., et al., "Enzymatic hydrolysis of lignocellulosic polysaccharides 25 in the presence of ionic liquids", Green Chem., 17, (2015), 694-714.

Wang, Hui, et al., "Ionic liquid processing of cellulose", Chem. Soc. Rev., 41(4), (2012), 1519-1537.

Xing, Xiaoyu, et al., "Binding-promoted chemical reaction in the nanospace of a binding site: effects of environmental constriction", Org. Biomol. Chem., 16(16), (2018), 2855-2859.

Zechel, D. L., et al., "Glycosidase mechanisms: Anatomy of a finely tuned catalyst", Acc. Chem. Res., 33(1), (2000), 11-18.

Zhang, Zhanrong, et al., "Catalytic Transformation of Lignocellulose into Chemicals and Fuel Products in Ionic Liquids.", Chem. Rev., 117(10), (2017), 6834-6880.

Zing, X., et al., "Fluorescent nanoparticle sensors with tailor-made recognition units and proximate fluorescent reporter groups", New J. Chem., 42, (2018), 9377-9380.

\* cited by examiner

SYNTHETIC CATALYSTS FOR CARBOHYDRATE PROCESSING

CROSS REFERENCE TO RELATED APPLICATION

This application claims priority to U.S. provisional patent application No. 63/048,370, which was filed on Jul. 6, 2020, and which is hereby incorporated by reference in its entirety.

STATEMENT OF GOVERNMENT SUPPORT

This invention was made with government support under Contract Nos. CHE-1708526 awarded by the National Science Foundation, and R01 GM138427 awarded by the National Institutes of Health. The government has certain rights in the invention.

TECHNICAL FIELD

This disclosure relates to a novel class of biomimetic catalysts to manipulate carbohydrates through selective hydrolysis.

BACKGROUND

Carbohydrates are the most abundant biomolecules on earth and serve a plethora of purposes including energy storage, structural support, cell signaling, and immunity. Most organisms use 1-3% of their genomes to encode proteins for the synthesis and hydrolysis of carbohydrates. The majority of these enzymes, however, cannot be obtained easily. In addition, enzymes tend to have narrow operating windows and robust catalysts with glycosidic activities are in great need for applications such as biomass conversion.

A key challenge in biomass conversion is the depolymerization of cellulose, which makes up 35-50% of lignocellulosic biomass. Whether for chemical or fuel production, cellulose first needs to be converted into soluble monomeric and oligomeric sugars, usually through catalytic hydrolysis. However, cellulose is highly crystalline with its $\beta$-1,4-linked glucose polymer chains stabilized by strong inter- and intramolecular hydrogen bonds, making the depolymerization extremely challenging. Soluble acid catalysts require corrosion-resistant equipment and generate large amounts of waste. Solid acids can alleviate these problems but demand high temperatures for operation and experience slow mass transfer during reaction. Both soluble and insoluble acids can easily decompose sugar products in the hydrolysis and some of the side products formed such as 5-hydroxymethylfurfural inhibit microbial fermentation in bioethanol production. Enzymatic catalysts (i.e., cellulases) can break down cellulose under mild conditions but are limited by their high costs and narrow operating window in terms of reaction temperature and medium. The enzymes, plus necessary physical and chemical pretreatments of cellulosic materials, constitute nearly one third of the total cost of cellulose-derived ethanol.

Hydrolysis of acetal—the dominant functional group in glycosidic linkages—in principle can be accomplished simply with acidic water. The challenge in developing synthetic catalysts that mimic natural glycosidases to hydrolyze glycans is in the selectivity of the process. Because inversion of a single stereogenic center on a monosaccharide or oligosaccharide can change its biological property, the catalyst needs to differentiate $\alpha$ and $\rho$ anomers, as well as the building blocks making up the glycan.

Selective hydrolysis of glycans is also important in modern glycomics.

Carbohydrates or glycans are involved in numerous biological processes and all major human diseases. Glycosylation is the most common post-translational modification of proteins. Glycoscience, however, lags behind genomics and proteomics, due to the extreme complexity, dynamic structural diversity, and micro-heterogeneity of glycans found in biological systems. Another reason, according to the 2012 NRC report "Transforming Glycoscience", is the lack of suitable tools and methods "to detect, describe, and fully purify glycans . . . and then to characterize their chemical composition and structure." Catalysts that selectively hydrolyze glycans are particularly useful in analytic glycomics for glycan release from glycoproteins, in functional glycomics to understand the structure-activity relationship of glycans, and in glycan synthesis by hydrolyzing specific oligosaccharides from natural glycan sources.

SUMMARY OF THE INVENTION

The disclosure relates to a molecularly-imprinted cross-linked micelle, the micelle comprising:
  an imprint of the functional or structural analogue of a glycan;
  a binding unit and an acid unit, wherein the binding unit is bindable to the glycan;
  and the acid unit is proximal to a glycosidic bond of the glycan during binding of the glycan to the binding unit.

The disclosure also relates to a method of making the micelle of the disclosure.

The disclosure also relates to a method of hydrolyzing an oligosaccharide or polysaccharide comprising contacting the oligosaccharide or polysaccharide (e.g., a cellulose) with a micelle of the disclosure.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1A:
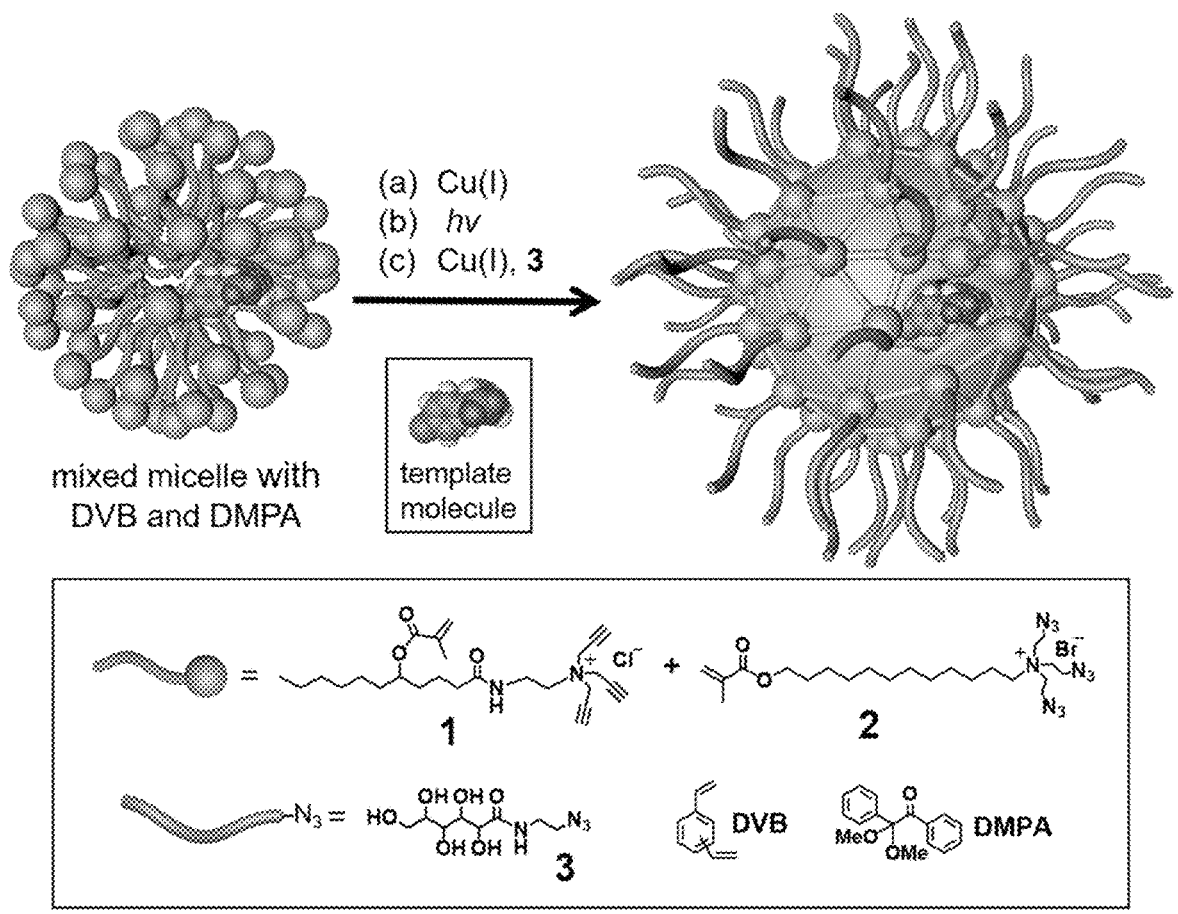
FIG. 1A is the preparation of molecularly imprinted nanoparticle (MINP) through templated polymerization in micelle.

This disclosure describes synthetic catalysts that mimic natural glycosidases to hydrolyze glycans selectively, and methods of making them. The catalysts can target a glycosidic linkage by having acidic groups near its exocyclic oxygen, while recognizing the adjacent sugar residues with reversible boronate ester and/or micelle-stabilized hydrogen bonds. The generality of the hydrolytic mechanism and the glycan-recognition makes these synthetic glycosidases a platform technology with a wide range of applications.

The disclosure relates in part to a molecularly-imprinted cross-linked micelle selective for a glycan, the micelle comprising: an imprint of the functional or structural analogue of a glycan; a binding unit and an acid unit, wherein the binding unit is bindable to the glycan; and the acid unit is proximal to a glycosidic bond of the glycan during binding of the glycan to the binding unit. The disclosure also relates to method of making and using such micelles.

For the present disclosure to be more readily understood, some terms and phrases are defined below and throughout the specification.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, to A only (optionally including elements other than B); or to B only (optionally including elements other than A); or yet, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, to at least one, optionally including more than one, A, with no B present (and optionally including elements other than B); or to at least one, optionally including more than one, B, with no A present (and optionally including elements other than A); or yet, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to.

The term "photocleavable moiety" means any agent attached to the glycan that contains a photocleavable bond. This allows part of the structure to be removed on exposure to electromagnetic energy such as light energy of any desired variety whether visible, UV, X-ray or the like (e.g. microwave). The photocleavable moiety employed can couple to hydroxy residues present in the glycan.

Suitable photocleavable moieties are well known from the art, for example Biological Applications of Photochemical Switches, Ed H Morrison, Bioorganic Photochemistry Series, Volume 2, J. Wiley & Sons, which is incorporated herein by cross-reference, especially Chapter 1, Section 4, pages 34-50.

The term "bindable", as used herein, refers to the binding unit interacting with the glycan by noncovalent and/or reversible covalent bonds.

The term "oligosaccharide", as used herein, comprises 4 to 20 monosaccharide units that can be linear or branched.

The term "polysaccharide", as used herein, comprises 20 or more monosaccharide units that can be linear or branched.

The term "proximal", as used herein, refers to the position of the acid relative to the glycosidic bond of the glycan during binding of the glycan to the binding unit, wherein the distance between the two allows for catalytic hydrolysis to occur.

Micelles

The disclosure relates to a molecularly-imprinted cross-linked micelle selective for a glycan, the micelle comprising:
  an imprint of the functional or structural analogue of a glycan;
  a binding unit and an acid unit, wherein the binding unit is bindable to the glycan;
  and the acid unit is proximal to a glycosidic bond of the glycan during binding of the glycan to the binding unit.

The micelle can be obtained from a functional analogue of a glycan as a template. The micelle can be obtained from a structural analogue of a glycan as a template.

The functional or structural analogue of the glycan can be a monosaccharide. The functional or structural analogue of the glycan can be an oligosaccharide. The functional or structural analogue of the glycan can be glucose. The functional or structural analogue of the glycan can be glucose, maltose, or maltotriose.

The acid unit can be a mono acid unit. The acid unit can be a double acid unit. The double acid can be installed in a single reaction or step. The double acid can be installed in separate reactions or steps. The acid unit can be a poly acid unit. The acid unit can be covalently bound to the micelle. The acid unit can be covalently bound to the micelle by polymerization. The acid unit can be bound to the micelle by metal-ligand complexation. The acid unit can be non-covalently bound to the micelle. The acid unit can be a Brønsted acid. The acid unit can have a $pK_a$<5. The acid unit can be a carboxylic acid. The acid unit can be a sulfonic acid. The acid unit can be a phosphonic acid. The acid unit can be a Lewis acid. The acid unit can comprise a hydrophobic group. The acid unit can comprise an adamantyl group. The acid unit can comprise a pyrenyl group.

The micelle can be obtained from cross-linkable surfactants containing one or more functional groups that are polymerizable and cross-linkable. The surfactants can comprise one or more terminal alkyne groups on the surfactant headgroup. The surfactants can comprise one or more terminal azido groups on the surfactant headgroup. The surfactants can comprise one or more vinyl groups on the surfactant headgroup. The surfactants can comprise one or more thiol groups on the surfactant headgroup. The surfactants can comprise one or more polymerizable vinyl groups. The polymerizable vinyl groups can be polymerized by free radical polymerization.

The micelle can comprise a surface and a core, and can be cross-linked on the surface by covalent bonds. The micelle can comprise a surface and a core, and can be cross-linked in the core by covalent bonds.

The binding unit can comprise a boroxole. The binding unit can comprise a boronic acid. The binding unit can comprise a hydrogen-bonding group. The binding unit can comprise an amide group.

The method also relates to a material comprising the micelle of the disclosure, wherein the micelle is bonded to a solid support.

The micelle can be covalently bonded to the solid support. The micelle can be noncovalently bonded to the solid support.

Method of Making Micelles.

The disclosure relates to a method of making the molecularly imprinted micelle of the disclosure, comprising:
cross-linking the surface of a micelle comprising a cross-linkable surfactant, a functional or structural analogue of a glycan, a functional monomer that binds the glycan or analogue by covalent and/or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit to the imprinted site by covalent bond formation, metal-ligand complexation, or non-covalent interactions.

The disclosure relates to a method of making the molecularly imprinted micelle of the disclosure, comprising:
cross-linking the surface of a micelle comprising a cross-linkable surfactant, a functional or structural analogue of a glycan, a functional monomer that binds the glycan or analogue by covalent and/or noncovalent bonds, a free radical cross-linker, and a free radical initiator;
cross-linking the surface of the micelle;
cross-linking the core of the micelle;
removing a portion or the entire functional or structural analogue of the glycan to expose a reactive group in the imprinted site; and
attaching an acid unit to the reactive group by covalent bond formation.

The disclosure relates to a method of making the molecularly imprinted micelle of the disclosure, comprising:
cross-linking the surface of a micelle comprising a cross-linkable surfactant, a functional or structural analogue of a glycan, a functional monomer that binds the glycan or analogue by covalent and/or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit by metal-ligand complexation to the imprinted site.

The disclosure relates to a method of making the molecularly imprinted micelle of the disclosure, comprising:
cross-linking the surface of a micelle comprising a cross-linkable surfactant, a functional or structural analogue of a glycan, a functional monomer that binds the glycan or analogue by covalent and/or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit by non-covalent interactions to the imprinted site.

The methods can further comprise attaching ligands to the surface of the micelle.

The methods can further comprise attaching the micelle to a solid support.

The cross-linkable surfactant can comprise one or more functional groups that are polymerizable and cross-linkable. The surfactants can comprise one or more terminal alkyne groups on the surfactant headgroup. The surfactants can comprise one or more terminal azido groups on the surfactant headgroup. The surfactants can comprise one or more vinyl groups on the surfactant headgroup. The surfactants can comprise one or more thiol groups on the surfactant headgroup. The surfactants can comprise one or more polymerizable vinyl groups. The polymerizable vinyl groups can be polymerizable by free radical polymerization.

The functional or structural analogue of a glycan can be covalently bonded to one or more cleavable, polymerizable moieties. The cleavable, polymerizable moiety can contain an imine. The cleavable, polymerizable moiety can contain an ortho-nitrobenzyl ester.

The functional or structural analogue of a glycan can be covalently bonded to one or more hydrophobic groups. The functional or structural analogue of a glycan can be covalently bonded to one or more adamantyl groups. The functional or structural analogue of a glycan can be covalently bonded to one or more pyrenyl groups.

The functional monomer can covalently bind to the glycan or analogue. The functional monomer can noncovalently bind to the glycan or analogue. The functional monomer can contain a boroxole group. The functional monomer can contain a boronic acid.

The functional monomer can contain one or more acid groups.

The functional monomer can be 4-vinylbenzoic acid.

The free radical cross-linker can be divinylbenzene (DVB). The free radical cross-linker can be N,N'-methylenebisacrylamide (MBAm).

The free radical initiator can be a thermal initiator. The free radical initiator can be a photoinitiator. The thermal initiator can be 2,2'-azobis(2-methylpropionitrile) (AIBN). The photoinitiator can be 2,2-dimethoxy-2-phenylacetophenone (DMPA).

Cu(I) catalysts can be used to cross-link the surface of the micelle, such as via bonding/cross-linking of reactive groups.

The reactive group can be an aldehyde. The reactive group can be a carboxylic acid. The reactive group can be an amine. The reactive group can be a thiol. The reactive group can be a C—H bond. The acid unit can be bonded to the reactive group by reductive amination. The acid unit can be bonded to the reactive group by amide bond formation. The reactive unit can be bonded to the reactive group by a C—S bond. The reactive group can be bonded to the reactive group by a C—N bond. The reactive group can be bonded to the reactive group by a C—C bond.

The acid unit can be attached to the imprinted site by hydrophobic interactions and/or other noncovalent interactions.

Methods of Using Micelles.

The disclosure relates to a method of hydrolyzing an oligosaccharide or polysaccharide comprising contacting the oligosaccharide or polysaccharide with a micelle of the disclosure.

The method can comprise dissolving and/or suspending the oligosaccharide or polysaccharide in an aqueous buffer. The aqueous buffer can be a sodium acetate buffer.

The method can comprise dissolving and/or suspending the oligosaccharide or polysaccharide in a weak acid. The weak acid can be $H_3PO_4$.

The method can comprise dissolving and/or suspending the oligosaccharide or polysaccharide in an ionic liquid. The ionic liquid can be 1-ethyl-3-methylimidazolium acetate ([$C_2$mim]OAc).

The method can comprise dissolving and/or suspending the oligosaccharide or polysaccharide in a mixture of ionic liquids and organic solvent. The mixture can comprise 1-ethyl-3-methylimidazolium acetate and DMSO.

The method can comprise dissolving and/or suspending the oligosaccharide or polysaccharide in water.

The polysaccharide can be cellulose.

EXAMPLES

Various embodiments of the present invention can be better understood by reference to the following Examples which are offered by way of illustration. The present invention is not limited to the Examples given herein.

Materials and Methods

All organic solvents and reagents were of ACS-certified grade or higher grade and were purchased from Fisher Scientific and dried using standard procedures. Ultrapure water (18.2 MU; Millipore Co., USA) was used in all the preparation of buffers and nanoparticles. Flash column chromatography was performed on SiliFlash P60 silica gel (40-63 μm, 60 Å). 1-Ethyl-3-methylimidazolium acetate ([$C_2$mim]OAc, 98% HPLC grade, CAS No. 143314-17-4) and 1-butyl-3-methylimidazolium chloride ([$C_4$mim]Cl, 98% HPLC grade, CAS No. 97717-90-1) were purchased from Sigma-Aldrich and used as received. Cellulose (microcrystalline, powder, type 20, 20 μm, CAS No. 9004-34-6) was purchased from Sigma-Aldrich.

All reactions and manipulations were performed using standard Schlenk techniques. NMR spectra ($^1$H and $^{13}$C NMR) were recorded on a Bruker DRX-400, Bruker AV III 600, or Varian VXR-400 spectrometer. Chemicals shifts are reported in ppm relative to residual solvent peaks ($CDCl_3$=7.26 ppm for $^1$H NMR and 77.16 ppm for $^{13}$C NMR, $CD_3OD$=3.31 ppm for $^1$H NMR and 49.00 for $^{13}$C NMR). Coupling constants are reported in hertz. ESI-mass spectrometry was recorded on an Agilent QTOF 6540 mass spectrometer with a QTOF detector. Dynamic light scattering (DLS) was performed on a Malvern Zetasizer Nano ZS. Isothermal titration calorimetry (ITC) was performed on a MicroCal VP-ITC Microcalorimeter with Origin 7 software and VPViewer2000 (GE Healthcare, Northampton, MA). Transmission electron microscopy (TEM) was performed on a 200 kV JEOL 2100 scanning/transmission electron microscope (STEM) with <1.4 Å resolution and integrated software package for computerized control. UV-vis spectra were recorded on a Cary 100 Bio UV-visible spectrophotometer. LC-MS analysis was performed with a Thermo Scientific HILIC-LC column (4.6 mm, 150 mm) coupled to an Agilent 1200 Series Binary VWD system with an Agilent 6540 UHD Accurate Mass Q-TOF mass spectrometry detector.

Dynamic Light Scattering

Particle size of MINP was determined on a Malvern Zetasizer Nano ZS using the Zetasizer software according to the Stokes-Einstein equation (1). The volume of a spherical nanoparticle ($V_{D_h}$) was calculated from equation (2). Assuming a density of 1.37 g/cm³ (the density of protein), the molecular weight of the particle can be calculated using equation (3). A nanoparticle with hydrodynamic diameter of 4.87 nm has a calculated molecular weight of 50 kDa.

$$D_h = \frac{k_B T}{6\pi\eta D_t} \quad (1)$$

in which $D_h$ is the hydrodynamic diameter, D the translational diffusion coefficient measured by dynamic light scattering, T the temperature, kB the Boltzmann's constant, and η is dynamic viscosity of water (0.890 cP at 298 K).

$$V_{D_h} = \frac{4\pi}{3}\left(\frac{D_h}{2}\right)^3 \quad (2)$$

$$Mw \text{ in dalton} = \left(\frac{D_h}{0.132}\right)^3 \quad (3)$$

in which $D_h$ is the hydrodynamic diameter in nm.

Transmission Electron Microscope

For the TEM imaging, 0.1 mg of MINP was dissolved in 1 mL of Millipore water and the solution was ultra-sonicated for 10 min. A micro syringe was used to load one small drop (~1 μL) of the above solution onto a TEM copper grid covered with carbon film. The sample was left to form a thin layer, and then one small drop (~1 μL) of 2% uranyl acetate solution was loaded on the grid for the negative staining. The sample was left to dry and analyzed on a 200 kV JEOL 2100 scanning/transmission electron microscope (STEM).

ITC Binding Studies

The determination of binding constants by ITC followed standard procedures at 298.15 K. In general, a solution of an appropriate sugar in 10 mM HEPES buffer (pH 7.4) was injected in equal steps into 1.43 mL of the corresponding MINP in the same solution. The top panel shows the raw calorimetric data. The area under each peak represents the amount of heat generated at each ejection and is plotted against the molar ratio of the MINP to the guest. The smooth solid line is the best fit of the experimental data to the sequential binding of N binding site on the MINP. The heat of dilution for the guest, obtained by titration carried out beyond the saturation point, was subtracted from the heat released during the binding. Binding parameters were auto-generated after curve fitting using Microcal Origin 7.

Hydrolysis of Cellobiose

In a typical procedure, the appropriate MINP stock solution (100 μM) in MES buffer (10 mM, pH=6.0) was diluted by the same buffer to 20 μM in a volume of 990 μL and sonicated for 30 seconds. A 10 μL aliquot of a 20 mM cellobiose stock solution in the MES buffer was added so that the total volume of the reaction mixture was 1.00 mL.

After the reaction was allowed to react at the designated temperature for 12 hours, the reaction mixture was centrifuged at 20,000 RPM for 10 minutes remove the MINP catalyst before LC-MS analysis.

Hydrolysis of cellobiose was monitored by LC-MS analysis using an Agilent 1200 Series Binary VWD system with an Agilent 6540 UHD Accurate Mass Q-TOF mass detector. Separation of the products was performed on a Thermo Scientific HILIC-LC column (4.6 mm, 150 mm) at 60° C. For quantitative analysis, injection volumes were adjusted for the signal intensity to stay within the linear range of the calibration curve. All samples were centrifuged at 20,000 RPM before analysis to remove the MINP particles (to avoid column blockage over extended usage). Comparison with non-centrifuged samples showed no change in glucose concentration during the centrifugation step. The mobile phase was a mixture of acetonitrile and water, with 0.1% formic acid. Product peaks were identified by a high-resolution mass detector in the negative ion mode.

Hydrolysis of Cellulose

A well-established spectrophotomeric assay was used to monitor the hydrolysis of hydrolysis (Jurick Ii, W. M. Application of the 2-Cyanoacetamide Method for Spectrophotometric Assay of Cellulase Enzyme Activity. *Plant Pathol. J.* 2012, 11, 38-41). In a typical procedure, a reaction mixture containing SigmaCell cellulose (5.0 mg/mL) and the appropriate catalyst (cellulase or MINP at 5.0 mg/mL) in 1.0 mL of NaOAc buffer (50 mM, pH 5.0) was incubated at 37° C. for 12 hours. A 50 µL aliquot of the reaction mixture was added to 1.0 mL of a cyanoacetamide solution (25 mM, with 2 mM NaOH) and the mixture was allowed to sit at 95° C. for 1 hour. The concentration of reducing sugar (i.e., "glucose equivalents") was determined by the absorbance at 275 nm at 25° C. using a calibration curve generated from authentic samples.

For the hydrolysis in ionic liquids, a reaction mixture containing SigmaCell cellulose (8.0 mg/mL) and the appropriate catalyst (cellulase or MINP at 5.0 mg/mL) in 0.50 mL of the appropriate solvent at the indicated temperature 24 hours. A 50 µL aliquot of the reaction mixture was added to 1.0 mL of a cyanoacetamide solution (25 mM, with 2 mM NaOH) and the mixture was allowed to sit at 95° C. for 1 hour. The concentration of reducing sugar (i.e., "glucose equivalents") was determined by the absorbance at 275 nm at 25° C. using a calibration curve generated from authentic samples. Formation of glucose was confirmed independently by LC-MS analysis.

Analysis of Catalytic Hydrolysis Reactions Using LC/MS

Hydrolysis of maltose and maltohexaose was monitored by LC-MS analysis using an Agilent 1200 Series Binary VWD system with an Agilent 6540 UHD Accurate Mass Q-TOF mass detector. Separation of the products was performed on a Thermo Scientific HILIC-LC column (4.6 mm, 150 mm) at 60° C. For quantitative analysis, injection volumes were adjusted for the signal intensity to stay within the linear range of the calibration curve. All samples were centrifuged at 20,000 RPM before analysis to remove the MINP particles (to avoid column blockage over extended usage). Comparison with non-centrifuged samples showed no change in glycan concentration during the centrifugation step. The mobile phase was a mixture of acetonitrile and water, with 0.1% formic acid. Product peaks were identified by a high-resolution mass detector in the negative ion mode.

Hydrolysis of Maltose and Maltohexaose by MINPs

A 20 µL aliquot of a 100 µM MINP stock solution in Millipore water was diluted by water or a 10 mM MES buffer (pH 6.0) to 990 µL and sonicated for 0.5 min. To this solution, a 10 µL aliquot of a 20 mM maltose stock solution (or 10 mM maltohexaose stock solution) was added. The reaction mixture was allowed to react in a Benchmark block heater at 60 or 90° C. for the indicated time. The reaction mixture was centrifuged (20,000 RPM for 10 min) to remove the MINP catalyst before LC-MS analysis.

Hydrolysis of p-Nitrophenyl Glycopyranosides by MINPs

Stock solutions (5 mM) of p-nitrophenyl glycopyranosides in 10 mM MES buffer pH 6.0 were prepared. The stock solutions were stored in a refrigerator and used within 3 days. A stock solution of catalyst containing the appropriate MINP (100 µM) and adamantane acid (100 or 200 µM) in 10 mM MES buffer pH 6.0 were prepared. For the kinetic experiments, a typical procedure is as follows. An aliquot of 100 µL of the catalyst stock solution was combined with 1860 µL of 10 mM MES buffer pH 6.0 in a cuvette. The cuvette was vortexed gently before it was placed in a UV/Vis spectrometer and equilibrated to 40.0° C. for 10 min. Then an aliquot of L of the substrate stock solution was added. The hydrolysis was monitored by the absorbance of p-nitrophenol at 320 nm (pH 5.0, 6.0 or 6.5) or p-nitrophenoxide at 400 nm (pH 7 or 7.4). The concentration of p-nitrophenol or p-nitrophenoxide was calculated based on the calibration curve obtained from authentic samples. All the experiments were performed in triplicates. The reaction rates were calculated based on pseudo-first order kinetics and the averages were reported.

Results

Discussion of Results

Hydrolysis of Cellulose

To prepare a synthetic glycosidase to bind and hydrolyze cellulose, catalyst needs to bind the cellulose and position an acidic group near a glycosidic bond. One method for synthesizing such a catalyst is shown in FIG. 1A. The synthesis was started with spontaneous formation of mixed micelles of 1 and 2 containing a template molecule, divinylbenzene (DVB, a free radical cross-linker), and 2,2-dimethoxy-2-phenylacetophenone (DMPA, a photoinitiator). Addition of Cu(I) catalysts cross-linked the surface of the micelle by the highly efficient alkyne-azide "click" reaction, facilitated additionally by the proximity of reactive groups. UV-induced free-radical polymerization then cross-linked the micelle core around the template, and a second click reaction between 3 and the residual alkynes on the micelle installed a layer of hydrophilic ligand on the surface. The surface ligands allowed purification of the resulting molecularly imprinted nanoparticles (MINPs) by simple precipitation and washing with organic solvents.

Figure 1B:
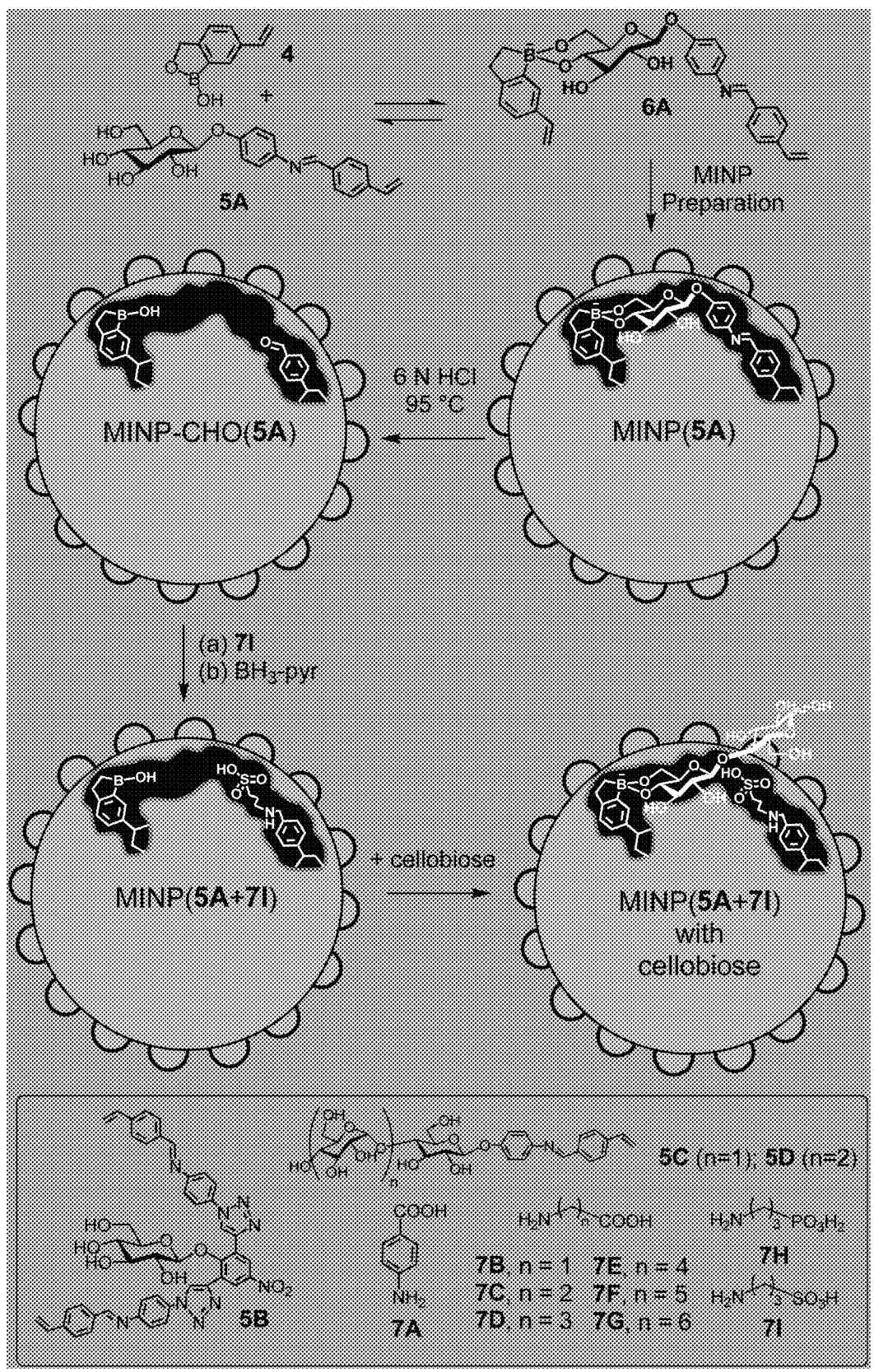
FIG. 1B is the preparation of artificial glycosidase MINP (5A+7I) and its binding of cellobiose. The surface ligands are omitted from the drawing for clarity.

Micellar imprinting can reproduce structural features of the template with extraordinary accuracy due to a nanoconfinement effect. To create a cellulose-binding active site within MINP, vinylphenylboroxole 4 was reacted with glucoside template 5A to form an amphiphilic, anionic boronate ester 6A. Micellar imprinting afforded MINP(5A), with template 5A covalently polymerized into the micellar core (FIG. 1B). Hydrolysis of the imine (and boronate) with 6 N hydrochloric acid and reductive amination of the resulting aldehyde using 7A-I produced MINP (5A+7A-I) as the synthetic glycosidase.

MINP (5A+7A-I) has a boroxole group in the active site to bind the terminal glucose of cellulose, with an acid positioned near the glycosidic bond to catalyze the hydrolysis. Boronate 6A has two hydroxyl groups and its amphiphilicity helps position itself near the surface of the micelle-a feature that can be important to the removal of the template to vacate the imprinted site after micellar imprinting. In the final catalyst, proximity of the active site to the surface can help the unbound glucose units of the substrate (cellobiose or cellulose) stay in the solution while the terminal glucose engages in reversible boronate formation.

Amines 7A-I allowed the introduction of different acids in the active site, with its flexibility and distance to the glycosidic bond tuned systematically. At 60° C. and in pH 6 buffer, MINP(5A+7A-I), hydrolyzed cellobiose, a model substrate, in a 21-64% yield in 24 h (Table 1). It is interesting that 7A, which was similar in dimension to the part of the aryl aglycon removed by imine hydrolysis, yielded a less active catalyst than 7I. A tightly fit active site thus may be less efficient than one with some flexibility. When the number of methylene groups (n=3) stayed the same with 7D, 7H, and 7I, the most acidic sulfonic acid gave the fastest hydrolysis.

TABLE 1

Hydrolysis of cellobiose catalyzed by MINPs in 10 mM MES buffer (pH 6).[a]

| Entry | catalysts | temp. (° C.) | yield (%) |
|---|---|---|---|
| 1 | MINP(5A + 7A) | 60 | 42 |
| 2 | MINP(5A + 7B) | 60 | 22 |
| 3 | MINP(5A + 7C) | 60 | 25 |
| 4 | MINP(5A + 7D) | 60 | 51 |
| 5 | MINP(5A + 7E) | 60 | 21 |
| 6 | MINP(5A + 7H) | 60 | 57 |
| 7 | MINP(5A + 7I) | 60 | 64 |
| 8 | MINP(5A + 7I) | 90 | 74 |
| 9 | MINP(5B + 7C) | 60 | 0 |
| 10 | MINP(5B + 7D) | 60 | 17 |
| 11 | MINP(5B + 7E) | 60 | 54 |
| 12 | MINP(5B + 7F) | 60 | 94 |
| 13 | MINP(5B + 7G) | 60 | 77 |
| 14 | MINP(5B + 7F) | 90 | 98 |
| 15 | NINP with 7F [b] | 60 | 0 |
| 16 | 7I | 60 | ~2 |
| 17 | 7F | 60 | ~1 |
| 18 | None | 60 | 0 |

[a]Reactions were performed with 0.2 mM of cellobiose and 20 μM of catalysts in 1.0 mL MES buffer (10 mM, pH = 6.0) for 24 h. Yields were determined by LC-MS using standard curves generated from authentic samples.
[b] NINP was nonimprinted nanoparticle prepared with 1 equiv. FM 4 but without any template.

A highly conserved feature of natural glycosidase is a pair of carboxylic acids that work cooperatively to afford up to $10^{17}$-fold rate acceleration (Zechel, D. L.; Withers, S. G. Glycosidase mechanisms: Anatomy of a finely tuned catalyst. Acc. Chem. Res. 2000, 33, 11-18). One acid normally acts as a general acid to protonate the glycosidic oxygen, and the other carboxyl-5-11 Å apart—as a general base to deprotonate the attacking nucleophilic water (in inverting glycosidases) or as the attacking nucleophile (in retaining glycosidases). Template 5B was synthesized, which had two imine bonds and could form two acids sandwiching the glycosidic bond (FIG. 1). The optimized diacidic catalyst, i.e., MINP(5B+7F), hydrolyzed cellobiose significantly better (94% yield at 60° C.) than the best monoacidic MINP (5A+7I), despite the more acidic sulfonic acid in the latter (Table 1). Control experiments showed that nonimprinted nanoparticles (NINPs) and the α,ω-amino acids themselves (7I and 7F) were inactive.

Formation of the boroxole-functionalized binding sites in both the intermediate aldehyde-derived MINPs and the final catalysts were confirmed by binding studies. Isothermal titration calorimetry (ITC) showed a stronger binding constant ($K_a$) of 16-23×10$^3$ M$^{-1}$ for glucose in aqueous buffer by the double acidic MINPs than by the mono acidic ones (Table 2). Binding for cellobiose was slightly weaker than for glucose. The nonimprinted nanoparticle (NINP) prepared with 4 in the absence of template showed negligible binding.

TABLE 2

ITC binding data for sugar guests by MINPs.[a]

| Entry | MINP | guest | pH | $K_a$ (×10$^3$ M$^{-1}$) | ΔG (kcal/mol) | N |
|---|---|---|---|---|---|---|
| 1 | MINP-CHO(5A) | glucose | 7.4 | 8.85 ± 0.68 | −5.38 | 1.03 ± 0.03 |
| 2 | MINP-CHO(5A) | maltose | 7.4 | 6.69 ± 0.40 | −5.22 | 1.26 ± 0.04 |
| 3 | MINP-CHO(5A) | maltotriose | 7.4 | 5.72 ± 0.29 | −5.13 | 0.95 ± 0.07 |
| 4 | MINP-CHO(5A) | maltohexaose | 7.4 | 1.56 ± 0.35 | −4.35 | 0.83 ± 0.61 |
| 5 | MINP(5A + 7I) | glucose | 7.4 | 9.07 ± 0.86 | −5.40 | 0.83 ± 0.09 |
| 6 | MINP-CHO(5B) | glucose | 7.4 | 17.40 ± 1.92 | −5.78 | 1.01 ± 0.03 |
| 7 | MINP-(5B + 7F) | glucose | 7.4 | 22.60 ± 1.07 | −5.94 | 0.91 ± 0.03 |
| 8 | MINP(5A + 7I) | glucose | 6.0 | 7.52 ± 0.79 | −5.28 | 0.95 ± 0.07 |
| 9 | MINP(5A + 7I) | cellobiose | 6.0 | 5.71 ± 0.51 | −5.12 | 0.78 ± 0.08 |
| 10 | MINP-(5B + 7F) | glucose | 6.0 | 15.70 ± 1.32 | −5.72 | 0.79 ± 0.09 |
| 11 | MINP-(5B + 7F) | cellobiose | 6.0 | 6.98 ± 1.52 | −5.24 | 1.06 ± 0.17 |
| 12 | MINP-CHO(5C) | glucose | 7.4 | 12.9 ± 1.1 | −5.62 | 1.03 ± 0.03 |
| 13 | MINP-CHO(5C) | maltose | 7.4 | 27.20 ± 6.47 | −6.05 | 1.22 ± 0.08 |
| 14 | MINP-CHO(5C) | maltotriose | 7.4 | 11.30 ± 1.52 | −5.53 | 1.01 ± 0.04 |
| 15 | MINP-CHO(5D) | glucose | 7.4 | 7.02 ± 0.43 | −5.24 | 1.10 ± 0.02 |
| 16 | MINP-CHO(5D) | maltose | 7.4 | 11.10 ± 0.90 | −5.51 | 0.95 ± 0.04 |
| 17 | MINP-CHO(5D) | maltotriose | 7.4 | 35.70 ± 2.98 | −6.21 | 1.14 ± 0.03 |
| 18 | NINP [c] | glucose | 7.4 | <0.05 [b] | —[b] | —[b] |

[a]The FM/template ratio in the MINP synthesis was 1:1 unless otherwise indicated. The cross-linkable surfactants were a 3:2 mixture of 1 and 2. The titrations were performed in 10 mM HEPES buffer at 298K.
[b] Below detection limit.
[c] The particle was prepared with 1.0 equiv. FM 4 but without the any template and binding was extremely weak.

MINP(5B+7F) displayed enzyme-like Michaelis-Menten kinetics in the hydrolysis of cellobiose, with $k_{cat}$=0.087 min$^{-1}$ and $K_m$=0.66 mM in pH 6 buffer at 60° C. The catalytic efficiency ($k_{cat}/K_m$) was 132 M$^{-1}$ min$^{-1}$, roughly $1/14^{th}$ of that of digestive β-glucosidase GH1 from Spodoptera frugiperda at 37° C. ($k_{cat}/K_m$=1780 M$^{-1}$ min$^{-1}$, $k_{cat}$=of 5.7 min$^{-1}$ and $K_m$=3.2 mM) (Tamaki, F. K.; Araujo, E. M.; Rozenberg, R.; Marana, S. R. A Mutant B-Glucosidase Increases the Rate of the Cellulose Enzymatic Hydrolysis. Biochem. Biophys. Rep. 2016, 7, 52-55). In comparison to the natural enzyme, the MINP catalyst had a lower catalytic turnover but stronger binding for the substrate (Table 3).

TABLE 3

Michaelis-Menten parameters of β-glucosidase and MINP catalysts for cellobiose hydrolysis.

| Entry | Catalyst | $V_{max}$ (μM/min) | $K_m$ (mM) | $k_{cat}$ (min$^{-1}$) | $k_{cat}/K_m$ (M$^{-1}$ min$^{-1}$) | Catalytic efficiency Ratio |
|---|---|---|---|---|---|---|
| 1 [a] | β-glucosidase | 18.88 ± 3.65 | 4.57 ± 1.77 | 2.55 | 558 | 1 |
| 2 [b] | MINP(5B + 7F) | 0.50 ± 0.10 | 0.34 ± 0.10 | 0.050 | 147 | 0.26 |
| 3 [c] | MINP(5A + 7I) | 0.39 ± 0.12 | 0.49 ± 0.23 | 0.019 | 40 | 0.07 |

[a] Reaction conditions: [β-glucosidase] = 7.4 μM (1 mg/mL), [Cellobiose] = 0.5-8 mM, T = 37° C. in 10 mM NaOAc buffer pH 5.0;
[b] [MINP(5B + 7F)] = 10 μM, [Cellobiose] = 40-200 μM, T = 60° C. in 10 mM MES buffer pH 6.0;
[c] [MINP(5A + 7I)] = 20 μM, [Cellobiose] = 60-320 μM, T = 60° C. in 10 mM MES buffer pH 6.0.

At 37° C., the enzyme activity of MINP(5B+7F) at 5 mg/mL was within a factor of five to that of a commercial cellulase in the hydrolysis of cellulose (Table 4). The commercial cellulase, isolated from Aspergillus niger, is an endocellulase active on both cellulose and related oligomers (Okada, G. Cellulase of Aspergillus Niger. Meth. Enzymol.

1988, 160, 259-264). While the cellulase lost its activity at higher temperatures in the pH 5 buffer, MINP(5B+7F) became more efficient. Phosphoric acid (83%) dissolved cellulose completely but inactivated the natural enzyme. The synthetic catalyst was ~3 times more active in this extremely acidic condition than in pH 5 buffer.

TABLE 4

Hydrolysis of cellulose by cellulases and MINP(5B + 7F) under different conditions.[a]

| entry | catalysts | catalyst conc. (mg/ml) | solvent | temp (° C.) | enzyme activity ($\mu$mol mg$^{-1}$ h$^{-1}$) | relative activity (enzyme/ MINP) |
|---|---|---|---|---|---|---|
| 1 | MINP(5B + 7F) | 1.0 | buffer[b] | 37 | 0.007 ± 0.001 | 29 |
| 2 | cellulase | 1.0 | buffer[b] | 37 | 0.200 ± 0.011 | — |
| 3 | MINP(5B + 7F) | 2.0 | buffer[b] | 37 | 0.017 ± 0.007 | 9 |
| 4 | cellulase | 2.0 | buffer[b] | 37 | 0.158 ± 0.021 | — |
| 5 | MINP(5B + 7F) | 5.0 | buffer[b] | 37 | 0.024 ± 0.004 | 4.5 |
| 6 | cellulase | 5.0 | buffer[b] | 37 | 0.107 ± 0.019 | — |
| 7 | MINP(5B + 7F) | 5.0 | buffer[b] | 60 | 0.039 ± 0.008 | 0.56 |
| 8 | cellulase | 5.0 | buffer[b] | 60 | 0.022 ± 0.003 | — |
| 9 | MINP(5B + 7F) | 5.0 | buffer[b] | 90 | 0.073 ± 0.012 | 0 |
| 10 | cellulase | 5.0 | buffer[b] | 90 | 0 | — |
| 11 | MINP(5B + 7F) | 5.0 | $H_3PO_4$[c] | 37 | 0.067 ± 0.031 | 0 |
| 12 | cellulase | 5.0 | $H_3PO_4$[c] | 37 | 0 | — |

[a]The reactions were performed in duplicates with [cellulose] = 5.0 mg/mL in 1.0 mL 10 mM NaOAc buffer (pH 5) for 12 h unless indicated otherwise.
[b]pH 5 NaOAc buffer.
[c]83% $H_3PO_4$.

Ionic liquids such as 1-butyl-3-methylimidazolium chloride ([$C_4$mim]Cl) have a tremendous ability to dissolve cellulose and facilitate its acid-catalyzed hydrolysis (Wang, H.; Gurau, G.; Rogers, R. D. Ionic Liquid Processing of Cellulose. *Chem. Soc. Rev.* 2012, 41, 1519-1537). Hydrolysis of cellulose indeed improved significantly as the reaction mixture became homogeneous (Table 5). Polar aprotic solvent (dimethylsulfoxide or DMSO) could also be added to further speed up the hydrolysis as long as the solvent mixture dissolved cellulose. The solvent effect was opposite to that observed for cellulose hydrolysis catalyzed by p-toluenesulfonic acid that increased monotonously with the fraction of ionic liquid in the binary solvent mixture (de Oliveira, H. F. N.; Fares, C.; Rinaldi, R. Beyond a Solvent: The Roles of 1-Butyl-3-Methylimidazolium Chloride in the Acid-Catalysis for Cellulose Depolymerisation. *Chem. Sci.* 2015, 6, 5215-5224). The different solvent effects suggest that the synthetic enzyme operated through a different mechanism from the small-molecule acid catalyst. Here, the higher activity of the double carboxylated catalyst over the monocarboxylated and even the more acidic, monosulfonated catalyst suggests that cooperativity between the bioinspired carboxylic acid pair played a role in the higher activity.

TABLE 5

Hydrolysis of cellulose by MINP(5B + 7F) in mixtures of and ionic liquids and organic solvent.[a]

| entry | solvent | temp. (° C.) | [reducing sugar] (mg/mL) | enzyme activity ($\mu$mol mg$^{-1}$ h$^{-1}$) |
|---|---|---|---|---|
| 1 | [$C_4$mim]Cl | 90 | 0.21 ± 0.04 | 0.024 ± 0.005 |
| 2 | 9:1 [$C_4$mim]Cl/DMSO | 90 | 1.17 ± 0.14 | 0.135 ± 0.016 |
| 3 | 8:2 [$C_4$mim]Cl/DMSO | 90 | 1.41 ± 0.08 | 0.163 ± 0.009 |
| 4 | 7:3 [$C_4$mim]Cl/DMSO | 90 | 1.98 ± 0.21 | 0.229 ± 0.024 |
| 5 | 6:4 [$C_4$mim]Cl/DMSO | 90 | 2.87 ± 0.17 | 0.332 ± 0.020 |
| 6 | 5:5 [$C_4$mim]Cl/DMSO | 90 | 4.17 ± 0.37 | 0.480 ± 0.043 |
| 7 | 4:6 [$C_4$mim]Cl/DMSO[b] | 90 | 1.55 ± 0.11 | 0.179 ± 0.013 |
| 8 | 5:5 [$C_4$mim]Cl/DMSO | 110 | 4.51 ± 0.44 | 0.519 ± 0.051 |
| 9 | 5:5 [$C_4$mim]Cl/DMSO | 130 | 4.97 ± 0.61 | 0.572 ± 0.071 |
| 10 | 5:5 [$C_4$mim]Cl/DMSO + 5% $H_2O$ | 90 | 5.41 ± 0.41 | 0.623 ± 0.047 |
| 11 | 1:9 [$C_2$mim]OAc/DMSO | 90 | 5.87 ± 0.24 | 0.676 ± 0.028 |
| 12 | 2:8 [$C_2$mim]OAc/DMSO + 5% $H_2O$ | 90 | 6.25 ± 0.58 | 0.719 ± 0.067 |

[a]The reactions were performed in duplicates with [cellulose] = 8.0 mg/mL and [MINP] = 2.0 mg/mL in 0.5 mL of solvent for 24 h.
[b]Cellulose dissolved partially in this mixture.

In the 1:1 mixture of [$C_4$mim]Cl/DMSO, the enzyme activity of MINP(5B+7F) reached 0.48 $\mu$mol mg$^{-1}$ h$^{-1}$ at 90° C. Ionic liquids generally inactive cellulase. Hallett and co-workers reported that chemical cationization could greatly stabilize $\beta$-glucosidase in ionic liquids. The enzyme activity of the modified enzyme, nonetheless, remained <0.1 $\mu$mol mg$^{-1}$ h$^{-1}$ for cellulose hydrolysis at the optimal temperature of 110° C. (Brogan, A. P. S.; Bui-Le, L.; Hallett, J. P. Non-Aqueous Homogenous Biocatalytic Conversion of Polysaccharides in Ionic Liquids Using Chemically Modified Glucosidase. *Nat. Chem.* 2018, 10, 859-865). Being a highly cross-linked polymeric nanoparticle, MINP(5B+7F) continued to increase in activity at higher temperatures, up to 0.572 $\mu$mol mg$^{-1}$ h$^{-1}$ at 130° C. A small amount of water may speed up the reaction even further (Table 5, entry 10).

1-Ethyl-3-methylimidazolium acetate ([$C_2$mim]OAc) can dissolve cellulose particularly well in the presence of other organic solvents. A 1:9 [$C_2$mim]OAc/DMSO mixture increased the hydrolytic activity of MINP(5B+7F) to 0.676 $\mu$mol mg$^{-1}$ h$^{-1}$. Addition of water to the mixture required more ionic liquids to keep cellulose dissolved. The highest activity achieved by the synthetic glycosidase was 0.719 $\mu$mol mg$^{-1}$ h$^{-1}$ in 2:8 [$C_2$mim]OAc/DMSO with 5% $H_2O$, several times of the best for cellulases in aqueous buffer at 37° C.

Figures 2A, 2B:
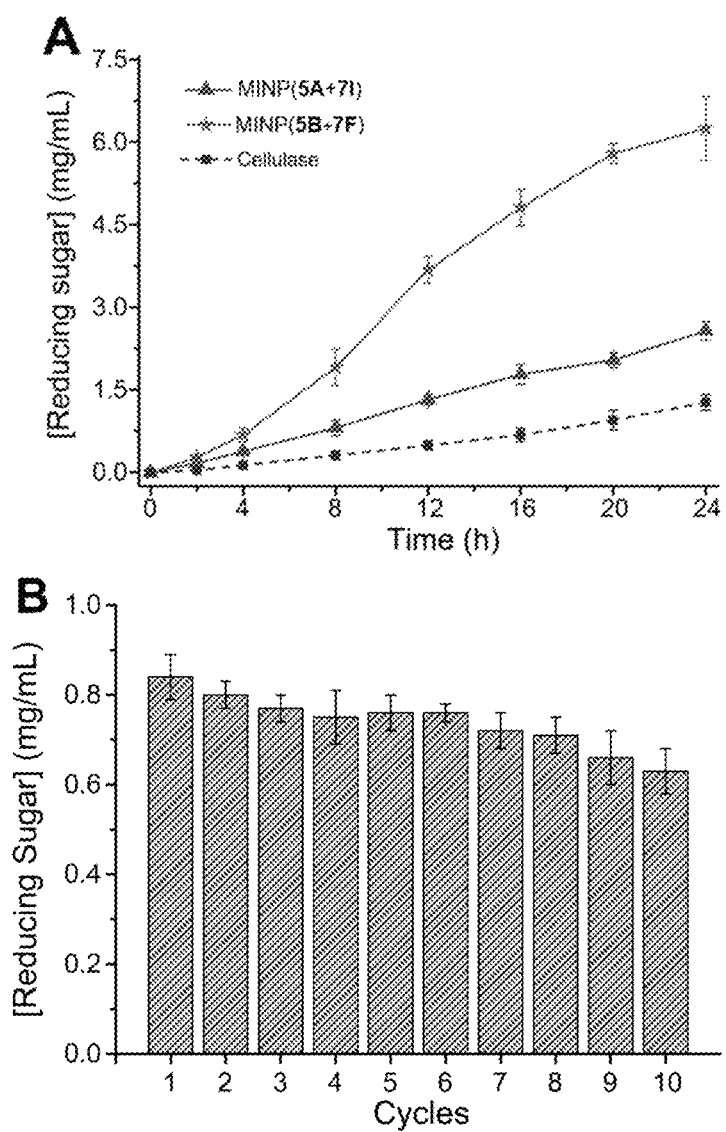
FIG. 2A is the comparison of reducing sugar formed during hydrolysis of cellulose by the synthetic MINP catalysts in 2:8 [$C_2$mim]OAc/DMSO with 5% $H_2O$ at 90° C. and natural cellulase in NaOAc buffer pH 5.0 at 37° C. [cellulose]=8 mg/mL, [catalyst]=2 mg/mL.
FIG. 2B is the recyclability of MINP(5B+7F)@MNP for cellulose hydrolysis in 2:8 [$C_2$mim]OAc/DMSO with 5% $H_2O$ at 90° C.

FIG. 2A shows the amount of reducing sugar formed over a period of 24 h at 90° C. from monoacidic and diacidic catalysts. The reaction profile for the cellulase from *Aspergillus niger* in aqueous buffer at 37° C. was also included for comparison. The MINP catalysts maintained their activity very well over the extended period of heating.

Figures 33A, 33B, 33C, 33D, 33E, 33F:
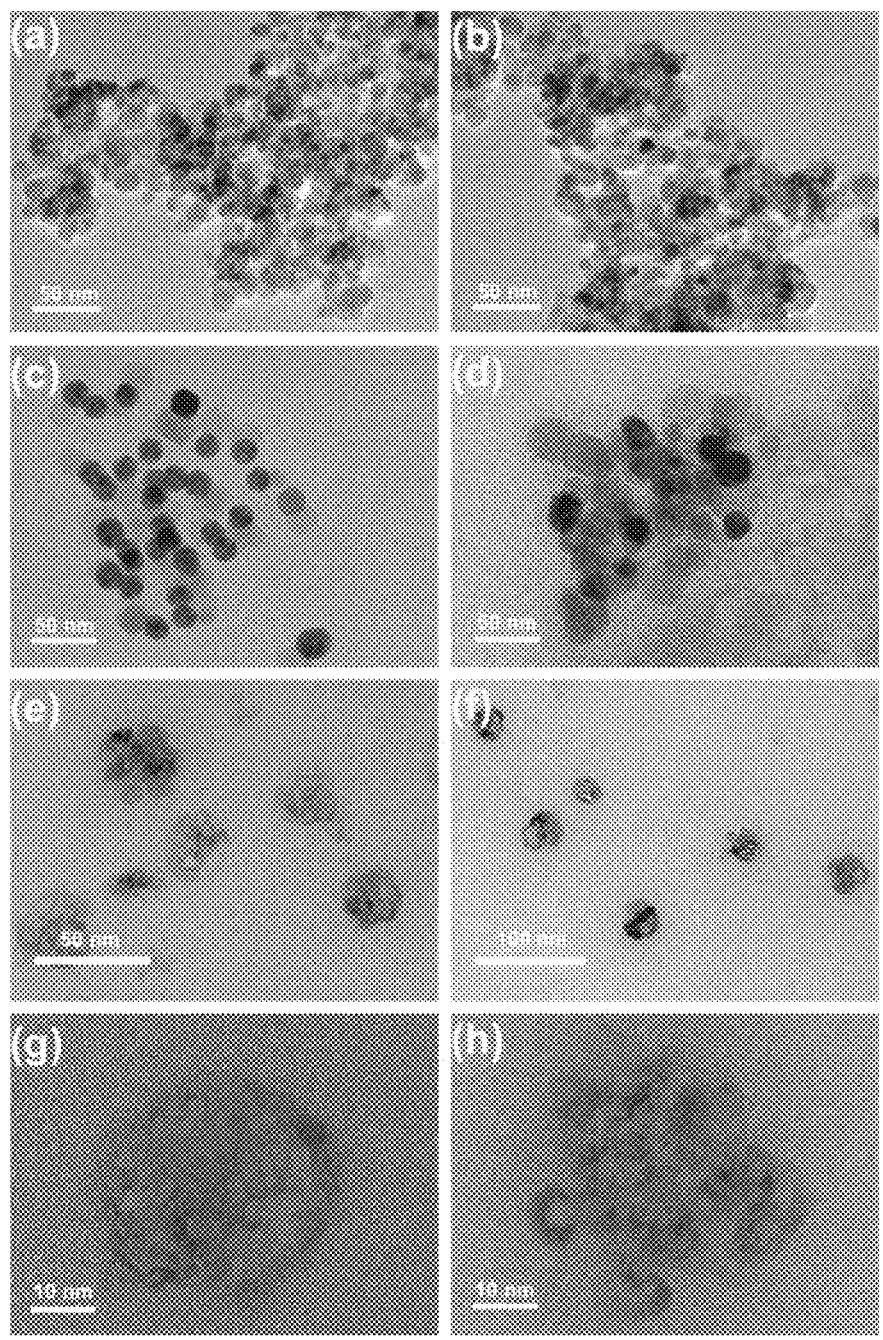
FIGS. 33A and 33B are TEM images of Fe$_3$O$_4$ magnetic nanoparticles.
FIGS. 33C and 33D are TEM images of NH$_2$-MNP.
FIGS. 33E and 33F are TEM images of the final MINP (5B+7F)@MNP.

The surface-core doubly cross-linked micelles are typically covered with monoazide 3 for enhanced hydrophilicity and facile purification (FIG. 1A). Without the termination, the alkyne-containing MINPs could be easily "clicked" onto azide-functionalized magnetic nanoparticles (MNPs) prepared via a literature procedure (Lin, P.-C.; Chou, P.-H.; Chen, S.-H.; Liao, H.-K.; Wang, K.-Y.; Chen, Y.-J.; Lin, C.-C. Ethylene Glycol-Protected Magnetic Nanoparticles for a Multiplexed Immunoassay in Human Plasma. *Small* 2006, 2, 485-489). The resulting MINP(5B+7F)@MNP composite (FIG. 33) was used to hydrolyze cellulose to test the reusability of the catalyst. After each hydrolytic cycle, a magnet was used to retain the heterogeneous catalyst while decanting the solution to analyze the amount of sugar formed. FIG. 2B shows that the catalyst maintained 75% of its activity after 10 cycles of hydrolysis.

Controlled Hydrolysis of Oligosaccharides and Polysaccharides

MINP could be designed to hydrolyze a block of sugar from a glycan using templates such as 5C and 5D (FIG. 1B). Having an acidic group near the exocyclic oxygen of a particular glycosidic bond while recognizing the adjacent sugar residues with reversible boronate ester and hydrogen bonds, these synthetic glycosidase enabled highly controlled hydrolysis of oligosaccharides in water or weakly acidic buffer (pH 6).

MINP(5A+7A-F) could bind the terminal glucose at the nonreducing end of maltose (or other glucose-terminated glycan), with a carboxylic acid near the exocyclic oxygen of the first glycosidic bond (FIG. 1). Table 6 shows that these synthetic catalysts hydrolyzed maltose simply in hot water, without any other additives.

TABLE 6

Hydrolysis of maltose in water catalyzed by MINPs.[a]

| Entry | catalysts | temp (° C.) | time (h) | yield (%) |
|---|---|---|---|---|
| 1 | MINP(5A + 7A) | 60 | 24 | 54 |
| 2 | MINP(5A + 7B) | 60 | 24 | 17 |
| 3 | MINP(5A + 7C) | 60 | 24 | 70 |
| 4 | MINP(5A + 7D) | 60 | 24 | 70 |
| 5 | MINP(5A + 7E) | 60 | 24 | 31 |
| 6 | MINP(5A + 7F) | 60 | 24 | 13 |
| 7 | 7D | 60 | 24 | <1 |
| 8 | NINP[b] + 7D | 60 | 24 | 0 |
| 9 | none | 60 | 24 | 0 |

[a]Reactions were performed in duplicates with 0.2 mM of maltose and 20 μM of MINP in 1.0 mL water. Yields were determined by LC-MS using calibration curves generated from authentic samples.
[b]NINP was nonimprinted nanoparticle prepared without any template and postmodification.

Linear amino-terminated acids 7B-F in the postmodification were also screened, under the hypothesis that flexibility of the acidic group might be beneficial to the catalysis. Indeed, although MINP(5A+7B) was very inactive, MINP (5A+7C/D) gave a much higher yield (70%) in maltose hydrolysis (Table 6). Accurate positioning of the acidic group helped to achieve the hydrolysis, as too short or too long a spacer in the amino acid diminished the yield. Controlled experiments showed that 7D or 7D in combination with nonimprinted nanoparticles (NINPs) failed to hydrolyze maltose under our experimental conditions.

Figure 3:
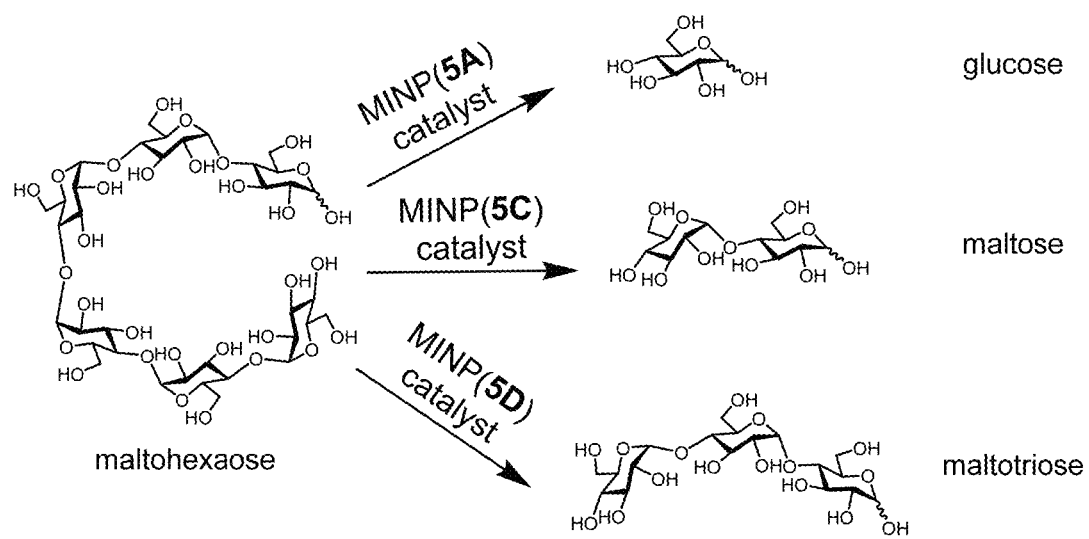
FIG. 3 is the selective hydrolysis of maltohexaose by MINPs.

Two other MINPs were then prepared using 5C and 5D, following similar procedures illustrated in FIG. 1B. Since the corresponding MINPs were intended to bind maltose and maltotriose, respectively, the goal was to hydrolyze maltohexaose in a controlled fashion (FIG. 3).

Table 7 shows the hydrolysis of maltohexaose in water under the standard conditions (60° C. for 24 h). Hydrolysis in buffer at pH 5.5-7.5 was studied and it was found that the reaction yield in water was close to the highest yield obtained at pH 6.

TABLE 7

Hydrolysis of maltohexaose (G6) in water catalyzed by MINPs.[a]

| Entry | catalysts | temp (° C.) | time (h) | glucose (μM) | maltose (μM) | maltotriose (μM) |
|---|---|---|---|---|---|---|
| 1 | MINP(5A + 7D) | 60 | 24 | 106 | 24 | 31 |
| 2 | MINP(5A + 7H) | 60 | 24 | 199 | 17 | 21 |
| 3 | MINP(5A + 7I) | 60 | 24 | 253 | 12 | 42 |
| 4 | MINP(5C + 7D) | 60 | 24 | 11 | 117 | 14 |
| 5 | MINP(5C + 7H) | 60 | 24 | 10 | 127 | 9 |
| 6 | MINP(5C + 7I) | 60 | 24 | 6 | 144 | 7 |
| 7 | MINP(5D + 7D) | 60 | 24 | 7 | 8 | 64 |
| 8 | MINP(5D + 7H) | 60 | 24 | 7 | 10 | 74 |
| 9 | MINP(5D + 7I) | 60 | 24 | 14 | 17 | 98 |

[a]MINPs were prepared with surfactants 1 and 2. Reactions were performed with 0.1 mM maltohexaose and 20 μM of MINP in 1.0 mL water. Yields were determined by LC-MS using calibration curves generated from authentic samples.

In Table 7, the acidity of the acid catalyst was varied, using 7D, 7H, and 7I, respectively, in the postmodification. The yield of the intended products—i.e., glucose from MINP(5A+7D,H,I), maltose from MINP(5C+7D,H,I), and maltotriose from MINP(5D+7D,H,I)-correlated positively with the increased acidity, whereas the unintended hydrolytic products showed less clear trends.

Figure 4:
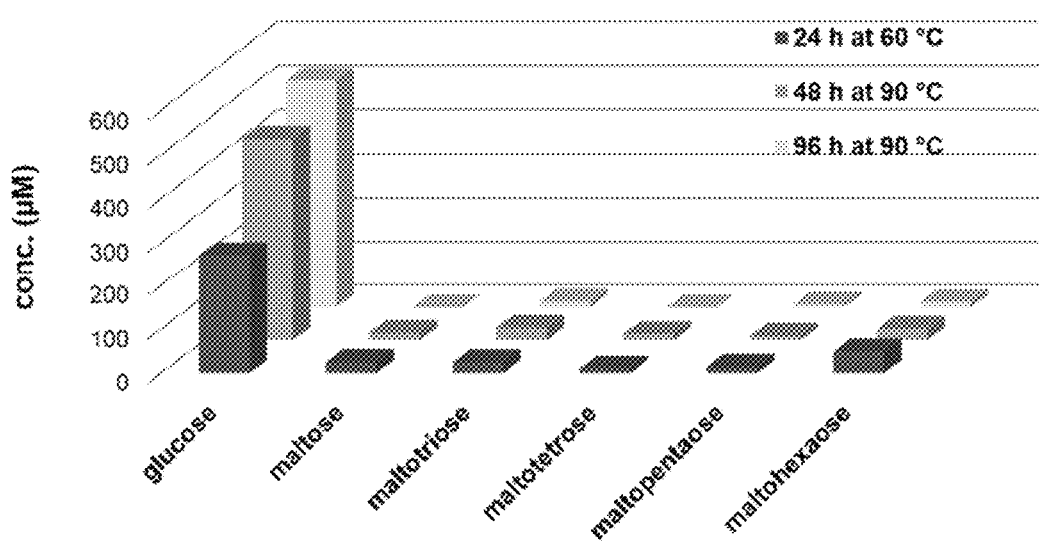
FIG. 4 is the product distribution for the hydrolysis of 100 µM maltohexaose under different conditions by 20 µM MINP(5A+7I) in 10 mM MES buffer (pH 6).
Figure 5:
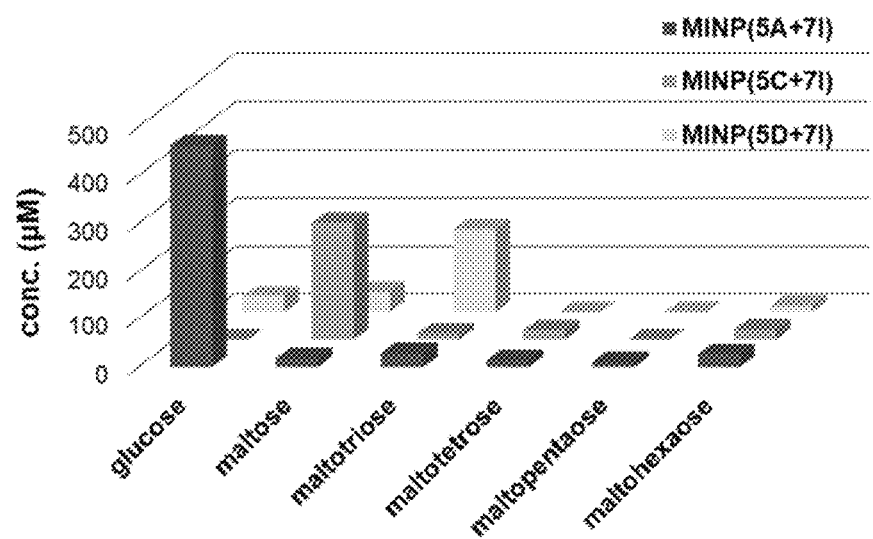
FIG. 5 is the product distribution for the hydrolysis of 100 µM maltohexaose by different MINPs (20 µM) in 10 mM MES buffer (pH 6) at 90° C. for 48 h.

Full characterization of the hydrolyzed products was performed, including longer fragments and the starting material in the LC-MS study (Table 8). FIG. 4 shows distribution of the products catalyzed by MINP(5A+7I). The theoretical yield of glucose was 600 μM from 100 μM maltohexaose. As shown in Table 8, the yield of glucose increased from 45% (24 h at 60° C.) to 77% (48 h at 90° C.) and finally to 86% (96 h at 90° C.). Most importantly, when the three MINPs were used to hydrolyze maltohexaose, the dominant product was always the intended sugar, in a yield of 77%, 82%, and 88% for glucose, maltose, and maltotriose, respectively (FIG. 5).

TABLE 8

Hydrolysis of maltohexaose in MES buffer (pH = 6.0) catalyzed by MINPs.[a]

| | | | | Product Concentration (μM) [b] | | | | | |
|---|---|---|---|---|---|---|---|---|---|
| Entry | MINP[c] | Temp. (° C.) | Time (h) | glucose | maltose | malto-triose | malto-tetraose | malto-pentaose | malto-hexaose |
| 1 | MINP(5A + 7I) | 60 | 24 | 271 | 25 | 24 | 10 | 14 | 49 |
| 2 | MINP(5A + 7I) | 90 | 48 | 462 | 17 | 29 | 14 | 10 | 25 |
| 3 | MINP(5A + 7I) | 90 | 96 | 518 | trace [b] | 14 | trace [b] | 7 | 13 |
| 4 | MINP(5C + 7I) | 60 | 24 | trace [b] | 157 | 7 | 31 | trace [b] | 55 |
| 5 | MINP(5C + 7I) | 90 | 48 | trace [b] | 245 | 12 | 18 | trace [b] | 21 |
| 6 | MINP(5D + 7I) | 60 | 24 | 14 | 17 | 98 | trace [b] | trace [b] | 48 |
| 7 | MINP(5D + 7I) | 90 | 48 | 35 | 45 | 175 | trace [b] | trace [b] | 13 |

[a]MINPs were prepared with surfactants 1 and 2. Reactions were performed in duplicates at 0.1 mM maltohexaose and 20 μM MINP in 1.0 mL buffer. Yields were determined by LC-MS using calibration curves generated from authentic samples. Typically, estimated errors of product concentration were ±20%.
[b] The product concentration <1 μM.

Another interesting observation in the hydrolysis was that the MINP catalysts hydrolyzed the intermediate products faster than the substrate. For example, whether at moderate (~50%) or higher (>80%) conversion, the intermediate products were insignificant in comparison to the desired products (FIGS. 4 and 5). One possible reason for the results was that these curved oligosaccharides (with the α-1,4-glycosidic linkages) might experience steric hindrance in binding with the MINP—the longer the chain, the larger the hindrance. Consistent with this postulation, isothermal titration calorimetry (ITC) showed that the binding constant ($K_a$) of glucose for MINP-CHO(5A) was $(8.85+0.68) \times 10^3$ $M^{-1}$ and decreased steadily in the order of glucose>maltose>maltotriose>maltohexaose (Table 2).

The $K_m$ value of MINP(5A+7I) for maltose was about half of that for maltohexaose, indicating the catalyst bound maltose more strongly (Table 9). The catalytic turnover ($k_{cat}$) for maltose also doubled that for maltohexaose. The catalytic efficiency ($k_{cat}/K_m$) of the MINP for maltose was thus more than 4 times higher than that for maltohexaose. These results supported the above explanation for the "absence" of intermediate products in the hydrolysis of maltohexaose by MINP(5A+7I).

TABLE 9

Michaelis-Menten Parameters for the MINPs in the hydrolysis of maltose and maltohexaose.[a]

| entry | MINP | substrate | $V_{max}$ (μM/min) | $K_m$ (μM) | $k_{cat}$ ($\times 10^{-3}$ $min^{-1}$) | $k_{cat}/K_m$ ($M^{-1}$ $min^{-1}$) |
|---|---|---|---|---|---|---|
| 1 | MINP(5A + 7I) | maltose | 0.37 ± 0.01 | 336 ± 25 | 18.26 | 54.1 |
| 2 | MINP(5A + 7I) | maltohexaose | 0.17 ± 0.01 | 691 ± 90 | 8.70 | 12.6 |
| 3 | MINP(5C + 7I) | maltohexaose | 0.19 ± 0.01 | 541 ± 39 | 9.36 | 16.5 |
| 4 | MINP(5D + 7I) | maltohexaose | 0.20 ± 0.01 | 474 ± 24 | 9.92 | 19.5 |

[a]Reaction rates were measured in water at 60° C., based on the disappearance of the reactant. [MINP] = 20 μM.

For the hydrolysis of maltohexaose, the three MINP catalysts showed similar $k_{cat}$ but stronger binding for the substrate—i.e., $K_m$ decreased in the order of MINP(5A+7I)>MINP(5C+7I)>MINP(5D+7I) (Table 9). The trend was similar to what was observed in the ITC-determined binding constants for the corresponding sugars (Table 2). Both should be derived from a larger binding interface of a longer sugar with its complementary imprinted binding site. Not only could the substrate form more hydrogen bonds with the amides of (cross-linked) 1 in the MINP, more water molecules in the active site would also be released during binding A result from the stronger binding of the shorter sugars was product inhibition. With MINP being much larger than the sugars and the staring material (maltohexaose) also larger than the desired products (glucose, maltose, and maltotriose), product inhibition could be overcome simply by performing the hydrolysis inside a dialysis membrane that was permeable to the desired product but impermeable to the starting material and the catalyst. In this way, the starting material and the MINP catalyst would stay inside the membrane during hydrolysis, and the product would escape into the bulk solution. Diluting the concentration of the product inside the membrane (e.g., by ~40 times under the dialysis conditions) would reduce or eliminate product inhibition. In addition, the product would be isolated in situ from the starting material and the catalyst, greatly simplifying the purification of the product and reuse of the catalyst.

Figures 6A, 6B, 6C:
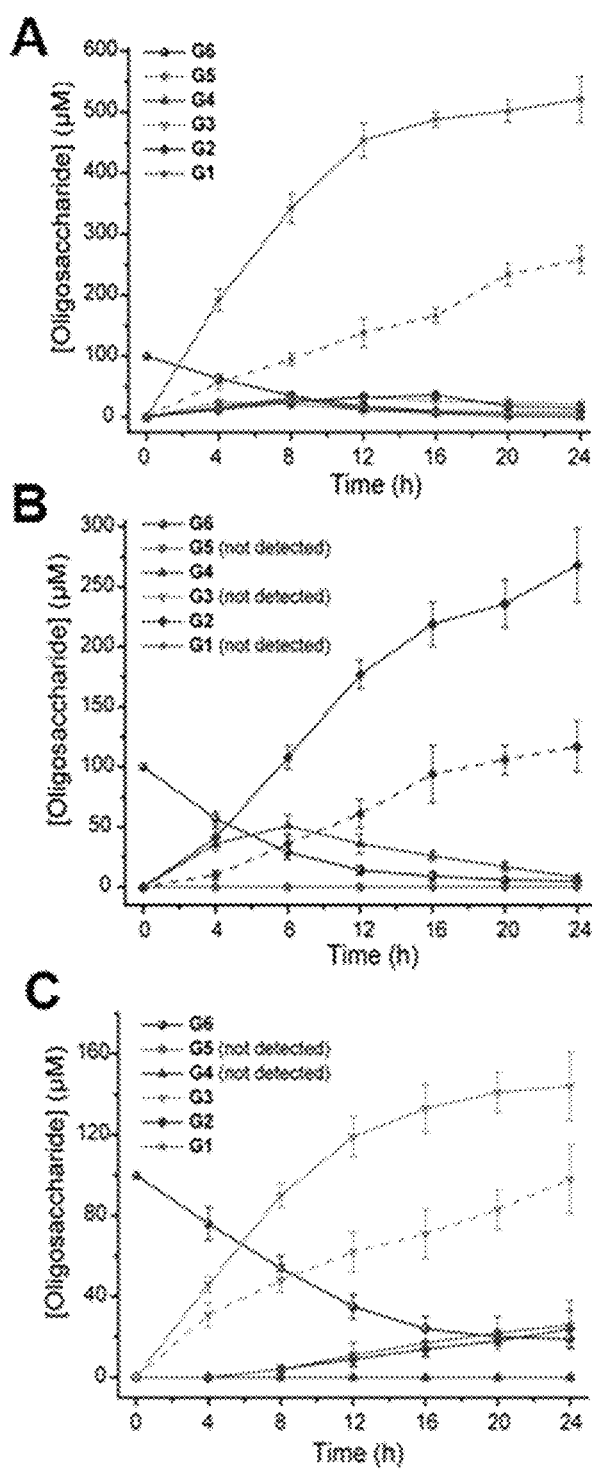
FIG. 6A is the production distribution over time for the hydrolysis of 100 µM maltohexaose by 20 µM MINP(5A+ 7I) at 60° C. in $H_2O$, with the reaction mixture (1.0 mL) dialyzed against 40 mL of Millipore water using a membrane (MWCO=500). The points connected by dashed lines represent the hydrolysis without dialysis.
FIG. 6B is the production distribution over time for the hydrolysis of 100 µM maltohexaose by 20 µM MINP(5C+7I) at 60° C. in H$_2$O, with the reaction mixture (1.0 mL) dialyzed against 40 mL of Millipore water using a membrane (MWCO=500). The points connected by dashed lines represent the hydrolysis without dialysis.
FIG. 6C is the production distribution over time for the hydrolysis of 100 µM maltohexaose by 20 µM MINP(5D+7I) at 60° C. in H$_2$O, with the reaction mixture (1.0 mL) dialyzed against 40 mL of Millipore water using a membrane (MWCO=500). The points connected by dashed lines represent the hydrolysis without dialysis.

A dialysis tubing with a MW-cutoff (MWCO) of 500 Da was chosen to test the hypothesis. The membrane was selected to allow glucose (MW 180) and maltose (MW 342) to easily escape but to retain maltotriose to a certain extent (MW 504). It was found that hydrolysis of maltohexaose into glucose, maltose, and even maltotriose all improved significantly with the catalysis performed inside the dialysis membrane. The improvements can be seen by comparing the solid and dashed lines in FIG. 6A-C. At the end of 24 h, the yields of the desired product increased from 43% to 87% for glucose, 39% to 89% for maltose, and 49% to 72% for maltotriose. The stronger benefits of dialysis on glucose and maltose over maltotriose supported the experimental hypothesis, since maltotriose (MW 504) was very close to the MWCO of the membrane.

A rich source of polysaccharides is found in nature. Their precise cleavage based on the selective one-step hydrolysis can be a convenient and economical way to produce glycans that otherwise require complex multistep synthesis and extensive protective/deprotective chemistry.

Figure 7:
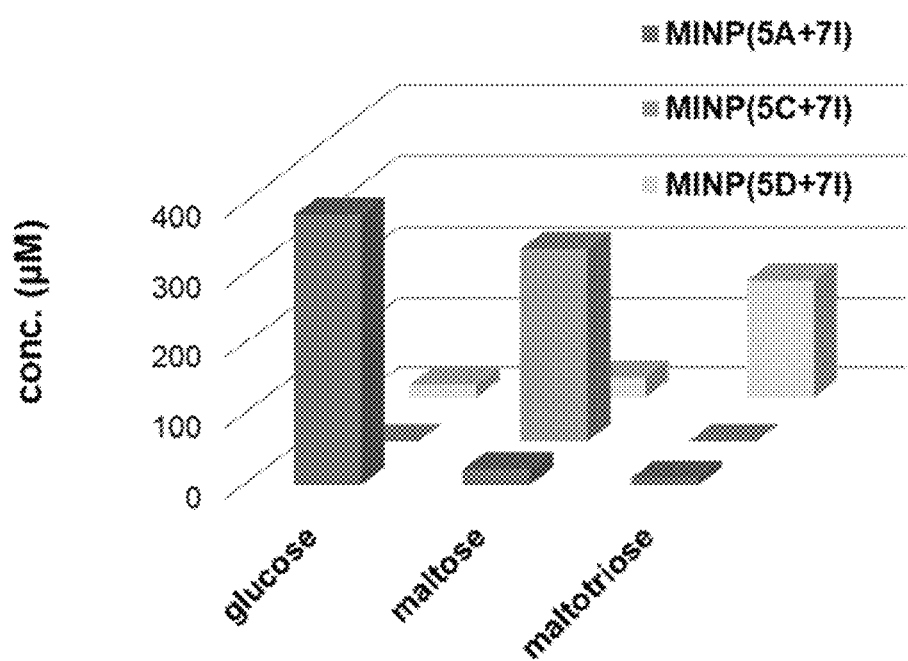
FIG. 7 is the product distribution in the hydrolysis of amylose by the MINP catalysts after 24 h at 60° C. in H$_2$O, with the reaction mixture (1.0 mL) dialyzed against 40 mL of deionized water using a membrane (MWCO=500). [Amylose]=1 mg/mL, [MINP]=20 µM.

Indeed, not only could these MINP glycosidases hydrolyze maltohexaose in a highly controlled fashion, they could also hydrolyze amylose, a polysaccharide of glucose connected by the same 1,4-α-glycosidic linkage, with equally good selectivity (FIG. 7). The hydrolysis once again was performed inside the dialysis membrane, with the polysaccharide and MINP catalysts trapped inside and the product released into the bulk solution.

Figure 8:
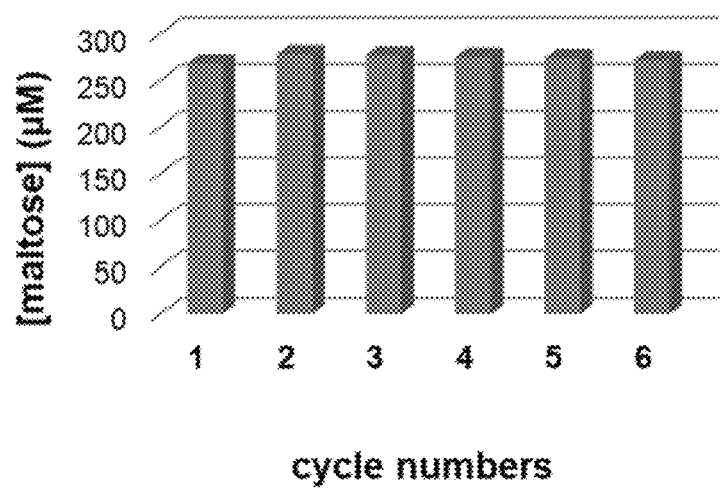
FIG. 8 is the recyclability of MINP(5C+7I) in maltohexaose hydrolysis. [maltohexaose]=100 µM. [MINP]=20 µM.

Another benefit of performing the hydrolysis inside a dialysis membrane was the facile recycling of the catalyst. As a highly cross-linked polymeric nanoparticles, the MINP-based artificial glycosidase could be reused many times with very little loss of activity when maltohexaose was repeatedly added into the dialyzing tubing that contained MINP(5C+7I) (FIG. 8).

Substrate selectivity can be an important performance criteria for a synthetic glycosidase, since different building blocks, connection sites, and spatial orientation of the glycosidic linkage can influence the property of a glycan profoundly. Table 10 shows the hydrolysis of several oligosaccharides by the MINP catalysts. The yields were for the hydrolysis at 60° C. after 24 h and the binding constants were for the same MINP determined by ITC at 25° C.

TABLE 10

Hydrolysis of oligosaccharides by MINP catalysts.[a]

| | | |
|---|---|---|
| hydrolytic yield by MINP (5A + 7I)<br>$K_a$ by MINP (5A + 7I) | maltose<br>82%<br>7990 M$^{-1}$ | cellobiose<br>67%<br>1880 M$^{-1}$ |
| hydrolytic yield by MINP (5A + 7I)<br>$K_a$ by MINP (5A + 7I) | sucrose<br>49%<br>1830 M$^{-1}$ | maltulose<br>47%<br>2990 M$^{-1}$ |
| hydrolytic yield by MINP (5A + 7I)<br>$K_a$ by MINP (5A + 7I) | lactose<br>17%<br>200 M$^{-1}$ | xylobiose<br>0%<br><50 M$^{-1}$ |
| hydrolytic yield by MINP (5A + 7I)<br>$K_a$ by MINP (5A + 7I)<br>hydrolytic yield by MINP (5C + 7I)<br>$K_a$ by MINP (5C + 7I) | maltotriose<br>71% (for glucose)<br>5620 M$^{-1}$<br>85% (for maltose)<br>11500 M$^{-1}$ | |
| hydrolytic yield by MINP (5A + 7I)<br>$K_a$ by MINP (5A + 7I)<br>hydrolytic yield by MINP (5C + 7I)<br>$K_a$ by MINP (5C + 7I) | cellotriose<br>54% (for glucose)<br>2620 M$^{-1}$<br>24% (for cellobiose)<br>3640 M$^{-1}$ | |

[a]The hydrolysis experiments were performed at 60° C. in water for 24 h, with [oligosaccharide] = 0.2 mM and [MINP] = 20 μM. Yields were determined by LC-MS using calibration curves generated from authentic samples.

Consistent with the binding-derived catalysis, there was an overall correlation between the hydrolytic yields and the $K_a$ values. For example, among the disaccharides, maltose gave the best yield with MINP(5A+7I) and its binding was also the strongest. Xylobiose was completely inactive and its binding was also the weakest. For the sugars with intermediate binding constants (cellobiose, sucrose, and maltulose), the correlation was weak.

Another conclusion from the hydrolyses was the importance of the boronate ester formation to the substrate selectivity. MINP(5A+7I) was designed to bind the terminal glucose of a suitable oligo- or polysaccharide at the non-reducing end. Cellobiose, sucrose, and maltulose could all be hydrolyzed by this MINP. The reducing sugar residue on these molecules is expected to reside in water, outside the active site. For the same reason, MINP(5A+7I) should not be particularly selective for the reducing sugar, whether in its chemical structure or spatial orientation. Meanwhile, MINP(5A+7I) should be much more selective toward the sugar at the nonreducing end, especially if the hydroxyl involved in boronate formation is altered. Lactose, with a galactose at the non-reducing end, gave a very poor hydrolytic yield and binding constant, because its C4 hydroxyl was mismatched for boronate formation. Inversion of a single hydroxyl decreased the yield of hydrolysis from 67% for cellobiose to 17% for lactose. Xylobiose is missing the hydroxymethyl from cellobiose. Its inactivity indicates that the C6 hydroxyl was also important to the binding.

For a monosaccharide-derived catalyst such as MINP (5A+7I), its only selectivity was in the terminal sugar at the non-reducing end and the α/β selectivity was low. For a disaccharide-derived catalyst, the situation was different because the α/β linkage between the first two sugar residues would affect the binding of the substrate.

MINP(5A+7I) can hydrolyze maltotriose and cellotriose into glucose. Table 10 shows that the yield of glucose was 71% and 54% from the two trisaccharides, respectively. The α/β selectivity (1.3:1) was slightly higher than that observed in maltose/cellobiose (1.2:1), possibly because two hydrolyses were needed to hydrolyze the trisaccharides but only one for the disaccharides, which magnified the α/β selectivity. When MINP(5C+7I) was used, however, the yield for the desired (disaccharide) product was 85% from maltotriose and only 24% from cellotriose. This was because the imprinted site was designed to bind maltose in this catalyst. Thus, the β glycosidic bond between the first and second sugar from the nonreducing end of cellotriose would weaken the binding of this substrate.

Micellar imprinting provided a rational method to construct robust synthetic glycosidases from readily synthesized small-molecule templates. Natural glucan 1,4-alpha-glucosidase removes one glucose residual at a time from the nonreducing end of amylose, and from beta-amylase two glucose residues (i.e., maltose) at a time. The synthetic glycosidase not only duplicated the selectivities of these enzymes but also had selectivity not available from natural biocatalysts—i.e., selective formation of maltotriose from maltohexaose or amylose. Substrate selectivity was mainly determined by the sugar residues bound within the active site, including their spatial orientation.

Importantly, the design of the synthetic glycosidase is general, using molecular imprinting to create a glycan-specific active site, followed by postmodification to install an acidic group next to the glycosidic bond to be cleaved. Similar designs could be applicable to complex glycans. Total synthesis of carbohydrates is extremely challenging. Selective, one-step hydrolysis by a rationally designed synthetic glycosidase can potentially be a powerful method to produce complex glycans from precursor oligosaccharides or polysaccharides either naturally available or prepared through enzymatic synthesis. Facile separation of product by dialysis, excellent reusability of the MINP catalysts, and simplicity of the hydrolysis (e.g., that requires only hot water) are attractive features for such a purpose, and can open up new avenues in glycoscience and technology.

Catalytic Hydrolysis of Glycans by Noncovalently Bound Acid Catalysts

Figure 9:
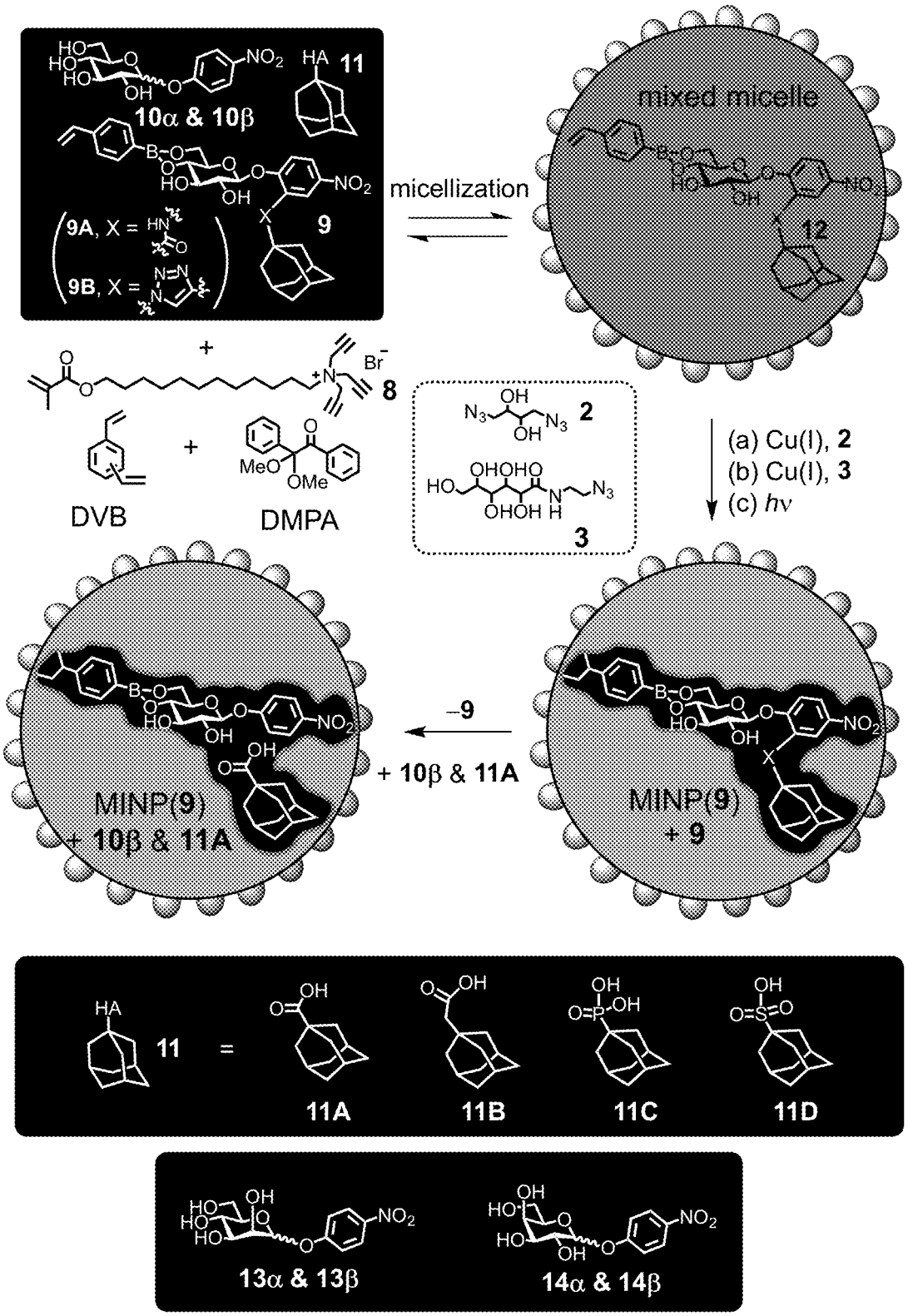
FIG. 9 is the preparation of artificial glucosidase MINP(9) by micellar imprinting. The surface ligands are omitted from the drawing for clarity.

FIG. 9 shows the synthesis of a MINP-based catalyst to hydrolyze a glycan by a noncovalently bound acid catalyst, using compound 8 as the cross-linkable surfactant. The hydrophobic boronate 9 was essentially a template-functional monomer (FM) complex, which was designed to yield three features in the MINP: a substrate-shaped binding site, a diol-binding boronic acid group, and an adamantane-shaped hydrophobic pocket near the glucose-binding site. Acid cofactor 11 entered the adamantane-binding site through hydrophobic interactions. Compounds 11A-11D allowed the distance of the acidic group to be varied to the bound substrate to a certain extent, as well as the acidity of the catalytic group. The binding site could be tuned additionally through the tether X in the template. The amide linkage in 9A closely resembles the carboxylic acid of 11A in dimension, whereas the triazole of 9B was somewhat larger.

Figure 10:
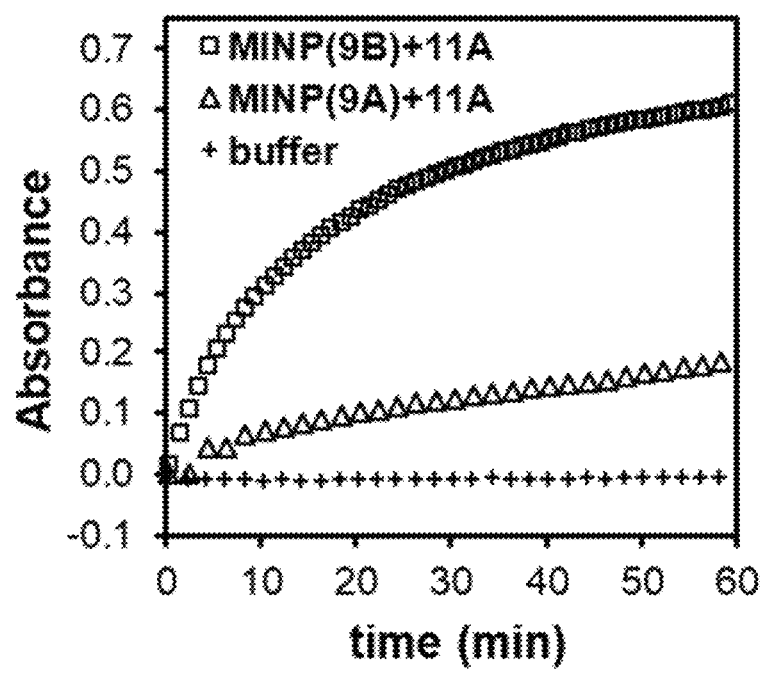
FIG. 10 is the absorbance at 320 nm during the hydrolysis of 10β in a 10 mM MES buffer (pH 6.0), and in the presence of MINP(9A)+11A or MINP(9B)+11A at 40° C.
Figure 11:
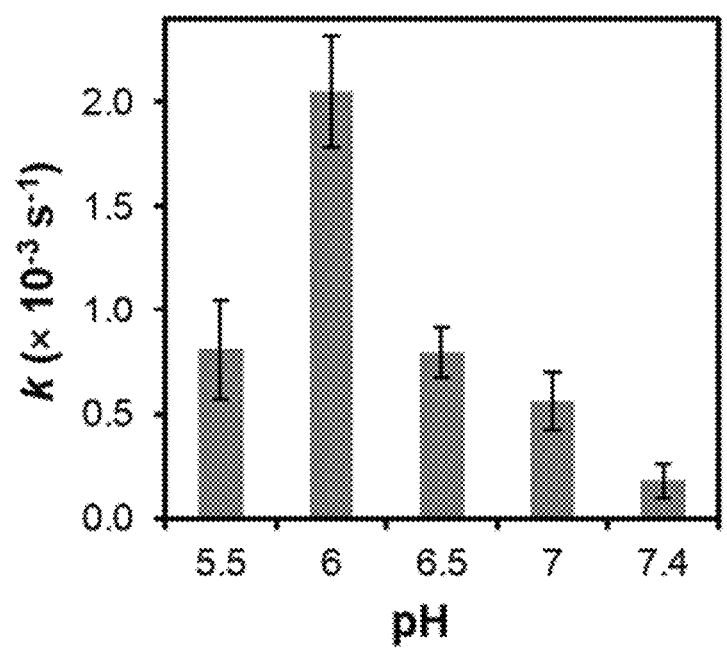
FIG. 11 is the effect of pH on the hydrolysis of 10β catalyzed by MINP(9B)+11A. [10β]=100 µM. [MINP]=5 µM. [11A]=10 µM.

FIG. 10 shows the hydrolysis of p-nitrophenyl β-D-glucopyranoside 10β catalyzed by MINP(9)+11A in pH 6 buffer at 40° C. Background hydrolysis was negligible under the condition and both MINP(9A) and MINP(9B) showed significant activity, with the latter being clearly more efficient. A screening of the different acid cofactors (11A-11D) indicated that an increase of acidity for the cofactor lowered the hydrolytic rates, in the order of 11A>11B>11C>11D (Table 11). For the best catalyst, i.e., MINP(9B)+11A, a pH study showed that the hydrolysis showed a maximum at pH 6 (FIG. 11).

TABLE 11

Pseudo-first-order rate constants for the hydrolysis of 10β and 10α by MINP(9B) with different acid cofactors.[a]

| Entry | Acid cofactor | Substrate | $k_{obs.}$ ($\times 10^{-3}$ s$^{-1}$) | $K_{rel}$ |
|---|---|---|---|---|
| 1 | 11A | 10β | 2.05 | 1 |
| 2 | 11B | 10β | 1.36 | 0.66 |
| 3 | 11C | 10β | 0.36 | 0.18 |
| 4 | 11D | 10β | 0.14 | 0.07 |
| 5 | 11A | 10α | 0.18 | 0.09 |
| 6 | 11B | 10α | 0.12 | 0.06 |

[a]Reaction were performed in 10 mM buffer at pH 6.0 at 40° C. [10β] = 100 μM. [MINP(9B)] = 5 μM. [acid cofactor] = 10 μM.

Table 12 summarizes the binding constants between the two MINPs and the substrate or acid cofactors at pH 6 determined by isothermal titration calorimetry (ITC). Both MINPs were found to have a similar binding for 10β, with $K_a \approx 8 \times 10^4$ M$^{-1}$ in pH 6 MES buffer (entries 1 and 3). The binding constant translated to 88% of the 5 μM MINP catalyst being bound with a substrate at [10β]=100 μM and 39% at [10β]=10 μM. In other words, the majority of the MINP catalyst should have a bound substrate during a large portion of the reaction time. Note that the number of binding site per nanoparticle (i.e., N) determined by ITC was ~1 in all cases, as a result of keeping the surfactant/template ratio close to the surfactant aggregation number of the micelle during MINP preparation.

The more efficient MINP(9B) bound the acid cofactor 11A more strongly than the less efficient MINP(9A), by nearly 9 times (Table 12, entries 3 and 6). These $K_a$ values translated to 51% and 87% of occupancy of MINP(9A) and MINP(9B) by the acid cofactor, respectively, at [MINP]=5 µM and [11A]=10 µM used for the hydrolysis.

TABLE 12

ITC binding data for substrates and acid catalysts.[a]

| Entry | Template | Guest | $K_a$ ($\times 10^4$ M$^{-1}$) | $\Delta G$ (kcal/mol) | N[b] |
|---|---|---|---|---|---|
| 1 | 9A | 10β | 8.24 ± 0.60 | −6.71 | 1.1 ± 0.1 |
| 2 | 9A | 10α | 2.46 ± 0.29 | −5.99 | 1.1 ± 0.1 |
| 3 | 9A | 11A | 14.20 ± 0.44 | −7.02 | 0.9 ± 0.1 |
| 4 | 9B | 10β | 8.59 ± 0.67 | −6.73 | 1.1 ± 0.1 |
| 5 | 9B | 10α | 2.49 ± 0.22 | −5.99 | 1.2 ± 01 |
| 6 | 9B | 11A | 122.0 ± 9.0 | −8.30 | 1.0 ± 0.1 |
| 7 | 9B | 11B | 4.7 ± 3.5 | −8.01 | 1.0 ± 0.1 |
| 8 | 9B | 11C | 36.6 ± 1.4 | −7.58 | 0.9 ± 0.1 |
| 9 | 9B | 11D | 21.4 ± 1.3 | −7.27 | 1.0 ± 0.1 |

[a]The titrations were performed in 10 mMMES buffer at pH 6.0 at 298K.
[b] N is the average number of binding site per nanoparticle measured by ITC curve fitting.

There could be two possible reasons for the stronger binding of MINP(9B) over MINP(9A) for 11A. First, the secondary amide of 9A, being an excellent hydrogen-bond donor and acceptor, could move the templated pocket for the adamantyl group closer to the micellar surface, with its strong solvation by water. The shallower the imprinted pocket for the adamantyl group, the less hydrophobic it would be and the driving force for 11A to enter the pocket would be weaker. Second, the imprinted pocket in MINP (9A) might be too tight for the acid cofactor. Micellar imprinting has been shown to have an extraordinary ability to reproduce structural features of the template. Imprinting factors frequently exceed 100 in comparison to nonimprinted particles, as a result of confining the imprinting (i.e., the templated polymerization/cross-linking) in the nano-sized surface-cross-linked micelle (Table 2). A move of a single methyl by one carbon is easily detected by peptide-template MINPs in their binding of isomeric di- and tripeptides (Awino, J. K.; Gunasekara, R. W.; Zhao, Y. Sequence-Selective Binding of Oligopeptides in Water through Hydrophobic Coding. *J. Am. Chem. Soc.* 2017, 139, 2188-2191).

Not only did the binding of 11A by the two MINPs correlate with the hydrolysis of 10β, the binding of the acid cofactors 11A-11D by MINP(9B) also correlated with hydrolysis (Table 12, entries 6-9: 11A>11B>11C>11D). All the acid cofactors have the same adamantyl hydrophobe and thus should have a similar hydrophobic driving force to enter the imprinted site. However, because a charged group is not solvated well and is unstable in a hydrophobic microenvironment, the acid cofactor has a tendency to enter the MINP in its protonated, neutral state, which was the catalytically active form. Given that all the acids have $pK_a \leq 5$, the deprotonated form would dominate in the pH 6 buffer used for the hydrolysis. If indeed the acid cofactor had to occupy the MINP binding site in the protonated form, a stronger acid would have to pay a higher penalty for the binding than a weaker acid, in agreement with the observed trend (i.e., 11A>11B>11C>11D).

Figure 12:
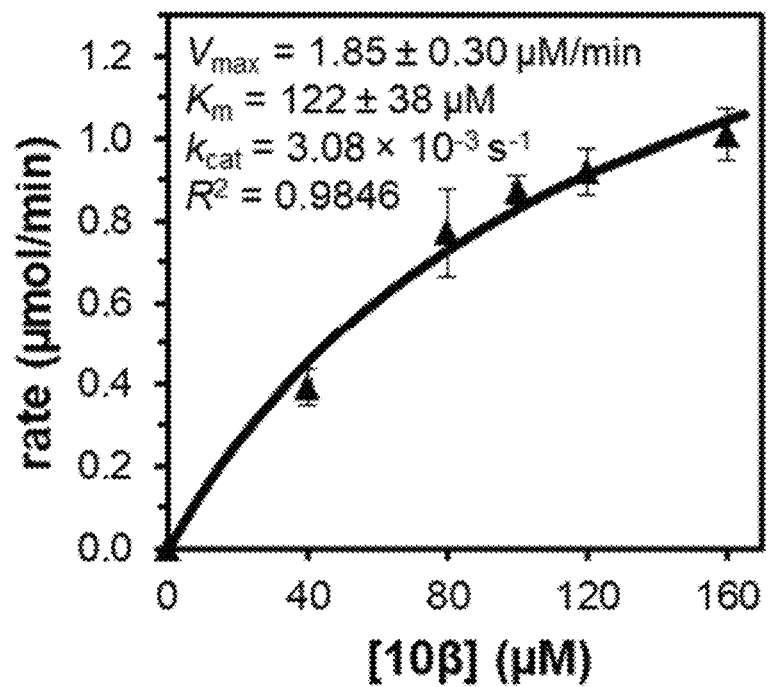
FIG. 12 is the Michaelis-Menten plot for the hydrolysis of 10β by MINP(9B)+11A in a 10 mM MES buffer (pH 6.0) at 40° C. [MINP(9B)]=[11A]=10 µM.
Figure 13:
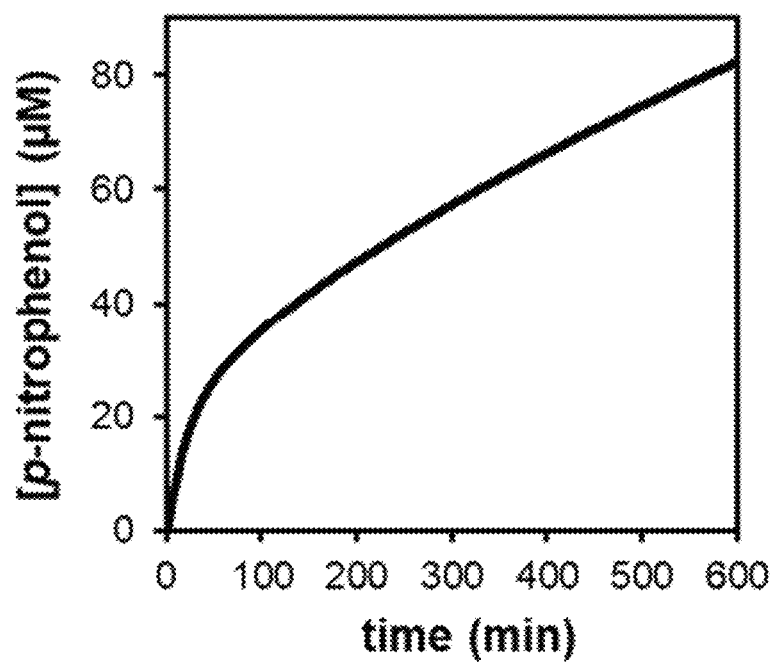
FIG. 13 is the amount of p-nitrophenol formed as a function of time, calculated from an extinction coefficient of $\varepsilon_{320}$=0.0084 µM$^{-1}$ cm$^{-1}$. [MINP(9B)]=[11A]=10 µM.

MINP(9B)+11A exhibited enzyme-like Michaelis-Menten kinetics in its hydrolysis of 10β (FIG. 12). The catalytic efficiency ($k_{cat}/K_m$) was 25.2 M$^{-1}$s$^{-1}$ at pH 6.0 and 40° C. Its catalytic turnover number (TON) was 411 at 600 min when 500 equivalents of substrate were used in the hydrolysis (FIG. 13). The reaction over the prolonged period of time had a fast and a slower phase. Most likely, the slower phase was a result of product inhibition, as both products of hydrolysis—i.e., glucose and p-nitrophenol—are expected to bind the imprinted sites, albeit less strongly than the substrate itself.

Figures 14A, 14B:
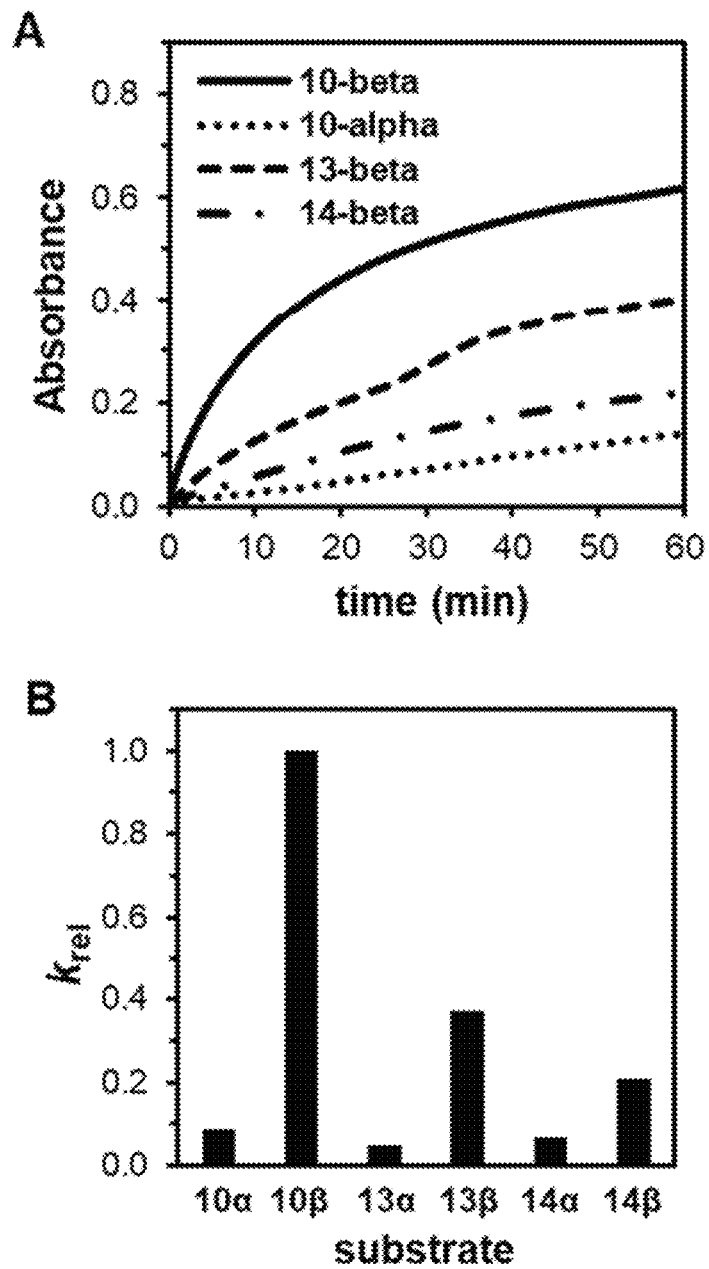
FIG. 14A is the absorbance at 320 as a function of time for the hydrolysis of 10β, 10α, 13β, and 14β catalyzed by MINP(9B)+11A in a 10 mM MES buffer (pH 6.0) at 40° C. [substrate]=100 µM. [MINP]=5 µM. [11A]=10 µM.
FIG. 14B is the rate constants for the hydrolysis of different substrates normalized to that of glucoside 10β.

The selectivity of MINP(9B)+11A (FIG. 14A) was studied. The catalyst favored 10β over 10a by 11.4 times (FIG. 14B), thus able to overcome the higher inherent reactivity of the a anomer to favor the targeted substrate (Sinnott, M.: Chapter 3. Nucleophilic Substitution at the Anomeric Centre. In *Carbohydrate Chemistry and Biochemistry: Structure and Mechanism*; 2nd ed.; RSC Publishing: Cambridge, 2013; pp 88). Among the three β anomers, the order of reactivity observed was glucoside (10β)>mannoside (9β)>galactoside (10β), as shown by FIG. 14B. The trend was in line with the boronic acid-binding, as the mannoside had the same trans-4,6-diol as the targeted substrate (10β) whereas the galactoside did not. Meanwhile, all three a anomers exhibited similar reactivities and were significantly less reactive than the β substrates overall.

Hydrolysis of Cellulose in Water

Figure 15:
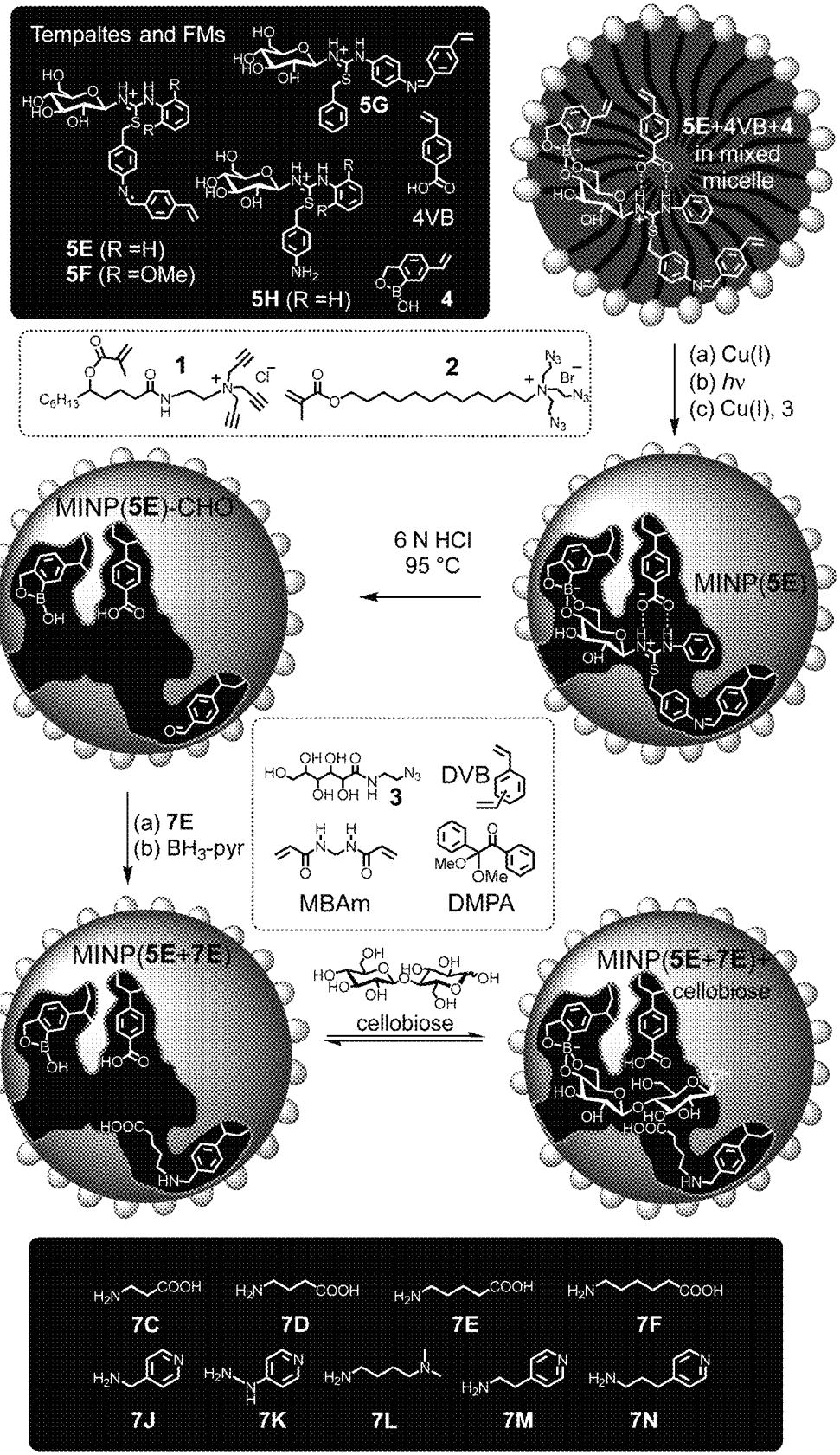
FIG. 15 is the preparation of artificial glucosidase MINP (5E+7E) by micellar imprinting. The surface ligands are omitted from the drawing for clarity.

Natural glycosidases generally use a pair of carboxylic acids for the hydrolysis. MINP, however, can be designed to have different catalytic groups using templates 5E-5G (FIG. 15). These templates make it possible to introduce two catalytic groups independently. As a result, either the biomimetic dicarboxylic acid or an acid-amine catalytic dyad can be installed in the active site.

The design of these templates is based on four considerations. First, their glucosyl group represents part of the substrate—i.e., the glucose from the nonreducing end of a cellulose chain (cellobiose shown in FIG. 15 for simplicity). The hydrogen-bonded salt bridge between the thiouronium group of the template and 4-vinylbenzoic acid (4VB) enables a carboxylic acid to be introduced near the exocyclic glycosidic oxygen of this glucose after polymerization. Second, the template contains an imine moiety with a polymerizable vinyl group in the aglycon. After polymerization/cross-linking of the micelle, the imine bond can be hydrolyzed in 6 N HCl and postfunctionalized through reductive amination. This method allows either an acidic or a basic group to be installed near the glycosidic bond as the second catalytic group, using functional amine derivatives 7C-F or 7J-N, respectively. Third, the amphiphilicity of the template-FM complex helps the complex stay at the surfactant/water interface. This "hydrophilic anchoring" ensures that the final imprinted site will be close to the micelle surface, a feature beneficial to the template removal, postmodification of the imprinted site, and binding of the substrate in the catalysis. Fourth, all these templates are modularly synthesized. A simple change in reagents allow the size and shape of the space to be varied near the catalytic groups, as well as the orientation of the second catalytic group (whether acidic or basic) relative to the first one introduced through 4VB.

Table 13 summarizes the hydrolysis of cellobiose by the MINP catalysts. The catalytic hydrolysis was clearly dependent on the length of tether in 7C-F that controlled the relative distance between the first and the second carboxylic acids (Table 13, entries 1-4). The results support that the second catalytic group was successfully installed in the catalysts. Among the dicarboxylic acid-functionalized MINPs, MINP(5E+7E) was the best and gave a 66% yield for the cellobiose hydrolysis at a 10 mol % catalyst loading.

TABLE 13

Hydrolysis of cellobiose catalyzed by MINPs at 60° C. in 10 mM MES buffer (pH 6).[a]

| entry | catalysts | 4VB | DVB/MBAm | yield (%) |
|---|---|---|---|---|
| 1 | MINP(5E + 7C) | 1 | 1/0 | 17 ± 2 |
| 2 | MINP(5E + 7D) | 1 | 1/0 | 47 ± 4 |
| 3 | MINP(5E + 7E) | 1 | 1/0 | 66 ± 8 |
| 4 | MINP(5E + 7F) | 1 | 1/0 | 52 ± 9 |
| 5 | MINP(5E + 7E) | 0 | 1/0 | 38 ± 6 |
| 6 | MINP(5E + 7E) | 1 | 1/1 | 47 ± 4 |
| 7 | MINP(5E + 7E) | 1 | 1/2 | 39 ± 6 |
| 8 | MINP(5E + 7E) | 1 | 2/1 | 71 ± 4 |
| 9 | MINP(5E + 7E) | 1 | 3/1 | 72 ± 4 |
| 10 | MINP(5F + 7E) | 1 | 3/1 | 62 ± 4 |
| 11 | MINP(5G + 7E) | 1 | 3/1 | 78 ± 4 |
| 12 | MINP(H + 4VB)[b] | 1 | 3/1 | 10 ± 4 |
| 13 | 4VB | — | — | 0 |
| 14 | 7E | — | — | <2 |
| 15 | NINP[c] + 4VB + 7E | — | 1/0 | <2 |
| 16 | MINP(5E + 7J) | 1 | 3/1 | 41 ± 4 |
| 17 | MINP(5E + 7K) | 1 | 3/1 | 51 ± 6 |
| 18 | MINP(5E + 7L) | 1 | 3/1 | 47 ± 4 |
| 19 | MINP(5E + 7M) | 1 | 3/1 | 61 ± 4 |
| 20 | MINP(5E + 7N) | 1 | 3/1 | 42 ± 3 |

[a]Reactions were performed with 0.2 mM of cellobiose and 20 μM of catalysts in 1.0 mL MES buffer (10 mM, pH = 6.0) for 24 h. Yields were determined by LC-MS using standard curves generated from authentic samples.
[b]The acidic group of the catalyst came from 4VB added in the MINP preparation and no postfunctionalization was performed on MINP(5H + 4VB) because 5H contained no imine bond.
[c]NINP was nonimprinted nanoparticle prepared with 1 equiv FM 4 but without any template.

Removal of 4-vinylbenzoic acid (4VB) in the MINP preparation reduced the yield from 66% to 38% for MINP (5E+7E) (entries 3 and 5), indicating that the first acid from 4VB was also important. This result also supports cooperative action between the two acids, in line with the design. Additional evidence for the cooperativity comes from the very poor performance of MINP(5H+4VB) (entry 12). Template 5H does not have an imine group and thus could only introduce a single carboxylic acid through 4VB.

Amide-containing free radical cross-linkers such as N, N'-methylenebisacrylamide (MBAm) may be used in combination with DVB in the MINP preparation to create a layer of interfacial hydrogen bonds to bind the glycan (entries 5-9). The best result was obtained with a 3:1 ratio of DVB to MBAm (entry 9).

The different templates influenced the catalytic hydrolysis of cellobiose (entries 9-12). MINP(5E+7E) and MINP(5G+7E) were better catalysts than MINP(5F+7E), whose ortho-dimethoxy groups might have sterically hindered the installment of the 4VB group. Control experiments showed that neither acid (4VB or 7E) was competent outside the MINP active site (entries 13-15), alone or in the presence of nonimprinted nanoparticles (NINP).

Figure 16:
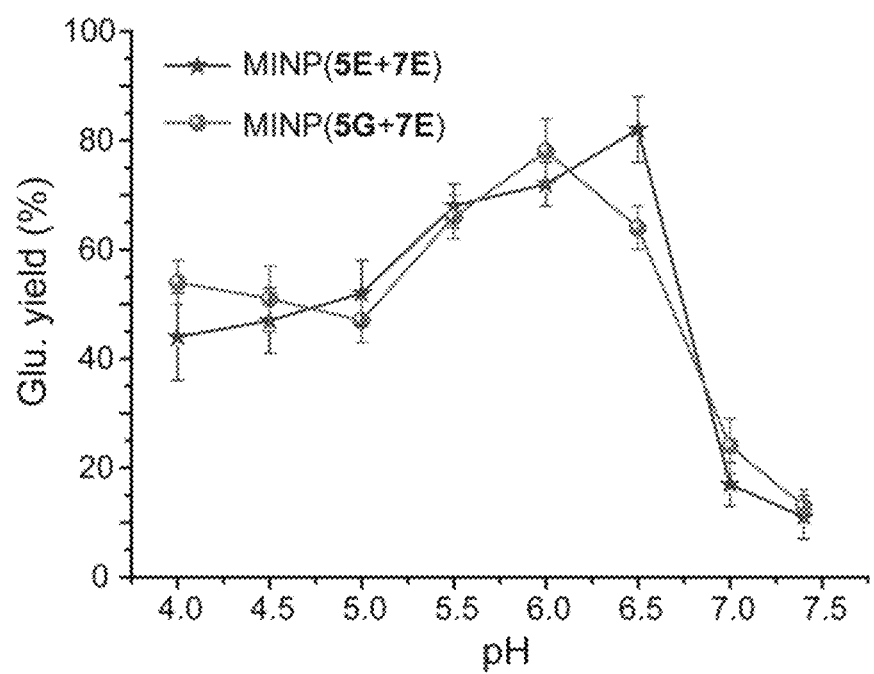
FIG. 16 is the effects of solution pH on the hydrolysis of cellobiose by MINP(5E+7E) and MINP(5G+7E). Reactions were performed with 0.2 mM of cellobiose and 20 µM of MINP in 1.0 mL buffer (10 mM) at 60° C. for 24 h.

The pH profiles MINP(5E+7E) and MINP(5G+7E) resemble those of natural glycosidase that often peak at pH 5-6 where one carboxylic acid of the active site is protonated and the other deprotonated (FIG. 16). Similarity of the pH curves suggests that a similar cooperative mechanism was in operation in the synthetic glycosidases. Further evidence for the cooperativity is discussed above, in the strong dependence of the catalysis in the distance between the two acids and the poor yields of the monoacid control catalysts.

Table 13 (entries 16-20) shows that a reasonable yield in cellobiose hydrolysis was obtained when the second catalytic group was an amine. The results demonstrate that a totally "unnatural" catalytic motif could be used in the synthetic glycosidase, which should enable the tuning of the optimal pH for cellulose hydrolysis due to the different $pK_a$ of the catalytic groups. Among the acid-amine-functionalized catalysts, MINP(5E+7M) gave the highest yield (entry 19).

The active site base changed the pH profile of the acid-amine-functionalized catalyst. The precipitous drop of activity that occurred near pH 6.5 in the dicarboxylic acid MINPs (FIG. 16) took place above pH 7 for MINP(5E+7M) (FIG. 17), suggesting hot water should be enough for cellulose hydrolysis with the "unnatural" acid-amine-functionalized catalyst. Elimination of externally added acids altogether for cellulose hydrolysis is highly desirable because soluble acids can cause side reactions and require corrosion-resistant equipment for the hydrolysis. Large amounts of acidic waste also are an environmental hazard.

Figure 18:
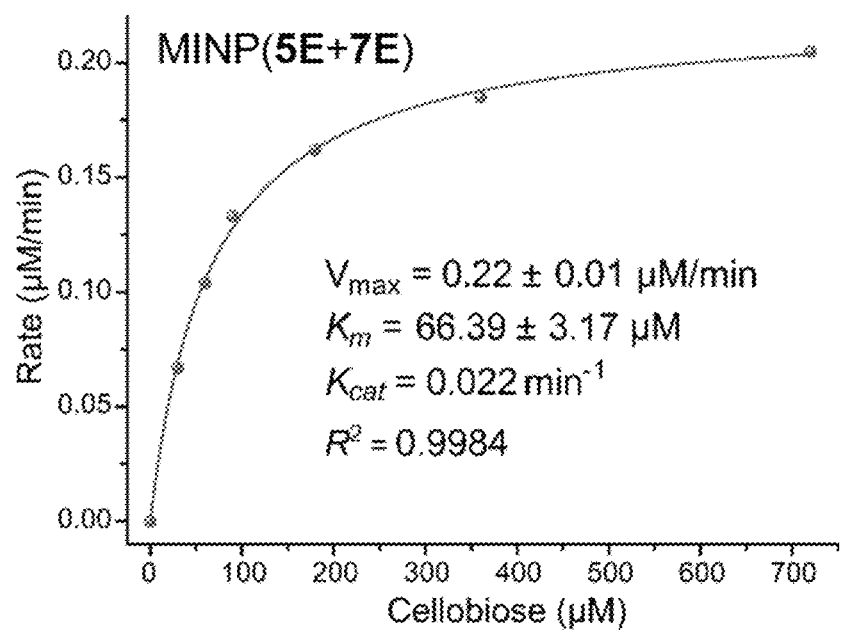
FIG. 18 is the Michaelis-Menten plot for the hydrolysis of cellobiose by MINP(5E+7E) in water at 60° C. [MINP]=10.0 µM.
Figure 19:
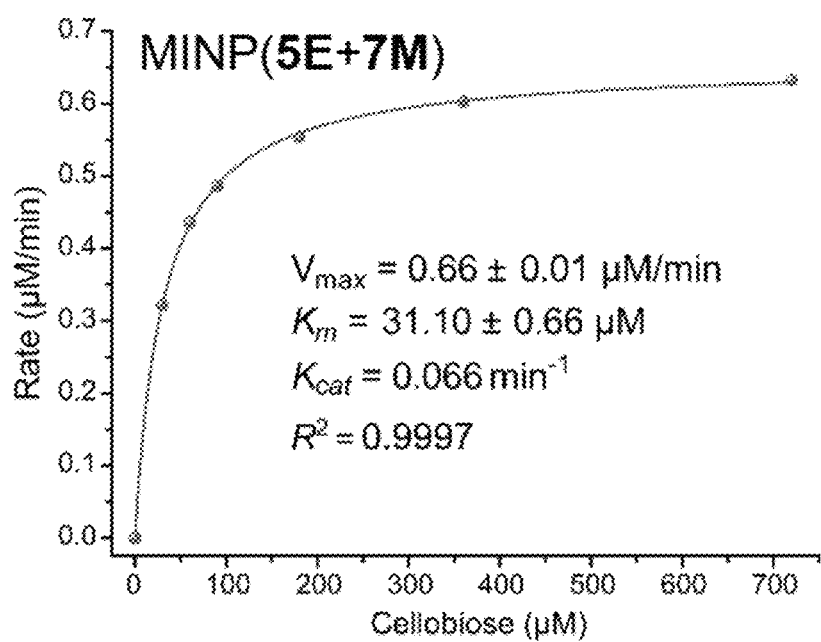
FIG. 19 is the Michaelis-Menten plot for the hydrolysis of cellobiose by MINP(5E+7M) in water at 60° C. [MINP]=10.0 µM.

FIGS. 18 and 19 show the Michaelis-Menten plots of MINP(5E+7E) and MINP(5E+7M) in 60° C. water, respectively. Consistent with the pH behaviors for the two MINPs, the acid-amine catalytic motif outperformed the biomimetic dicarboxylic acid in the catalysis. Both MINPs showed very strong binding for the substrate, with a $K_m$ of 66 μM for MINP(5E+7E) and 31 μM for MINP(5E+7M). Having a stronger binding for the substrate and faster turnover ($k_{cat}$=0.066 vs 0.022 min$^{-1}$) for the substrate, the acid-amine-functionalized catalyst afforded a catalytic efficiency ($k_{cat}/K_m$) of 2060 M$^{-1}$ min$^{-1}$ in 60° C. water. This value exceeds those of some natural enzymes, e.g., digestive β-glucosidase GH1 from *Spodoptera frugiperda* ($k_{cat}/K_m$=1780 M$^{-1}$ min$^{-1}$, $k_{cat}$=of 5.7 min$^{-1}$ and $K_m$=3.2 mM) (Tamaki, F. K.; Araujo, E. M.; Rozenberg, R.; Marana, S. R. A Mutant B-Glucosidase Increases the Rate of the Cellulose Enzymatic Hydrolysis. *Biochem. Biophys. Rep.* 2016, 7, 52-55).

Glycosidic bonds hydrolyze extremely slowly in water. The rate constant for the hydrolysis of cellobiose, extrapolated from methyl β-D-glucopyranoside hydrolyzed at 180-260° C., is 4.7×10$^{-15}$ s$^{-1}$ at 25° C. and 2.48×10$^{-14}$ s$^{-1}$ at 60° C. in water (Wolfenden, R.; Lu, X.; Young, G. Spontaneous Hydrolysis of Glycosides. *J. Am. Chem. Soc.* 1998, 120, 6814-6815). The $k_{cat}/k_{uncat}$ value for MINP(5E+7E) and MINP(5E+7M) at 60° C., was 1.5 and 4.4×10$^{10}$, respectively. Accurate placement of even weak acids and bases near the glycosidic bonds can achieve remarkable rate acceleration.

Table 14 summarizes the binding data of the MINPs for glucose and cellobiose obtained from isothermal titration calorimetry (ITC). MINP(5E)-CHO—i.e., the intermediate MINP with a single acid from 4VB and the aldehyde in the active site-displayed a binding constant ($K_a$) of 8.85×10$^3$ M$^{-1}$ for glucose in pH 6 buffer (entry 1). Molecular imprinting was clearly responsible for the binding, as the nonimprinted nanoparticles (NINP) prepared with FM 2 but without any template showed negligible binding (entry 2).

Since template 5E contained a single glucosyl residue and a boroxole FM was included in the MINP preparation, binding of glucose was expected. Interestingly, cellobiose was bound more strongly than glucose by MINP(5E)-CHO, by a factor ($K_{rel}$) of 3.9 (entry 3). A stronger binding of the catalyst for the larger sugar is desirable, as product inhibition (by glucose) will be less of a concern in the catalytic hydrolysis. A small imprinted site generally has difficulty accommodating a larger guest but a large imprinted site can bind a smaller guest if it can fill part of the imprinted site, for simple geometrical reasons. MINP(5E)-CHO, however, has significant void space in addition to the glucose binding site (see schematic representation in FIG. 15). Since a carboxylic acid was installed near the anomeric carbon of the glucose unit, potential hydrogen bonding interactions could form between this carboxylic acid and the glucosyl on the reducing end of cellobiose.

A stronger binding of cellobiose was also observed in MINP(5F)-CHO and MINP(5G)-CHO, suggesting the trend was consistent. Among the three, MINP(5F)-CHO exhibited the smallest cellobiose/glucose ratio (entry 3). It is possible that the two ortho-methoxy groups sterically interfered with the salt bridge formation in the ternary complex during MINP reparation, and, in turn, the installment of the carboxylic acid from 4VB, as discussed above.

MINP(5E+7E) and MINP(5E+7M), bound glucose significantly better than MINP(5E)-CHO (entries 8 and 12 and 1, respectively). Hence, the second catalytic group, whether a carboxylic acid from 7E or a pyridyl from 7M, also contributed to the binding, likely through additional hydrogen bonds with the hemiacetal hydroxyl of the bound glucose.

Although the binding for cellobiose also increased from MINP(5E)-CHO to the two synthetic glycosidases, the increase was smaller than for glucose, making the cellobiose/glucose binding ratio go below 1 (entries 9 and 13). The result was reasonable if the added catalytic group encountered steric repulsion with the glucosyl of cellobiose in the nonreducing end.

The binding constants for glucose and cellobiose in water were significantly larger than those in buffer (Table 14, entries 8-15). Fortunately, water favored the binding of cellobiose more than glucose and partly recovered the decrease of the cellobiose/glucose binding ratio (entries 11 and 15). The final value of $K_{rel}$ was 1.6 for MINP(5E+7E) and MINP(5E+7M), the best catalysts in this series (entries 11 and 15).

TABLE 14

ITC binding data for sugar guests by MINPs at 298K.[a]

| entry | MINP | guest | pH | $K_a$ ($\times 10^3$ M$^{-1}$) | $K_{rel}$[b] | N |
|---|---|---|---|---|---|---|
| 1 | MINP(5E)-CHO | glucose | 6 | 8.85 ± 0.37 | 1 | 1.21 ± 0.04 |
| 2 | NINP[c] | glucose | 6 | <0.05 [b] | — | — |
| 3 | MINP(5E)-CHO | cellobiose | 6 | 34.30 ± 1.07 | 3.9 | 1.30 ± 0.07 |
| 4 | MINP(5F)-CHO | glucose | 6 | 9.44 ± 0.29 | 1 | 1.28 ± 0.08 |
| 5 | MINP(5F)-CHO | cellobiose | 6 | 13.10 ± 0.78 | 1.4 | 1.12 ± 0.02 |
| 6 | MINP(5G)-CHO | glucose | 6 | 7.48 ± 0.39 | 1 | 1.21 ± 0.06 |
| 7 | MINP(5G)-CHO | cellobiose | 6 | 29.30 ± 2.33 | 3.9 | 1.29 ± 0.09 |
| 8 | MINP(5E + 7E) | glucose | 6 | 62.4 ± 2.44 | 1 | 1.15 ± 0.04 |
| 9 | MINP(5E + 7E) | cellobiose | 6 | 41.6 ± 1.55 | 0.7 | 1.23 ± 0.01 |
| 10 | MINP(5E + 7E) | glucose | water | 137.3 ± 12.6 | 1 | 1.17 ± 0.03 |
| 11 | MINP(5E + 7E) | cellobiose | water | 217.5 ± 19.1 | 1.6 | 1.10 ± 0.02 |
| 12 | MINP(5E + 7M) | glucose | 6 | 55.1 ± 12.2 | 1 | 1.11 ± 0.01 |
| 13 | MINP(5E + 7M) | cellobiose | 6 | 36.4 ± 12.2 | 0.7 | 1.05 ± 0.02 |
| 14 | MINP(5E + 7M) | glucose | water | 124.4 ± 12.2 | 1 | 1.14 ± 0.03 |
| 15 | MINP(5E + 7M) | cellobiose | water | 197.2 ± 12.2 | 1.6 | 1.12 ± 0.01 |

[a]MINPs were prepared with 1.0 equiv. of 4VB and a 3:1 ratio of DVB/MBAm. The cross-linkable surfactants were a 3:2 mixture of 1 and 2. The titrations were performed in 10 mM MES buffer at pH 6.0 or Millipore water at 298K. N is the average number of binding site per nanoparticle measured by ITC.
[b] $K_{rel}$ is the binding constant of cellobiose relative to that of glucose by the same MINP receptor.
[c]Nonimprinted nanoparticles (NINP) were prepared with 1.0 equiv. FM 4 but without any template and postfunctionalization. Because the binding constant was estimated from ITC, –AG and N are not listed.

Figure 17:
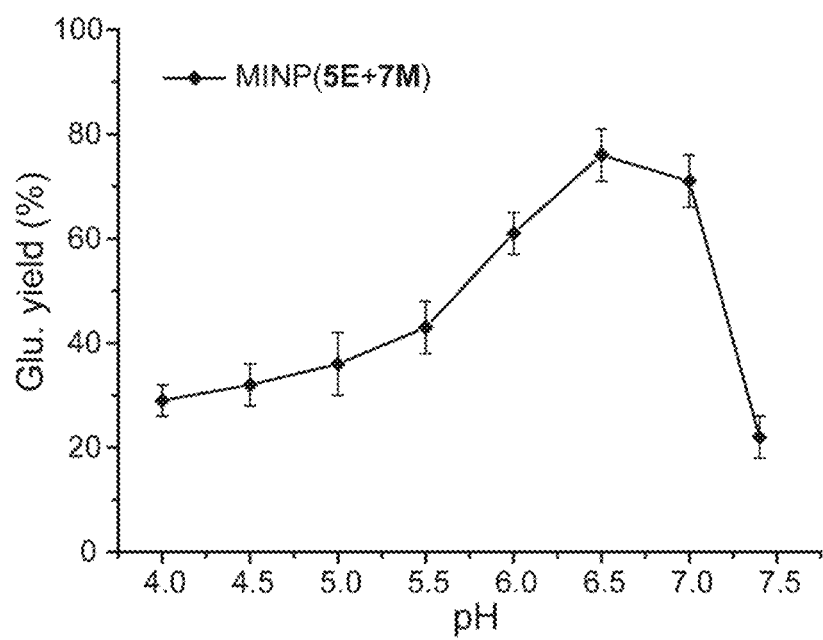
FIG. 17 is the effects of solution pH on the hydrolysis of cellobiose by MINP(5E+7M). Reactions were performed with 0.2 mM of cellobiose and 20 µM of MINP in 1.0 mL buffer (10 mM) at 60° C. for 24 h.
Figure 20:
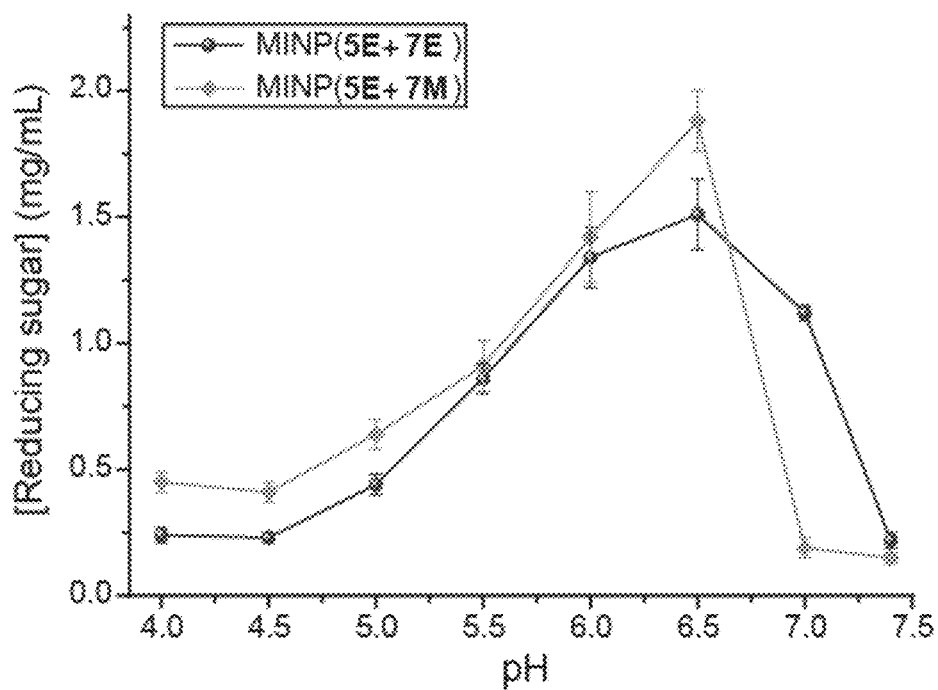
FIG. 20 is the effects of solution pH on the hydrolysis of cellulose by MINP(5E+7E) and MINP(5E+7M). Reactions were performed with [cellulose]=[MINP]=5.0 mg/mL in 1 mL 10 mM buffer at different pHs for 24 h.

The catalysts were then used to hydrolyze cellulose in aqueous buffers. The heterogeneous reaction of cellulose hydrolysis (FIG. 20) maintained a similar pH profile as the homogeneous reaction of cellobiose hydrolysis (FIGS. 16 and 17). For the dicarboxylic acid catalyst MINP(5E+7E), a large drop of activity was observed over pH 6.5 to 7.0. For the acid-amine-functionalized MINP(5E+7M), the largest drop occurred at pH 7-7.5. Thus, strong catalytic power was retained under neutral condition for this MINP.

Table 15 compares the enzyme activities of MINP(5E+7E) and MINP(5E+7M) with that of cellulase from *Aspergillus niger*. A reaction temperature of 37° C. was used for enzyme-catalyzed hydrolysis and 60° C. for MINP-catalyzed hydrolysis. The natural enzyme displayed an enzyme activity of 0.178 μmol mg$^{-1}$ h$^{-1}$ in pH 5 buffer at a catalyst concentration of 2.0 mg/mL (entry 1) and this value was used as the reference to which everything else was normalized. The natural cellulase lost 97% of its activity going from the acidic buffer (entry 2) to water. MINP(5E+7E), as expected, performed also poorly in water (entry 3). MINP(5E+7M), consistent with its strong performance in the cellobiose hydrolysis, showed much higher activity (entries 4-13).

TABLE 15

Hydrolysis of cellulose by cellulases and MINP catalysts.[a]

| entry | catalysts | catalyst conc. (mg/ml) | solvent | temp (° C.) | enzyme activity (μmol mg$^{-1}$ h$^{-1}$) | relative activity (MINP/enzyme) |
|---|---|---|---|---|---|---|
| 1 | cellulase | 2.0 | buffer[b] | 37 | 0.178 ± 0.042 | 1 |
| 2 | cellulase | 2.0 | H$_2$O | 37 | 0.005 ± 0.001 | 0.03 |
| 3 | MINP(5E + 7E) | 5.0 | H$_2$O | 60 | 0.008 ± 0.002 | 0.04 |
| 4 | MINP(5E + 7M) | 5.0 | H$_2$O | 60 | 0.041 ± 0.002 | 0.23 |
| 5 | MINP(5E + 7M) | 4.0 | H$_2$O | 60 | 0.042 ± 0.003 | 0.24 |
| 6 | MINP(5E + 7M) | 3.0 | H$_2$O | 60 | 0.050 ± 0.002 | 0.28 |
| 7 | MINP(5E + 7M) | 2.0 | H$_2$O | 60 | 0.053 ± 0.001 | 0.30 |
| 8 | MINP(5E + 7M) | 1.0 | H$_2$O | 60 | 0.049 ± 0.004 | 0.28 |
| 9 | MINP(5E + 7M) | 0.5 | H$_2$O | 60 | 0.028 ± 0.001 | 0.16 |
| 10 | MINP(5E + 7M) | 2.0 | H$_2$O | 90 | 0.067 ± 0.002 | 0.38 |
| 11 | MINP(5E + 7M) | 2.0 | H$_2$O | 100 | 0.073 ± 0.003 | 0.41 |
| 12 | MINP(5E + 7M)[c] | 2.0 | H$_2$O | 100 | 0.065 ± 0.002 | 0.37 |
| 13 | MINP(5E + 7M)[d] | 2.0 | H$_2$O | 100 | 0.048 ± 0.003 | 0.27 |

[a]The reactions were performed in duplicates with [Sigmacell cellulose] = 5.0 mg/mL in 1.0 mL aqueous buffer or water for 24 h unless indicated otherwise. The relative activity was the enzyme activity of MINP at the given temperature divided by the enzyme activity of cellulase at 37° C. shown in entry 1.
[b]pH 5 NaOAc buffer.
[c]α-Cellulose was used in the experiment.
[d]Avicel PH-101 was used in the experiment.

For a heterogeneous reaction, only enzymes bound on the surface of cellulose could catalyze the hydrolysis. The catalysis, as a result, is generally concentration-dependent: too small an amount of catalyst cannot cover the surface fully and too large an amount results in unused catalysts in the solution. MINP(5E+7M), as shown by entries 4-9 of Table 15, displayed a concentration dependency. Its activity in 60° C. water ranged from 16 to 30% of that of the natural cellulase under the latter's optimal conditions (37° C. in pH 5 buffer). The optimal amount of catalyst was 2.0 mg/mL under the specific experimental conditions (entry 7).

As highly cross-linked polymeric nanoparticle, MINP (5E+7M) displayed a strong tolerance for high temperatures. Its activity continued to rise at elevated temperatures, with an MINP/enzyme ratio reaching 0.38 at 90° C. (Table 15, entry 10) and 0.41 in boiling water (entry 11). Different types of cellulose showed some difference in activity, with Sigmacell and α-cellulose giving better yields than Avicel PH-101 (entries 11-13).

Figure 21:
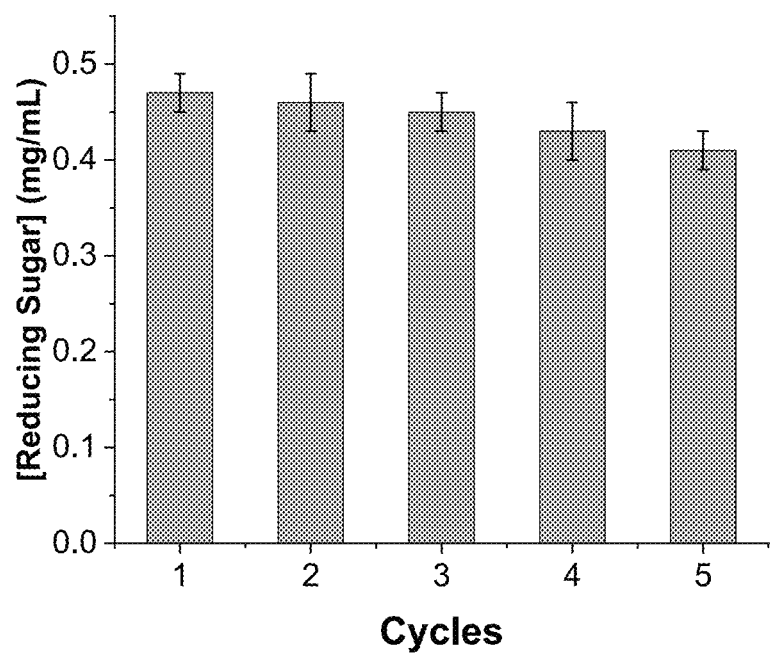
FIG. 21 is the recyclability of MINP(5E+7M) for cellulose hydrolysis in 60° C. water.

FIG. 21 shows five rounds of cellulose hydrolysis. In each catalytic cycle, 5 mg of cellulose was added to a dialysis tubing with a MW-cutoff (MWCO) of 500 Da, which should let small sugar products escape but keep the MINP catalyst and unreacted cellulose inside. After 24 h at 60° C., another batch of cellulose was added, while the solution outside was analyzed.

The catalytic power of an enzyme can be measured by its proficiency, a term defined by Wolfenden and calculated from $(k_{cat}/K_m)/k_{uncat}$ (Radzicka, A.; Wolfenden, R. A Proficient Enzyme. Science 1995, 267, 90-93). The proficiency can be viewed as the affinity of the enzyme for the transition state of the reaction and is useful for comparing enzymes that catalyze different reactions. MINP(5E+7E) and MINP (5E+7M) have a proficiency of $2.24 \times 10^{14}$ $M^{-1}$ and $1.39 \times 10^{15}$ $M^{-1}$ for cellobiose hydrolysis in 60° C. water, translating to a T.S. stabilization energy of 23.2 and 24.5 kcal/mol, respectively. Boronate bonds and hydrogen bonds were involved in the binding of both the cellobiose substrate and the transition state of the hydrolysis. However, the ITC study shows that the binding for cellobiose was only ~7 kcal/mol. Selective binding for the transition state is the hallmark of enzymes, and the 16-17 kcal/mol differential is the reason behind the large rate acceleration ($10^{10}$).

Synthesis & Characterization
Syntheses of 1-4 and 8.

Syntheses of 1-4 and 8 followed reported procedures in the literature: Awino, J. K.; Zhao, Y. Protein-Mimetic, Molecularly Imprinted Nanoparticles for Selective Binding of Bile Salt Derivatives in Water. *J. Am. Chem. Soc.* 2013, 135, 12552-12555; Gunasekara, R. W.; Zhao, Y. A General Method for Selective Recognition of Monosaccharides and Oligosaccharides in Water. *J. Am. Chem. Soc.* 2017, 139, 829-835.

Figure 22:
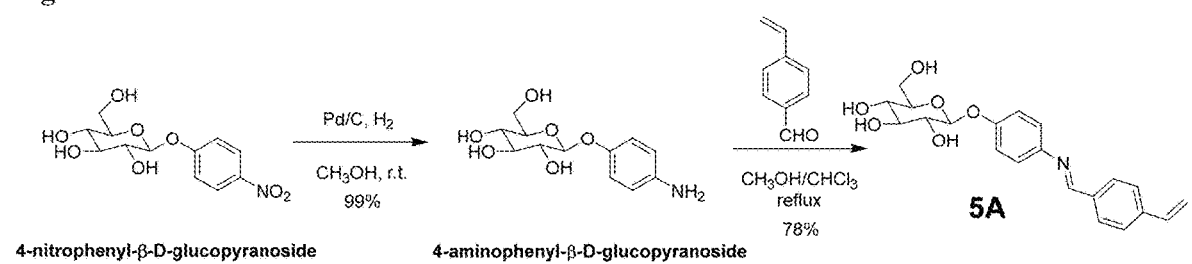
FIG. 22 is the synthesis of template 5A.

Synthesis of 5A (FIG. 22)

4-Aminophenyl-β-D-glucopyranoside. 4-Nitrophenyl-β-D-glucopyranoside (200 mg, 0.66 mmol) was hydrogenated in methanol (10 mL) with Pd/C (40 mg, w %=20%). After 12 h, the catalyst was removed by filtration, and methanol was removed in vacuo. The residue was crystallized from ethanol to give a white powder (171 mg, 95%). $^1$H NMR (400 MHz, 298 K, CD$_3$OD) δ 6.95 (d, J=8.8 Hz, 2H), 6.68 (d, J=8.8 Hz, 2H), 5.27 (d, J=4.0 Hz, 1H), 3.85-3.80 (m, 1H), 3.77-3.71 (m, 3H), 3.54-3.51 (m, 1H), 3.44-3.34 (m, 1H). $^{13}$C NMR (100 MHz, 298 K, CD$_3$OD) δ 150.28, 142.05, 118.37, 116.44, 99.13, 73.59, 72.75, 72.01, 61.00. HRMS (ESI$^+$/QTOF) Calcd for C$_{12}$H$_{17}$NO$_6$ m/z: [M+H]$^+$ 272.1129; Found 272.1162.

Compound 5A. A solution of 4-aminophenyl-β-D-glucopyranoside (100 mg, 0.369 mmol) and 4-vinylbenzaldehyde (73 mg, 0.553 mmol) in CHCl$_3$ (0.5 mL) and ethanol (3 mL) was heated to reflux overnight. After the reaction mixture was cooled to room temperature, diethyl ether (30 mL) was added slowly. The precipitate formed was collected by filtration and washed with cold diethyl ether to yield a white powder (111 mg, 78%). $^1$H NMR (400 MHz, 298 K, DMSO-d$_6$) δ 8.63 (s, 1H), 7.89 (d, J=8.4 Hz, 2H), 7.61 (d, J=8.4 Hz, 2H), 7.28 (d, J=8.8 Hz, 2H), 7.13 (d, J=8.8 Hz, 2H), 6.81 (m, 1H), 5.97 (m, 1H), 5.39-5.36 (m, 1H), 5.07 (d, J=6.4 Hz, 1H), 4.99 (d, J=5.6 Hz, 1H), 4.95 (d, J=5.6 Hz, 1H) 4.50 (m, 1H), 3.65-3.63 (m, 2H), 3.48-3.46 (m, 2H), 3.39-3.37 (m, 1H), 3.22-3.16 (m, 1H). $^{13}$C NMR (100 MHz, 298 K, DMSO-d$_6$) δ 158.85, 156.25, 145.76, 140.14, 136.57, 136.17, 135.46, 129.22, 128.71, 126.97, 122.69, 118.05, 116.49, 98.66, 74.20, 73.51, 72.05, 70.38, 61.14. HRMS (ESI$^+$/QTOF) Calcd for C$_{21}$H$_{23}$NO$_6$ m/z: [M+H]$^+$ 386.1598; Found m/z 386.1620; [M+HCOO]$^-$ 430.1507; Found 430.1493.

Figure 23:
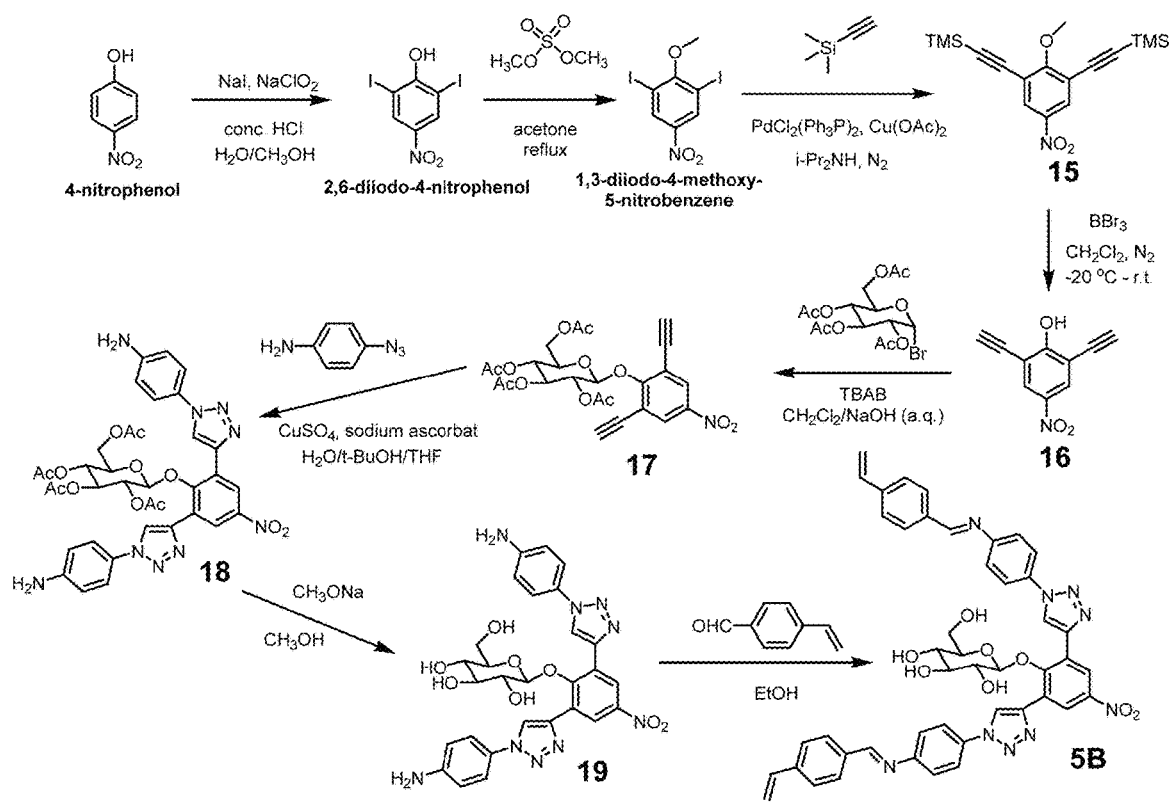
FIG. 23 is the synthesis of template 5B.

Synthesis of 5B (FIG. 23)

2,6-Diiodo-4-nitrophenol. 4-Nitrophenol (6.0 g, 43.2 mmol) in methanol (800 mL) was added slowly to a stirred solution of sodium chlorite (7.8 g, 86.2 mmol) and sodium iodide (25.8 g, 172.6 mmol) in water (1000 mL) at 0° C., followed by 12 M HCl (8 mL, 96.0 mmol). The reaction mixture was allowed to warm to room temperature and stirred for 18 h. The aqueous solution was extracted with ethyl acetate (3×500 mL). The combined organic solution was washed with brine containing 1% w/v Na$_2$S$_2$O$_3$ (3×300 mL), water (500 mL), brine (500 mL), dried over anhydrous sodium sulfate, and concentrated in vacuo to afford an orange solid which was directly used to next step (15.9 g, 94%). $^1$H NMR (400 MHz, 298 K, CD$_3$COCD$_3$) δ 8.51 (s, 2H), 4.32 (s, br, 1H). $^{13}$C NMR (100 MHz, 298 K, CD$_3$COCD$_3$) δ 169.83, 135.07, 134.19, 87.07. HRMS (ESI$^-$/QTOF) Calcd for C$_6$H$_3$NO$_3$I$_2$ m/z: [M-H]$^-$ 389.8130; Found 389.8134.

1,3-Diiodo-4-methoxy-5-nitrobenzene. Potassium carbonate (5.30 g, 38.4 mmol) was added to a stirred solution of 2,6-diiodo-4-nitrophenol (5.00 g, 12.8 mmol) in acetone (150 mL) at 0° C. Dimethyl sulfate (3.6 mL, 38.4 mmol) was added in one portion. After the solution was heated to reflux for 18 h, ammonia hydroxide (50 mL) was added. After the solution was concentrated in vacuo to remove acetone, the residue was extracted with ethyl acetate (3×100 mL). The combined organic solution was washed with brine (500 mL), dried over anhydrous sodium sulfate, and concentrated in vacuo. The residue was purified by column chromatography over silica gel using a mixture of hexane and ethyl acetate (4:1 to 1:1) as the eluent to give a white powder (4.77 g, 92%). $^1$H-NMR (400 MHz, CDCl$_3$): δ 8.64 (s, 2H), 3.94 (s, 3H), $^{13}$C-NMR (100 MHz, CDCl$_3$): 164.36, 144.66, 135.01, 89.76, 61.07; HRMS (ESI$^+$/QTOF) Calcd for C$_7$H$_5$I$_2$NO$_3$ m/z: [M+H]$^+$ 405.8432; Found 405.8445.

Compound 15. A mixture of 1,3-diiodo-4-methoxy-5-nitrobenzene (1.00 g, 2.47 mmol), trimethylsilylacetylene (728 mg, 7.41 mmol), N,N-diisopropylethylamine (10 mL), Pd(PPh$_3$)$_2$Cl$_2$ (175 mg, 0.25 mmol), PPh$_3$ (131 mg, 0.50 mmol), and CuI (48 mg, 0.25 mmol) in anhydrous THF (20 mL) was stirred under nitrogen at 50° C. After 12 h, the precipitate was removed by filtration and the filtrate was concentrated in vacuo. The residue was purified by column chromatography over silica gel using a mixture of hexane and ethyl acetate (5:1) as the eluent to give a white powder (665 mg, 77%). $^1$H NMR (400 MHz, CDCl$_3$): δ 8.21 (s, 2H), 4.19 (s, 3H), 0.26 (s, 18H), $^{13}$C-NMR (100 MHz, CDCl$_3$): 166.77, 142.18, 129.19, 117.20, 102.30, 98.42, 61.25, 0.37; HRMS (ESI$^+$/QTOF) Calcd for C$_{17}$H$_{23}$NO$_3$Si$_2$ m/z: [M+H]$^+$ 346.1289; Found 346.1289.

Compound 16. Boron tribromide in dichloromethane (1 M, 6 mL, 6.0 mmol) was slowly added to a solution of compound 15 (680 mg, 1.98 mmol) in anhydrous dichloromethane (60 mL) at −78° C. under $N_2$ for 10 min. The mixture was allowed to warm to room temperature and stirred for 12 h. After slow addition of $H_2O$ (20 mL), the organic phase was washed with a saturated ammonium chloride solution (2×120 mL), water (1×100 mL), and brine (1×250 mL). The organic phase was filtered through a pad of Celite and diluted with ethyl acetate (200 mL). The combined organic solution was washed with a saturated ammonium chloride solution (2×100 mL) and brine (1×100 mL), dried over anhydrous sodium sulfate, and concentrated in vacuo. The residue was purified by column chromatography over silica gel using a mixture of hexane and ethyl acetate (4:1 to 1:1) as the eluent to give a brown powder (293 mg, 79%). $^1$H NMR (400 MHz, $CDCl_3$): δ 8.31 (s, 2H), 6.78 (br, s, 1H), 3.55 (s, 2H), $^{13}$C-NMR (100 MHz, $CDCl_3$): 162.80, 135.83, 129.08, 110.02, 85.86, 75.87; HRMS (ESI−/QTOF) Calcd for $C_{10}H_5NO_3$ m/z: [M−H]− 186.0197; Found 186.0193.

Compound 17. Tetrabutylammonium bromide (TBAB, 256 mg, 0.80 mmol) and compound 16 (100 mg, 0.53 mmol) were added to a solution of 2,3,4,6-tetra-O-acetyl-alpha-D-glucopyranosyl bromide (260 mg, 0.64 mmol) in anhydrous dichloromethane (4 mL) at 0° C., followed by the addition of 1M NaOH (4 mL). The bilayer mixture was stirred vigorously at room temperature for 12 h, followed by the addition of EtOAc (50 mL). The combined organic phase was washed with 1M NaOH solution and brine, dried over anhydrous sodium sulfate, and concentrated in vacuo. The residue was purified by column chromatography over silica gel using a mixture of hexane and ethyl acetate (10:1) as the eluent to give a colorless syrup (208 mg, 76%). $^1$H NMR (400 MHz, $CDCl_3$) δ 8.29 (s, 2H), 5.79 (d, J=7.6 Hz, 1H), 5.34 (m, 1H), 5.28-5.23 (m, 2H), 4.23 (dd, $J_1$=12.4 Hz, $J_2$=4.8 Hz, 1H), 4.09 (m, 1H), 3.77 (m, 1H), 3.43 (s, 2H), 2.04 (s, 3H), 2.03 (s, 3H), 2.03 (s, 3H), 2.02 (s, 3H); $^{13}$C NMR (100 MHz, $CDCl_3$) δ 170.44, 170.27, 169.33, 169.12, 143.15, 129.78, 116.74, 99.25, 84.89, 76.84, 72.69, 71.83, 71.57, 68.17, 61.83, 20.77, 20.69, 20.61, 20.57; HRMS (ESI+/QTOF) Calcd for $C_{24}H_{27}N_2O_{12}$ m/z: [M+$NH_4$]+ 535.1559; Found 535.1584.

Compound 18. Sodium ascorbate (115 mg, 0.58 mmol) and copper acetate hydrate (96 mg, 0.48 mmol) were added to a solution of compound 17 (100 mg, 0.19 mmol) and 4-azidoaniline (57 mg, 0.43 mmol) in a mixture of methanol/THF/water (1 mL/1 mL/2 mL). The mixture was stirred at room temperature for 24 h and diluted with water (20 mL) and ethyl acetate (30 mL). The organic layer was dried over anhydrous $Na_2SO_4$, filtered and concentrated in vacuo. The residue was purified by column chromatography over silica gel using a mixture of hexane and ethyl acetate (5:1) as the eluent to give a brown powder (158 mg, 95%). $^1$H NMR (400 MHz, $CD_3COCD_3$) δ 8.96 (s, 2H), 8.78 (s, 2H), 7.96 (d, J=8.8 Hz, 1H), 7.64 (d, J=8.8 Hz, 3H), 7.04 (d, J=8.8 Hz, 1H), 6.89 (d, J=8.8 Hz, 3H), 5.60 (d, J=8.8 Hz, 1H), 5.50-5.45 (m, 2H), 5.02-4.99 (m, 1H), 3.95-3.90 (m, 1H), 3.79-3.75 (m, 2H), 2.15 (s, 4H), 2.14 (s, 3H) 2.06 (s, 3H), 1.95 (s, 3H), 1.88 (s, 3H); $^{13}$C NMR (100 MHz, $CD_3COCD_3$) δ 169.58, 169.40, 169.32, 168.95, 152.37, 152.21, 149.44, 145.35, 141.22, 127.94, 127.08, 122.49, 122.20, 121.55, 114.31, 98.50, 71.95, 71.90, 71.74, 68.10, 60.75, 20.12, 19.66, 19.58, 19.35; HRMS (ESI+/QTOF) Calcd for $C_{36}H_{35}N_9O_{12}$ m/z: [M+H]+ 786.2478; Found 786.2484, [M+Na]+ 808.2297; Found 808.2280.

Compound 19. A solution of compound 18 (40 mg, 0.05 mmol) in methanol/dichloromethane (5 mL/5 mL) with a catalytic amount of sodium methoxide was stirred at room temperature for 1 h. The solution was neutralized with Amberlite® IR-120 (H+) ion-exchange resin, filtered, and concentrated in vacuo. The residue was purified by column chromatography over silica gel using a mixture of dichloromethane and methanol (5:1) as the eluent to give a white powder (22 mg, 71%). $^1$H NMR (400 MHz, $CD_3OD$) δ 9.30 (s, 2H), 8.85 (s, 2H), 7.59 (d, J=8.8 Hz, 4H), 6.72 (d, J=8.8 Hz, 4H), 5.92 (d, J=9.2 Hz, 1H), 5.79-5.75 (m, 2H), 5.34-5.30 (m, 1H), 4.49-4.46 (m, 1H), 4.24-4.21 (m, 1H), 3.73-3.71 (m, 1H), 3.15 (s, 4H); $^{13}$C NMR (100 MHz, $CD_3OD$) δ 155.89, 149.26, 147.96, 145.03, 143.47, 141.66, 131.15, 127.74, 127.24, 123.40, 121.68, 119.17, 116.68, 114.69, 113.46, 112.33, 111.50, 109.98, 108.59, 104.79, 78.25, 76.77, 76.14, 74.57, 69.61, 64.27; HRMS (ESI+/QTOF) Calcd for $C_{28}H_{27}N_9O_8$ m/z: [M+H]+618.2055; Found 618.2052, [M+Na]+ 640.1875; Found 640.1877.

Compound 5B. A solution of 19 (40 mg, 0.065 mmol) and 4-vinylbenzaldehyde (172 mg, 1.295 mmol) in $CHCl_3$ (0.5 mL) and ethanol (6 mL) was heated to reflux overnight. After the reaction mixture was cooled to room temperature, diethyl ether (30 mL) was added slowly. The precipitate formed was collected by filtration and washed with cold diethyl ether to afford a yellowish powder (43 mg, 78%). $^1$H NMR (400 MHz, DMSO-$d_6$) δ 9.39 (s, 2H), 8.88 (s, 2H), 8.72 (s, 2H), 8.01 (d, J=8.8 Hz, 4H), 7.95 (d, J=8.8 Hz, 4H), 7.65 (d, J=8.0 Hz, 4H), 7.52 (d, J=8.8 Hz, 4H), 6.82 (m, 2H), 6.19 (d, J=4.8 Hz, 1H), 5.99 (d, J=17.6 Hz, 2H), 5.41 (d, J=10.8 Hz, 2H), 5.28 (d, J=4.4 Hz, 1H), 4.96 (d, J=4.8 Hz, 1H), 4.92 (d, J=7.6 Hz, 1H), 4.37-4.28 (m, 1H), 3.61-3.56 (m, 1H), 3.45-3.40 (m, 1H) 3.27-3.19 (m, 2H), 2.99-2.96 (m, 1H); $^{13}$C NMR (100 MHz, DMSO-$d_6$) δ 161.89, 153.98, 152.12, 150.43, 145.01, 142.66, 141.94, 140.78, 136.51, 135.71, 134.82, 129.70, 128.08, 127.05, 124.13, 122.98, 121.61, 116.93, 109.99, 102.80, 80.39, 76.13, 74.71, 69.50; HRMS (ESI+/QTOF) Calcd for $C_{46}H_{39}N_9O_8$ m/z: [M+H]+ 846.2994; Found 846.2980, [M+Na]+ 868.2814; Found 868.2787.

Figure 24:
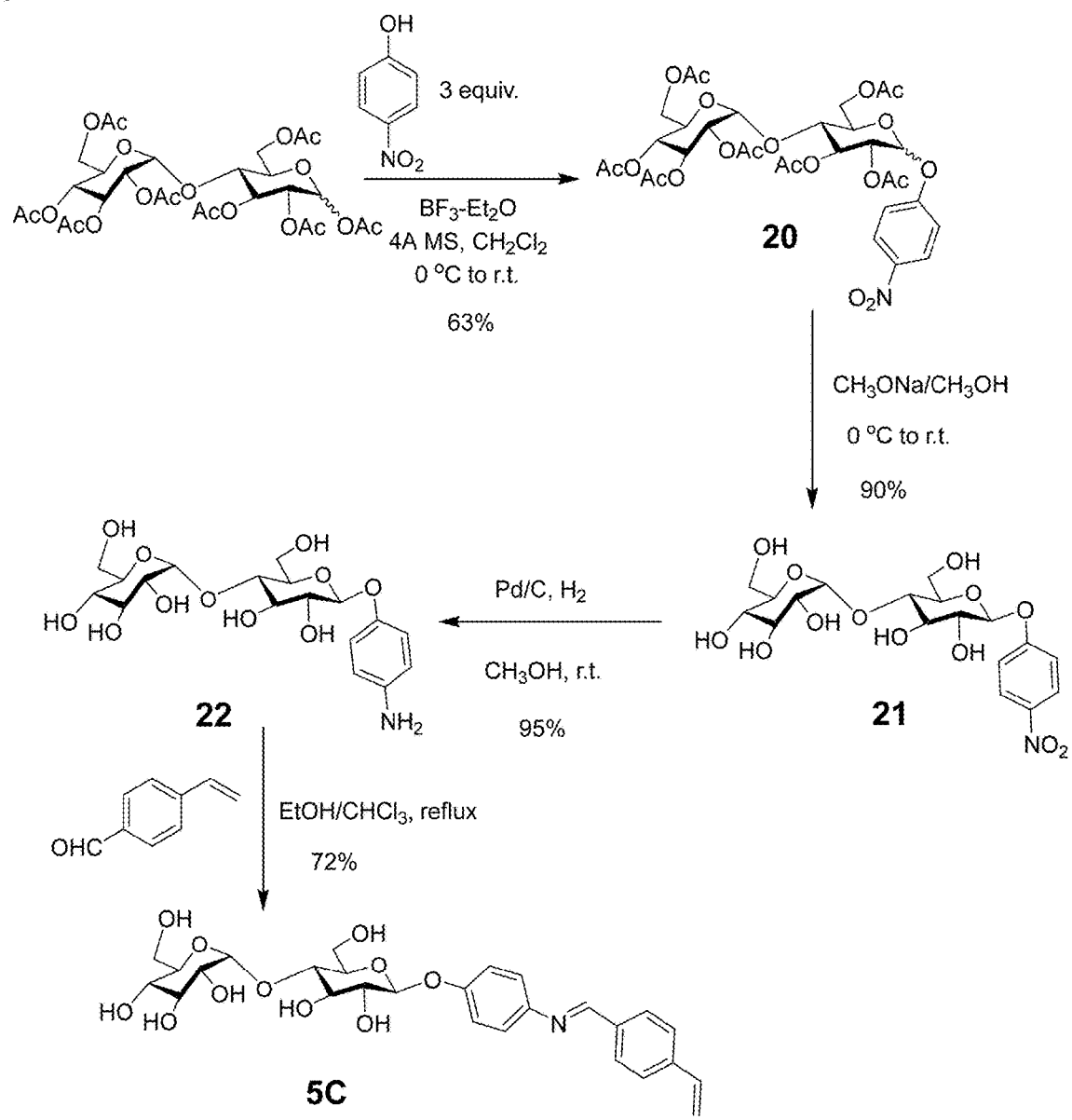
FIG. 24 is the synthesis of template 5C.

Synthesis of 5C (FIG. 24)

Compound 20. To a stirred solution of D-maltose octaacetate (500 mg, 0.74 mmol) and 4-nitrophenol (308 mg, 2.21 mmol) in anhydrous $CH_2Cl_2$ (5 mL) with activated 4 Å molecular sieves at 0° C. was added $BF_3$.$OEt_2$ (525 mg, 457 µL, 3.70 mmol). The mixture was warmed to room temperature and stirred for 24 h. A solution of saturated $NaHCO_3$ (20 mL) was added. The aqueous layer was extracted with $CH_2Cl_2$ (20 mL). The combined organic solution was washed with 1 M NaOH (3×20 mL) and $H_2O$ (20 mL), dried over $Na_2SO_4$, and concentrated in vacuo. The residue was crystallized from ethyl acetate/Hexane and the crude product was purified by column chromatography over silica gel to afford a colorless syrup (353 mg, 63%). $^1$H NMR (600 MHz, 298 K, $CDCl_3$) δ 8.15 (d, J=9.0 Hz, 2H), 7.02 (d, J=9.0 Hz, 2H), 5.39-5.28 (m, 2H), 5.23 (d, J=7.2 Hz, 1H), 5.11-5.07 (m, 1H), 5.02-4.98 (m, 1H), 4.83-4.80 (m, 1H), 4.46-4.43 (m, 1H), 4.23-4.18 (m, 2H), 4.07-4.00 (m, 3H), 3.93-3.91 (m, 2H), 2.05 (s, 3H), 2.04 (s, 3H), 2.03 (s, 3H), 2.01 (s, 3H), 1.99 (s, 3H), 1.98 (s, 3H), 1.96 (s, 3H). $^{13}$C NMR (125 MHz, 298 K, $CDCl_3$) δ 170.41, 170.16, 170.14, 170.06, 169.88, 169.43, 169.32, 161.06, 143.17, 125.74, 116.57, 97.43, 95.73, 74.95, 74.93, 72.61, 72.58, 71.63, 69.99, 69.19, 68.64, 67.99, 62.63, 61.54, 20.95, 20.83, 20.81, 20.62, 20.53, 20.51, 20.50. HRMS (ESI+/QTOF) Calcd for $C_{32}H_{39}NO_{20}$ m/z: [M+$NH_2$]+ 775.2404; Found 775.2359. HRMS (ESI−/QTOF) Calcd for $C_{32}H_{39}NO_{20}$ m/z: [M+HCOO]− 802.2047; Found 802.2105.

Compound 21. A solution of compound 20 (500 mg, 0.66 mmol) in methanol (10 mL) with a catalytic amount of sodium methoxide was stirred at room temperature for 3 h. The solution was neutralized with Amberlite® IR-120 (H+) ion-exchange resin, filtered, and concentrated in vacuo. The residue was purified by column chromatography over silica gel to afford compound 21 as a white powder (297 mg, 90%). $^1$H NMR (400 MHz, 298 K, CD$_3$OD) δ 8.21 (d, J=9.6 Hz, 2H), 7.23 (d, J=9.6 Hz, 2H), 5.21 (d, J=3.6 Hz, 1H), 5.11 (d, J=7.6 Hz, 1H), 3.93-3.90 (m, 1H), 3.87-3.82 (m, 2H), 3.79-3.63 (m, 13H), 3.58-3.54 (m, 1H), 3.49-3.45 (m, 1H), 3.31-3.29 (m, 2H). $^{13}$C NMR (100 MHz, 298 K, CD$_3$OD) δ 162.36, 142.47, 125.19, 116.29, 101.52, 100.03, 79.26, 76.12, 75.51, 73.62, 73.44, 72.86, 72.70, 70.11, 61.32, 60.42. HRMS (ESI−/QTOF) Calcd for $C_{18}H_{25}NO_{13}$ m/z: [M−H]− 462.1253 Found 462.1261, [M+Cl]− 498.1020; Found: n/z 498.1036, [M+HCOO]− 508.1308; Found 508.1321.

Compound 22. The same procedure for 4-aminophenyl-β-D-glucopyranoside was followed, using compound 21 (400 mg, 0.86 mmol) to afford compound 22 as a white crystal (354 mg, 95%). $^1$H N-MR (400 MHz, 298 K, CD$_3$OD) δ 6.93 (d, J=: 8.4 Hz, 2H), 6.70 (d, J=8.4 Hz, 2H), 5.20 (d, J=2.4 Hz, 11H), 4.78 (d, J=7.6 Hz, 1H), 4.50 (br, s, 2H), 3.89-3.80 (m, 3H), 3.75-3.65 (m, 6H), 3.54-3.43 (m, 411), 3.33-3.28 (m, 1H), 3.49-3.45 (m, 1H), 3.31-329 (m, 4H) $^{13}$C NMR (100 M-z, 298 K, CD$_3$OD) δ 150.63, 142.11, 117.87, 116.60, 101.95, 101.57, 79.56, 76.12, 75.02, 73.53, 73.39, 73.10, 72.59, 70.23, 61.24, 60.48. HRMS (ESI−/QTOF) Calcd for $C_{18}H_{27}NO_{11}$ m/z: [M+Cl]− 468.1278; Found: m/z 468.1290, [M+HCOO]− 478.1566; Found m/z 478.1569.

Compound 5C. The same procedure for 5A was followed, using compound 22 (150 mg, 0.35 mmol) and 4-vinylbenzaldehyde (55 mg, 0.42 mmol) to afford 5C as a white powder (136 mg, 72%). H NMR (600 MHz, 298 K, CD$_3$OD) δ 8.57 (s, 1H), 7.90 (d, J=7.8 Hz, 2H), 7.58 (d, J=7.8 Hz, 2H), 7.28 (d, J=8.4 Hz, 2H), 7.18 (d, J=8.4 Hz, 2H), 6.83 (m, 1H), 5.94 (m, 1H), 5.37 (m, 1H), 5.24 (m, 1H), 4.98 (d, J=7.8 Hz, 1H), 3.96-3.93 (m, 11H), 3.90-3.86 (m, 4H), 3.80-3.75 (m, 2H), 3.71-3.64 (m, 4H), 3.62-3.54 (m, 2H), 3.51-3.49 (m, 1H), 3.32-3.29 (m, 5H). $^{13}$C NMR (150 MHz, 298 K, CD$_3$OD) δ 159.62, 156.38, 145.94, 140.62, 136.08, 135.78, 135.46, 129.69, 128.71, 126.44, 126.24, 121.80, 117.89, 117.11, 116.50, 116.28, 114.70, 101.54, 100.93, 79.50, 76.25, 75.32, 73.64, 73.42, 73.09, 72.73, 70.14, 61.33, 60.53. HRMS (ESI−/QTOF) Calcd for $C_{27}H_{33}NO_{11}$ m/z: [M−H]− 546.1981; Found 546.2021, [M+Cl]− 582.1748; Found 582.1802, [M+HCOO]− 592.2036; Found: m/z 592.2088.

Figure 25:
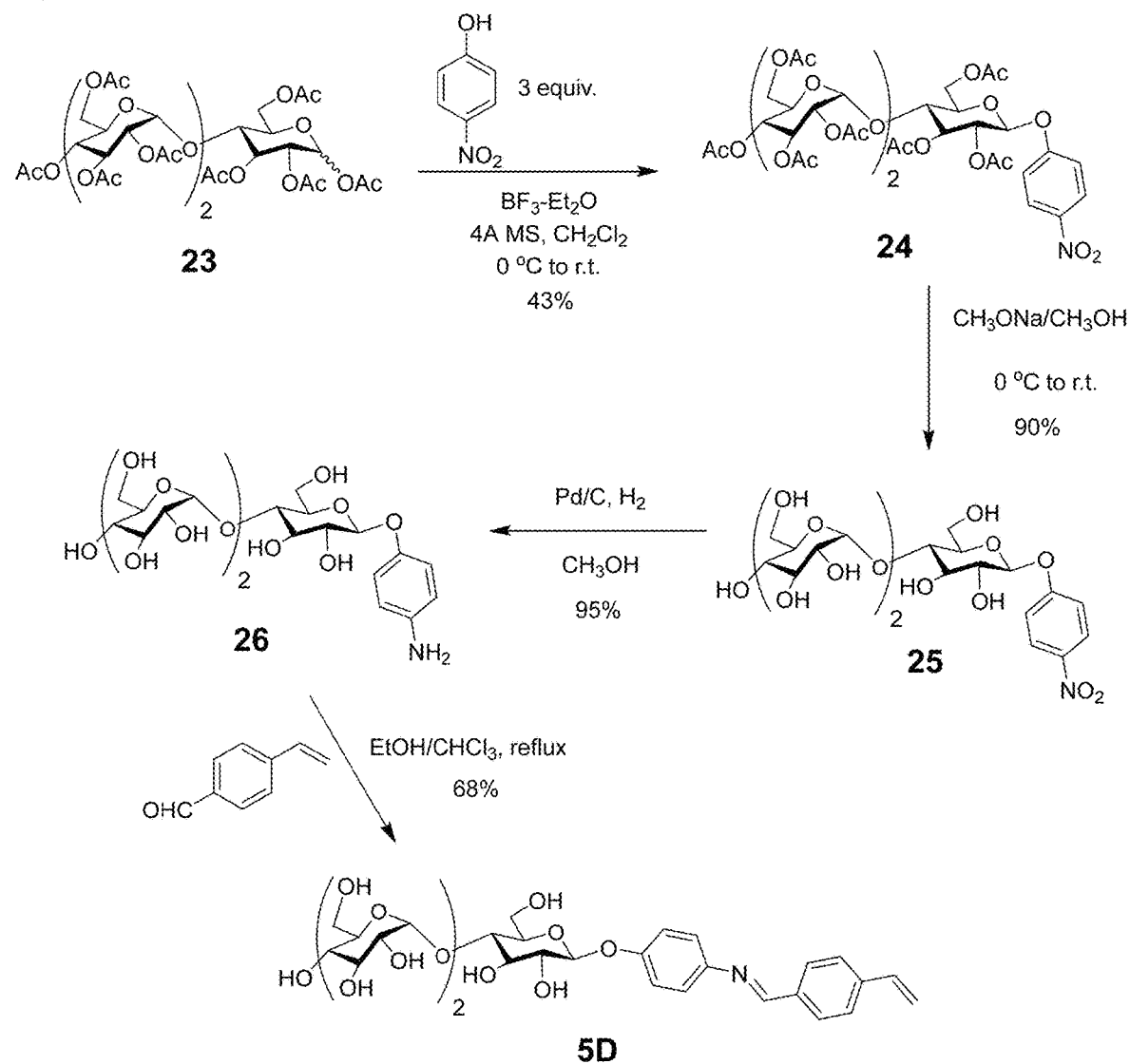
FIG. 25 is the synthesis of template 5D.

Synthesis of 5D (FIG. 25)

Compound 24. The same procedure for 20 was followed, using D-maltotriose acetate 23 (600 mg, 0.62 mmol) and 4-nitrophenol (259 mg, 1.86 mmol) to afford 24 as a colorless syrup (201 mg, 43%). $^1$H NMR (600 MHz, 298 K, CDCl$_3$) δ 8.15 (d, J=9.0 Hz, 2H), 7.02 (d, J=9.0 Hz, 2H), 5.39-5.28 (m, 2H), 5.23 (d, J=7.2 Hz, 1H), 5.11-5.07 (m, 1H), 5.02-4.98 (m, 1H), 4.83-4.80 (m, 1H), 4.46-4.43 (m, 1H), 4.23-4.18 (m, 2H), 4.07-4.00 (m, 3H), 3.93-3.91 (m, 2H), 2.05 (s, 3H), 2.04 (s, 3H), 2.03 (s, 3H), 2.01 (s, 3H), 1.99 (s, 3H), 1.98 (s, 3H), 1.96 (s, 3H). $^{13}$C NMR (125 MHz, 298 K, CDCl$_3$) δ 170.41, 170.16, 170.14, 170.06, 169.88, 169.43, 169.32, 161.06, 143.17, 125.74, 116.57, 97.43, 95.73, 74.95, 74.93, 72.61, 72.58, 71.63, 69.99, 69.19, 68.64, 67.99, 62.63, 61.54, 20.95, 20.83, 20.81, 20.62, 20.53, 20.51, 20.50. HRMS (ESI+/QTOF) Calcd for $C_{44}H_{55}NO_{28}$ m/z: [M+NH$_2$]+ 1063.3249; Found 1063.3253.

Compound 25. The same procedure for 21 was followed, using compound 24 (500 mg, 0.48 mmol) to afford 25 as a white powder (282 mg, 90%). 4H NMR (400 MHz, 298 K, CD$_3$OD) δ 8.21 (d, J=9.2 Hz, 2H), 7.24 (d, J=9.2 Hz, 2H), 5.21 (d, J=3.6 Hz, 1H), 5.11 (d, J=5.2 Hz, 1H), 4.49 (d, J=8.0 Hz, 1H), 3.88-3.80 (m, 8H), 3.78-3.69 (m, 8H), 3.54-3.49 (m, 15H), 3.34-3.30 (m, 3H). $^{13}$C NMR (100 MHz, 298 K, CD$_3$OD) δ 162.37, 142.49, 125.21, 116.31, 101.48, 101.25, 96.72, 92.42, 80.40, 79.88, 79.82, 79.23, 76.11, 75.50, 73.66, 73.57, 73.52, 73.36, 72.80, 72.32, 72.04, 71.98, 70.07, 6130, 60.76, 60.49. HRMS (ESI−/QTOF) Calcd for $C_{24}H_{35}NO_{18}$ m/z: [M+HCOO]− 670.1836; Found: m/z 670.1857.

Compound 26. The same procedure for 4-aminophenyl-β-D-glucopyranoside was followed, using compound 25 (400 mg, 0.64 mmol) to afford 26 as a white powder (354 mg, 95%). $^1$H NMR (400 MHz, 298 K, CD$_3$OD) δ 6.91 (d, J=8.8 Hz, 2H), 6.68 (d, J=8.8 Hz, 2H), 5.20-5.15 (m, 1H), 4.74 (d, J=7.6 Hz, 1H), 4.48 (d, J=7.6 Hz, 1H), 3.89-3.70 (m, 15H), 3.68-3.58 (m, 5H), 3.52-3.34 (m, 5H), 3.30-3.26 (m, 5H) $^{13}$C NMR (100 MHz, 298 K, CD$_3$OD) δ 150.72, 142.16, 117.89, 116.26, 102.13, 101.41, 96.74, 92.42, 80.42, 79.90, 79.86, 79.57, 76.27, 75.24, 75.19, 73.66, 73.34, 73.23, 73.16, 72.82, 72.35, 72.04, 71.93, 71.87, 70.22, 70.05, 61.03, 60.72. HRMIS (ESI/QTOF) Calcd for $C_{24}H_{37}NO_{16}$ m/z: [M+Cl]− 630.1806; Found 630.1847, [M+HCOO]− 640.2094; Found 640.2134.

Compound 5D. The same procedure for 5A was followed, using compound 26 (100 mg, 0.17 mmol) and 4-vinylbenzaldehyde (27 mg, 0.20 mmol) to afford 5D as a white powder (81 mg, 68%). $^1$H NMR (600 MHz, 298 K, CD$_3$OD) δ 8.54 (s, 1H), 7.86 (d, J=8.4 Hz, 2H), 7.55 (d, J=8.4 Hz, 2H), 7.25 (d, J=9.2 Hz, 2H), 7.15 (d, J=9.2 Hz, 2H), 6.79 (m, 1H), 5.90 (m, 1H), 5.34 (m, 1), 5.24 (m, 1H), 5.22 (d, J=3.6 Hz, 11H), 5.16-5.14 (m, 4H), 5.10 (d, J=3.6 Hz, 1H), 4.95 (d, J=8.0 Hz, 1H), 4.49 (d, J=8.0 Hz, 1H), 3.90-3.68 (m, 8H), 3.68-3.59 (m, 5H), 55-3.45 (m, 5H), 3.34-3.30 (m, 4H), 3.19-3.15 (m, 1H). $^{13}$C N-MR (150 MHz, 298 K, CD$_3$OD) δ 159.66, 156.40, 145.95, 140.64, 136.09, 135.48, 128.70, 126.24, 121.79, 117.12, 114.68, 101.48, 101.45, 101.41, 101.26, 100.91, 96.73, 92.42, 80.41, 80.01, 79.85, 75.23, 74.43, 73.66, 73.57, 73.52, 73.33, 73.32, 72.94, 72.50, 72.35, 72.03, 71.89, 70.23, 70.06, 61.31, 60.76. HRMS (ESI−/QTOF) Calcd for $C_{33}H_{43}NO_{16}$ m/z: [M−H]− 708.2509; Found 708.2484, [M+Cl]− 744.2276; Found 744.2247, [M+HCOO]− 754.2564, Found 754.2578.

Figure 26:
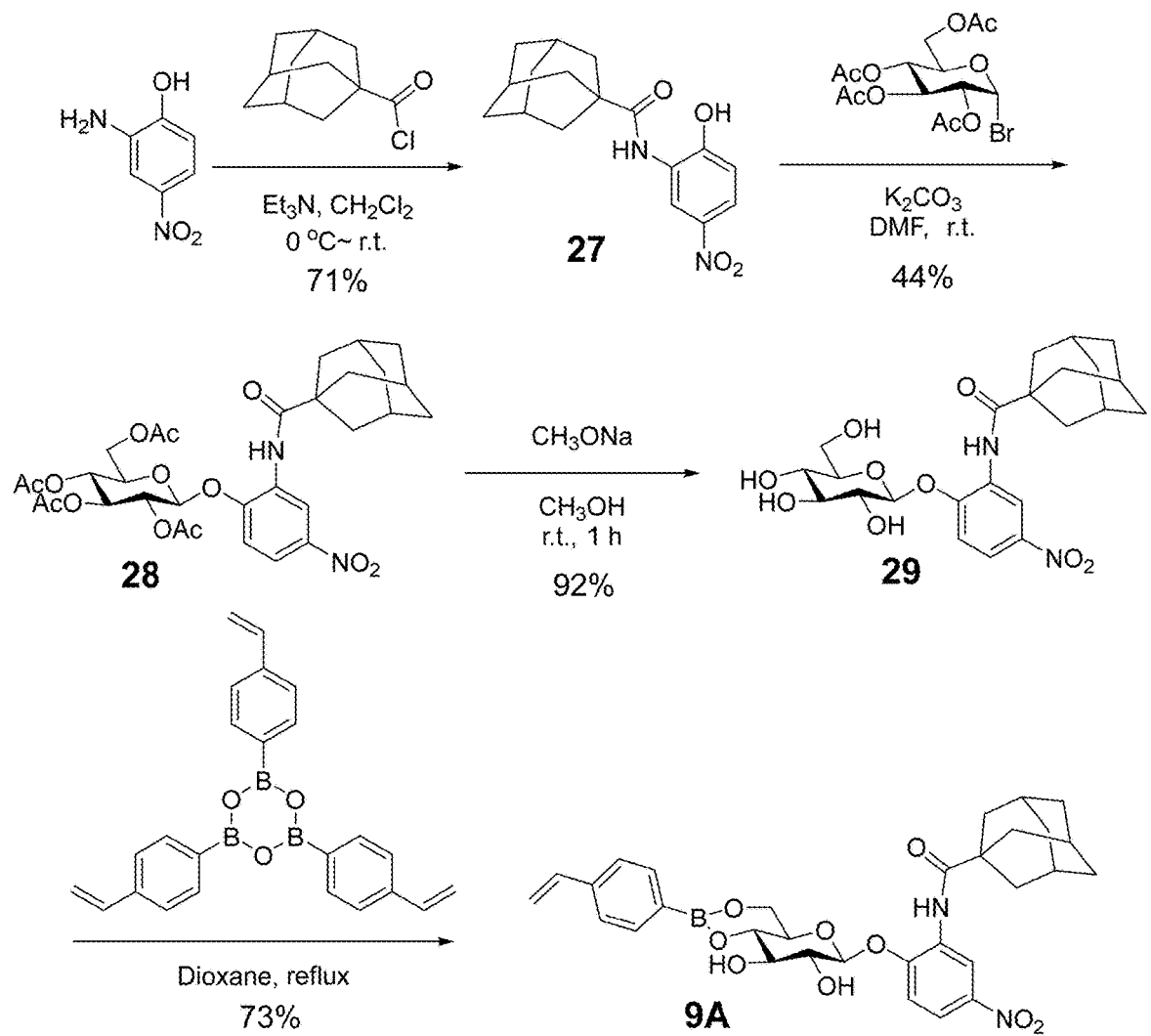
FIG. 26 is the synthesis of 9A.

Synthesis of 9A (FIG. 26)

Compound 27. A catalytic amount of dry DMF was added to a solution of adamantane-1-carboxylic acid (2.0 g, 11.1 mmol) and oxalyl chloride (1.90 mL, 22.2 mmol) in dry dichloromethane (30 mL). The mixture was stirred for 30 min at room temperature and then heated to reflux for an additional 30 min. After the solvent and oxalyl chloride were thoroughly removed through rotary evaporation, the residue was dissolved in dry dichloromethane (25 mL) and added dropwise to a solution of 2-aminophenol (1.8 g, 11.6 mmol) and Et$_3$N (6.47 mL, 46.4 mmol) in dry dichloromethane (30 mL) at 0° C. After warmed to room temperature and stirred for 6 h, the reaction was quenched by water and extracted with ethyl acetate (3×80 mL). The combined organic layers were washed with 1M HCl, water, and brine, dried over Na$_2$SO$_4$, and concentrated in vacuo. The residue was dissolved in a minimal amount of Dichloromethane and triturated with ethyl acetate to afford a light yellow solid (4.61 g, 71%)$^1$H NMR (600 MHz, CDCl$_3$): δ (ppm) 11.75 (s, 1H), 8.89 (d, J=3.0 Hz, 1H), 8.49 (s, 1H), 7.93 (dd, $J_1$=9.0 Hz, $J_1$=3.0 Hz, 1H), 7.06 (d, J=9.0 Hz, 1H), 2.05 (m, 3H), 1.93 (m, 6H), 1.73 (m, 6H).

Compound 28. A mixture of compound 27 (385 mg, 1.21 mmol) and $K_2CO_3$ (670 mg, 4.84 mmol) was stirred in dry DMF (15 mL) at room temperature for 15 min before acetobromo-α-D-glucose (600 mg, 1.46 mmol) in dry DMF (5 mL) was added. The reaction mixture was stirred for 24 h at room temperature. The solid was removed by filtration and the solution was concentrated in vacuo. The residue was purified by column chromatography with 10:1 chloroform/ethyl acetate as the eluent to give a white powder (344 mg, 44%). $^1$H NMR (400 MHz, $CDCl_3$): 9.42 (s, 1H), 7.95 (d, J=3.0 Hz, 1H), 7.90 (d, J=9.0 Hz, 1H), 6.98 (dd, $J_1$=9.0 Hz, $J_2$=3.0 Hz, 1H), 6.63 and 5.55 (d, J=2.0 Hz, 1H), 5.45-5.34 (m, 1H), 5.26-5.15 (m, 1H), 4.44-4.39 (m, 2H), 4.23-4.15 (m, 1H), 398-3.94 (m, 1H), 2.09 (—OAc, s, 3H), 2.08 (—OAc, s, 3H), 2.07 (—OAc, s, 3H), 2.06 (—OAc, s, 3H), 2.05 (m, 3M), 1.93 (m, 6H), 1.73 (m, 6H); $^{13}$C NMR (150 MHz, $CDCl_3$): 176.71, 170.30, 169.91, 169.53, 169.47, 169.43, 169.33, 148.90, 143.39, 139.23, 129.20, 127.36, 118.75, 115.95, 112.62, 98.37, 74.11, 72.57, 72.12, 70.70, 67.90, 67.45, 66.31, 61.64, 60.93, 42.07, 38.84, 36.24, 28.10, 20.73, 20.70, 20.63, 20.52, 20.47; HRMS (ESI$^+$/QTOF) Calcd for $C_{31}H_{38}N_2O_{13}$ m/z: [M+H]$^+$ 674.2447; Found 674.2448.

Compound 29. A solution of compound 28 (150 mg, 0.29 mmol) in methanol (10 mL) with a catalytic amount of sodium methoxide was stirred at room temperature for 2 h. The solution was neutralized with Amberlite® IR-120 (H$^+$) ion-exchange resin, filtered, and concentrated in vacuo. The residue was purified by column chromatography over silica gel using a mixture of dichloromethane and methanol (5:1) as the eluent to give a white powder (106 mg, 90%) $^1$H NMR (600 MHz, $CDCl_3$/$CD_3OD$, v/v, 5/1): 9.08 (d, J=: 3.0 Hz, 1H), 8.47 (N—H, s, 1H), 7.88 (dd, $J_1$=9.0 Hz, $J_2$=3.0 Hz, 1H), 7.23 (d, J=9.0 Hz, 1H), 4.86 (d, J=7.8 Hz, 1H), 3.85-3.82 (m, 1H), 3.73-3.70 (m, 1H), 3.54-3.38 (m, 4H), 2.02 (m, 3H), 1.90 (m, 6H), 1.70 (m, 6H); $^{13}$C NMR (150 MHz, $CDCl_3$): 177.53, 151.51, 143.13, 129.43, 119.79, 116.40, 116.03, 102.29, 76.81, 76.66, 73.23, 69.71, 41.96, 38.79, 36.24, 28.05; HRMS (ESI$^-$/QTOF) Calcd for $C_{23}H_{30}N_2O_9$ m/z: [M+Cl]$^-$, 513.1645; Found, 513.1668.

Template 9A. Compound 29 (180 mg, 0.38 mmol) and tris(4-vinylphenyl)boroxine (49 mg, 0.13 mmol) were mixed in 10 mL of 1,4-dioxane. The azeotrope was distilled for 4 h until a clear solution was obtained. After the solvent was removed in vacuo, the residue was recrystallized from a mixture of 1:4 dichloromethane/hexane to yield a white crystalline solid (166 mg, 74%). $^1$H NMR (600 MHz, $CDCl_3$/$CD_3OD$, 5/1, v/v) δ 9.13 and 8.45 (N—H, 1H), 7.86-7.62 (m, 2H), 7.49-7.32 (m, 1H), 7.22-7.03 (m, 4H), 6.64-6.60 (m, 1H), 5.73-5.69 (m, 1H), 5.20-5.17 (m, 1H) 4.95-4.84 and 4.25-4.22 (m, 1H), 3.94-3.26 (m, 6H), 2.02 (m, 3H), 1.89 (m, 6H), 1.70 (m, 6H); $^{13}$C NMR (150 MHz, $CDCl_3$/$CD_3OD$, 5/1, v/v) δ: 177.42, 170.51, 163.20, 160.67, 151.11, 143.53, 140.19, 138.66, 137.69, 136.69, 134.20, 13353, 128.84, 128.04, 125.35, 125.28, 125.11, 119.54, 116.82, 116.32, 114.59, 114.23, 103.23, 102.19, 76.73, 76.56, 73.59, 69.61, 63.73, 6129, 41.93, 41.88, 38.77, 38.72, 36.16, 27.96, 21.12; HRMS (ESI$^-$/QTOF) Calcd for $C_{31}H_{35}BN_2O_9$ m/z: [M+Cl]$^-$ 625.2130; Found, 625.2181; [M+HCOO]$^-$ 635.2418; Found, 635.2477.

Figure 27:
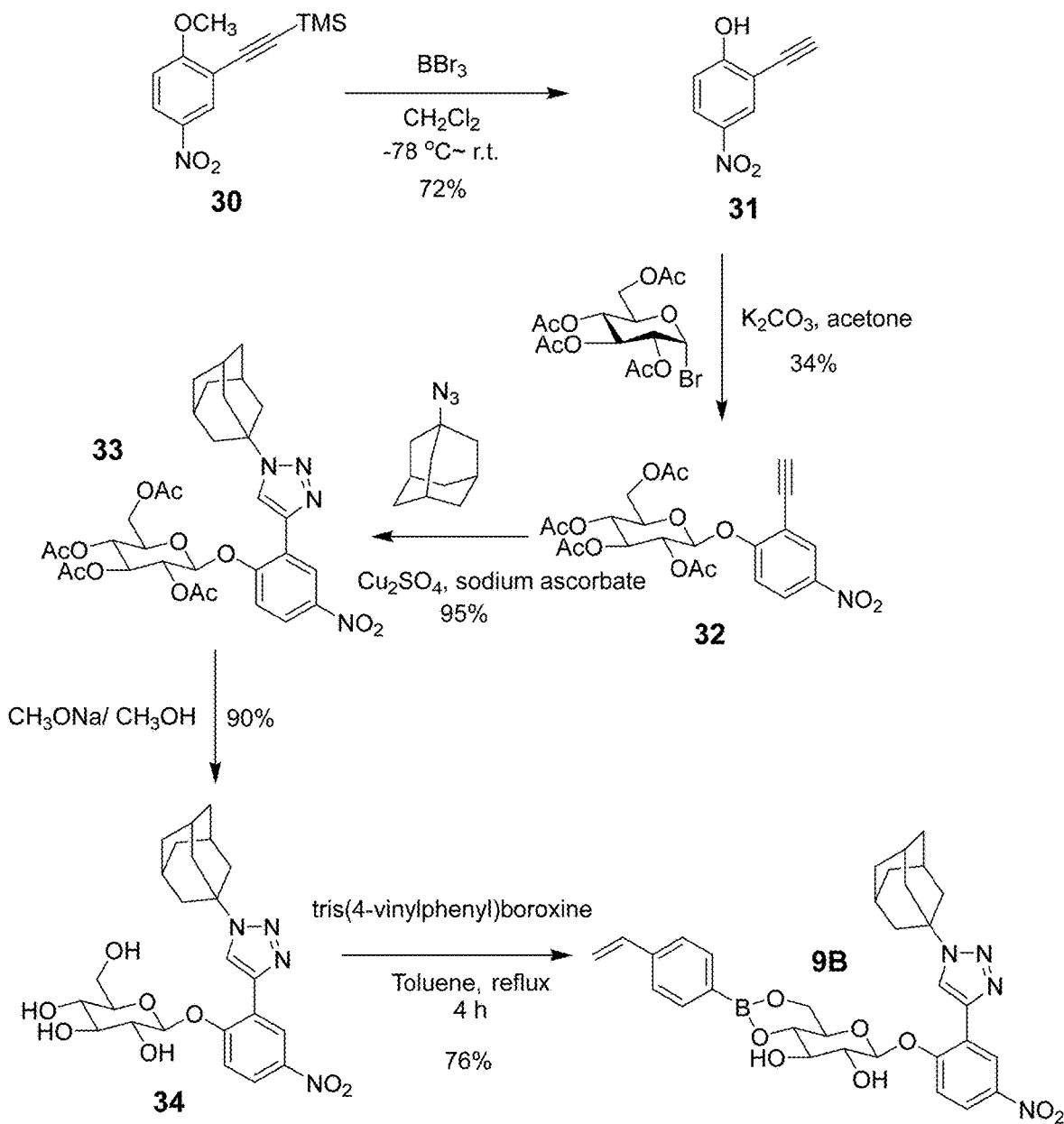
FIG. 27 is the synthesis of 9B.

Synthesis of 9B (FIG. 27)

Compound 31. Boron tribromide in dichloromethane (1M, 25 mL, 25 mmol) was added slowly to a solution of compound 30 (2.10 g, 8.42 mmol) in dry dichloromethane (100 mL) at −78° C. The reaction mixture was allowed to warm to room temperature and was stirred for 12 h. The reaction was quenched with a 1 M $NaHSO_4$ solution (5 mL). The organic solution was filtered through a pad of Celite and washed with ethyl acetate (100 mL). The filtrate was washed with saturated $NH_4Cl$ (2×100 mL) and brine (1×100 mL), and dried with anhydrous $Na_2SO_4$, and concentrated in vacuo. The residue was purified by column chromatography using 4:1 hexane/ethyl acetate as the eluent to afford a brown solid (989 mg, 72%). $^1$H NMR (600 MHz, 298 K, $CD_3COCD_3$) δ 10.18 (s, br, 1H), 8.27 (d, J=3.0 Hz, 1H), 8.17 (dd, $J_1$=9.0 Hz, $J_1$=3.0 Hz, 1H), 7.17 (d, J=9.0 Hz, 1H), 4.00 (s, H); $^{13}$C NMR (125 MHz, 298 K, $CD_3COCD_3$) δ 164.05, 140.47, 129.21, 126.05, 115.96, 110.38, 84.41, 77.41; FIRMS (ESI$^-$/QTOF) Calcd for $C_8H_5NO_3$ m/z. [M−H]$^-$ 16:2.0197, Found 162.0198.

Compound 32. Acetobromo-glucose (908 mg, 2.21 mmol) in dry acetone (5 mL) was added with vigorous stirring to a mixture compound 31 (300 mg, 1.84 mmol) and $K_2CO_3$ (1.02 g, 7.36 mmol) in dry acetone (25 mL) at 0° C. After the reaction mixture was stirred at room temperature for 12 h, the organic solvent was removed in vacuo. Ethyl acetate (50 mL) was added to the residue and the organic layer was washed with 0.5 M NaOH (2×100 mL) solution. The aqueous layer was extracted with ethyl acetate (2×50 mL). The combined organic phase was dried over anhydrous $Na_2SO_4$ and concentrated in vacuo. The residue was purified by column chromatography using 4:1 hexane/ethyl acetate as the eluent to afford a white crystal (310 mg, 34%). $^1$H NMR (600 MHz, 298 K, $CDCl_3$): δ 8.34 (d, J=2.4 Hz, 1H), 8.20 (dd, $J_1$=9.0 Hz, $J_2$=2.4 Hz, 1H), 7.18 (d, J=9.0 Hz, 1H), 5.40 (m, 1H), 5.33 (m, 1H), 5.22 (m, 2H), 4.31-4.21 (m, 2H), 3.96 (m, 1H), 3.39 (s, 1H), 2.10 (s, 3H), 2.08 (s, 3H), 2.07 (s, 3H) 2.06 (s, 3H): $^{13}$C NMR (150 MHz 298 K $CDCl_3$): δ 170.40, 170.13, 169.32, 168.96, 16211, 142.80, 129.48, 125.60, 115.24, 114.18, 98.93, 84.35, 76.39, 72.51, 72.21, 70.49, 68.01, 61.78, 20.68, 20.67, 20.58, 20.56. FIRMS (ESI$^-$/QTOF) Calcd for $C_{22}H_{23}NO_{12}$ m/z: [M+COO]$^-$ 538.1202; Found 538.1230.

Compound 33. Sodium ascorbate (116 mg, 0.59 mmol) and $Cu(OAc)_4·H_2O$ (73 mg, 0.294 mmol) were added to a solution of compound 32 (100 ng, 0.294 mmol) and 1-azidoadamantane (67 mg, 0.294 mmol) in $CH_3OH$/THF/HO (2.5 mL/2.5 mL/5 mL). After the mixture was stirred overnight at room temperature, the mixture was diluted with dichloromethane (30 mL) and washed with water (2×50 mL) and brine (1×50 mL). The combined organic solution was dried over $Na_2SO_4$ and concentrated in vacuo. The residue was purified by column chromatography using 4:1 hexane/ethyl acetate as the eluent to afford a white powder (158 mg, 95%). $^1$H NMR (400 MHz, 298 K, $CDCl_3$): δ 9.21 (d, J=2.8 Hz, 1H), 8.12 (dd, $J_1$=9.2 Hz, $J_2$=28.1 Hz, 1H), 8.00 (s, 1H), 7.10 (d, J=9.2 Hz, 1H), 5.51-5.46 (m, 1H), 5.38-5.33 (m, 2H), 5.22-5.17 (M, 1H), 4.37-4.34 (m, 1H), 4.17-4.01 (m, 2H), 2.28 (m, 8H), 2.06 (s, 3H), 2.04 (s, 3H), 2.03 (s, 3H) 2.01 (s, 3H), 1.82 (m, 7H); $^{13}$C NMR (100 MHz, 298 K, $CDCl_3$): δ 170.40, 169.95, 169.43, 169.38, 158.36, 143.41, 139.28, 124.10, 123.69, 122.19, 120.77, 113.70, 97.94, 72.48, 70.36, 67.68, 61.71, 60.17, 42.52, 35.86, 29.05, 20.67, 20.54, 20.53, 20.50; HRMS (ESI$^+$/QTOF) Calcd for $C_{32}H_3N_4O_{12}$ m/z: [M+H]$^+$ 671.2558; Found 671.2571; [M+NH$_4$]$^+$ 688.2824; Found 688.2867.

Compound 34. A solution of compound 33 (150 mg, 0.29 mmol) in methanol (10 mL) with a catalytic amount of sodium methoxide was stirred at room temperature for 2 h. The solution was neutralized with Amberlite® IR-120 (H$^+$) ion-exchange resin, filtered, and concentrated in vacuo. The residue was purified by column chromatography over silica gel using a mixture of dichloromethane and methanol (5:1) as the eluent to give the final product 34 as a white powder (106 mg, 90%). $^1$H NMR (400 MHz, 298 K, CDCl$_3$/CD$_3$OD, 1/5, v/v): δ 8.96 (d, J=2.8 Hz, 1H), 8.67 (s, 1H), 8.18 (dd, J$_1$=9.2 Hz, J$_2$=2.8 Hz, 1H), 7.47 (d, J=9.2 Hz, 1H), 5.18 (d, J=7.6 Hz, 1H), 3.95-3.92 (m, 1H). 3.79-3.57 (m, 2H), 3.56-3.51 (m, 1H), 3.46-3.44 (m, 1H), 4.17-4.01 (m, 1H), 2.30-2.27 (m, 6H), 1.91-1.84 (m, 6H), 1.25 (m, 3H); $^{13}$C NMR (100 MHz, 298 K, CDCl$_3$/CD$_3$OD, 1/5, v/v): δ 159.13, 153.50, 143.78, 129.38, 128.78, 125.10, 122.73, 124.10, 117.67, 116.70, 102.02, 74.45, 70.79, 63.88, 62.08, 58.39, 43.58, 36.58, 30.51; HRMS (ESI$^-$/QTOF) Calcd for C$_{24}$H$_{30}$N$_4$O$_8$ m/z: [M+Cl]$^-$ 537.1758; Found 537.1766; [M+HCOO]$^-$ 547.2046; Found 547.2054.

Template 9B. Compound 34 (50 mg, 0.10 mmol) and tris(4-vinylphenyl)boroxine (13 mg, 0.034 mmol) were mixed in 10 mL of 1,4-dioxane. The azeotrope was distilled for 4 h, and the remaining solvent was removed in vacuo. The product was crystallized from 1,4-dioxane and washed with cold ethanol to yield a white crystal (47 mg, 76%). $^1$H NMR (400 MHz, 298 K, DMSO-d$_6$): δ 8.94 (d, J=2.8 Hz, 1H), 8.67-8.61 (m, 1H), 8.22-8.19 (m, 1H), 8.08-8.06 (m, 1H), 7.74-7.4:2 (m, 4H), 6.78-6.67 (m, 1H), 5.92-5.80 (m, 1H), 5.33 (d, J=12.6 Hz, 1H), 5.29-5.25 (m, 1H), 4.25-4.22 (m, 1H), 3.86-3.39 (m, 5H), 3.39-3.28 (m, 2H), 3.28-3.17 (m, 1H), 2.25 (m, 6H), 1.80 (m, 6H), 1.35 (m, 3H); HRMS (ESI$^-$/QTOF) Calcd for C$_{32}$H$_{35}$N$_4$O$_8$B m/z: [M−H]$^-$ 613.2475; Found 613.2430; [M+Cl]$^-$ 649.2242; Found 6492254.

Figure 28:
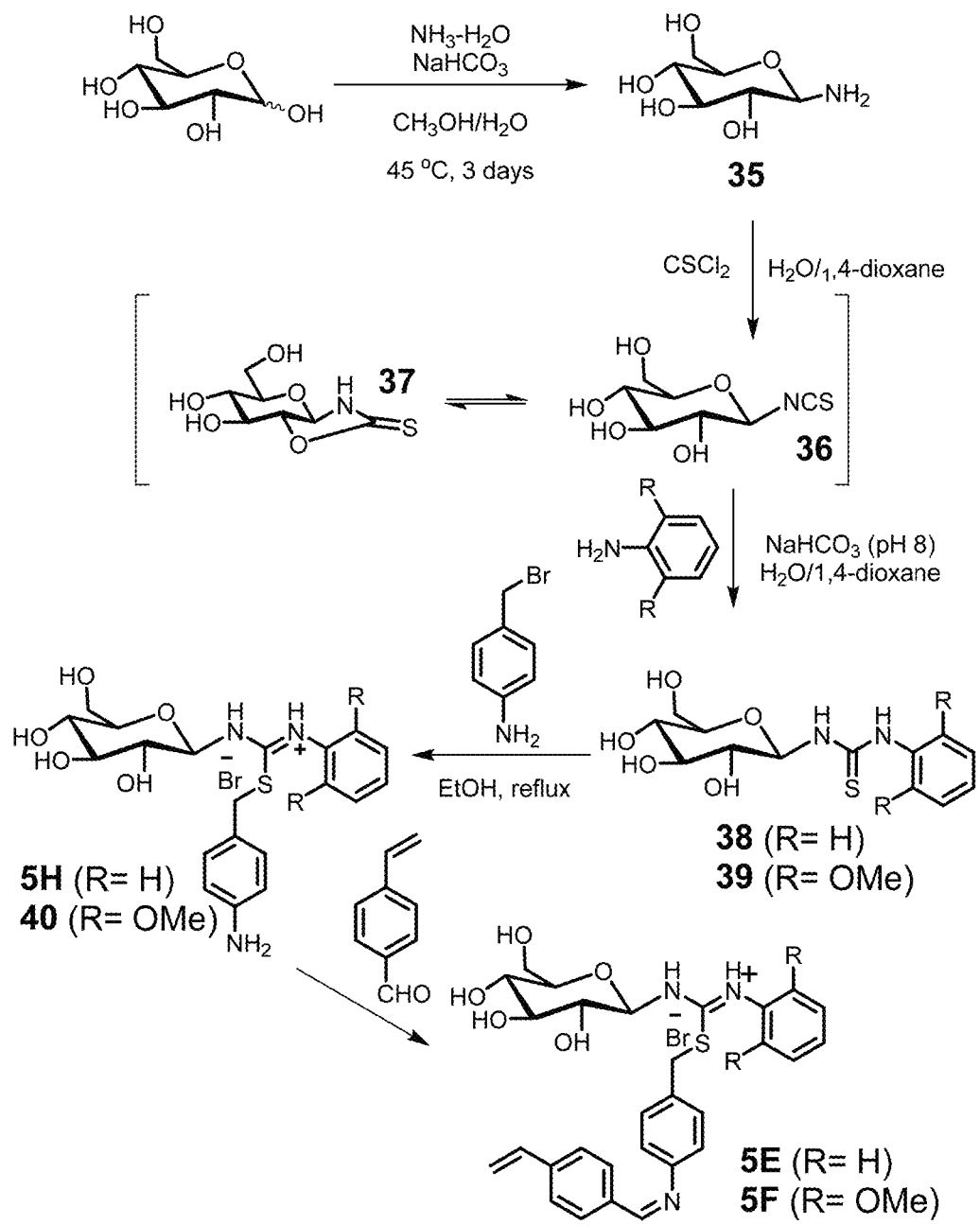
FIG. 28 is the synthesis of 5E, 5F, and 5H.

Synthesis of 5E, 5F, and 5H (FIG. 28)

Compound 38. Glucose (360 mg, 2.00 mmol) and ammonia bicarbonate (176 mg, 2.10 mmol) were dissolved in an ammonia hydroxide solution (20 mL). After the mixture was stirred at 45° C. for 3 d, the solvent was removed in vacuo and the residue was dried under vacuum for 4 h. The resultant compound 33 was used directly for the following reaction without further purification. $^1$H NMR (400 MHz, 298 K, D$_2$O) δ 4.92 (d, J=5.2 Hz, 1H), 3.91-3.89 (m, 1H), 3.71-3.66 (m, 1H), 3.47-3.39 (m, 3H), 3.34-3.30 (m, 1H). HRMS (ESI$^+$/QTOF) Calcd for C$_6$H$_{13}$NO$_5$ m/z: [M+H]$^+$ 180.0866; Found m/z 180.0867; (ESI$^-$/QTOF) Calcd for C$_6$H$_{13}$NO$_5$ m/z: [M+HCOO]$^-$ 224.0776; Found 224.0778.

Compound 35 (2.0 mmol) was dissolved in a 10 mL mixture of 1,4-dioxane/NaHCO$_3$ aqueous solution. Thiophosgene (CSCl$_2$, 161 μL, 2.1 mmol) was added to the stirred mixture at −5° C. After the reaction mixture was stirred at room temperature for 1 h, aniline (192 μL, 2.1 mmol) was added. After 24 h, solvents were removed in vacuo and the residue was purified by column chromatography over C-18 silica gel using CH$_3$CN/H$_2$O as the eluent (from ⅕ to ¼, v/v). The final product 38 was obtained as an off-white powder (352 mg, 56%). $^1$H NMR (400 MHz, 298 K, D$_2$O) δ 7.59-7.56 (m, 2H), 7.56-7.52 (m, 1H), 7.42 (dd, J$_1$=9.0 Hz, J$_2$=1.8 Hz, 2H), 5.11 (d, J=6.2 Hz, 1H), 3.94-3.92 (m, 1H), 3.75-3.72 (m, 1H), 3.55-3.41 (m, 3H), 3.34-3.33 (m, 1H). HRMS (ESI$^-$/QTOF) Calcd for C$_{13}$H$_{18}$N$_2$O$_6$S m/z: [M−H]$^-$ 313.0863; Found m/z 313.0865; [M+Cl]$^-$ 349.0630; Found 349.0636.

Compound 39. Compound 39 was synthesized following the same procedure for compound 38 using compound 35 (1.0 mmol) and 2,6-dimethoxyaniline (1.1 mmol) instead of aniline. The final product was obtained as an off-white powder (241 mg, 43%). $^1$H NMR (400 MHz, 298 K, CD$_3$OD) δ 7.59 (t, J=8.8 Hz, 1H), 7.46 (d, J=9.6 Hz, 2H), 5.03 (d, J=7.6 Hz, 1H), 4.14 (s, 6H), 3.90-3.89 (m, 1H), 3.85-3.81 (m, 2H), 3.79-3.71 (m, 2H), 3.60-3.56 (m, 1H).

HRMS (ESI$^-$/QTOF) Calcd for C$_{15}$H$_{22}$N$_2$O$_7$S m/z: [M−Br]$^-$ 419.1130; Found m/z 419.1164.

Compound 5E. A solution of compound 38 (100 mg, 0.32 mmol) and 4-(bromomethyl)aniline (66 mg, 0.35 mmol) in EtOH (10 mL) was heated to reflux for 12 h. After the reaction mixture was cooled to room temperature, 20 mL of dichloromethane (20 mL) was added. The precipitate was collected by filtration, washed with fresh dichloromethane (3×20 mL), and then dried under vacuum to afford compound 5H as a grey powder that was used in the next step directly. $^1$H NMR (400 MHz, 298 K, CD$_3$OD) δ 10.62 (s, br, 2H), 8.24 (d, J=9.0 Hz, 2H), 7.82 (t, J=9.0 Hz, 2H), 7.23 (m, 1H), 6.92 (d, J=8.4 Hz, 2H), 6.48 (d, J=8.4 Hz, 2H), 5.58 (s, br, 2H), 5.16 (d, J=5.6 Hz, 1H), 4.77 (s, 2H), 3.96-3.86 (m, 2H), 3.73-3.56 (m, 2H), 3.42-3.37 (m, 1H), 3.30-3.22 (m, 1H). HRMS (ESI$^+$/QTOF) Calcd for C$_{20}$H$_{26}$BrN$_3$O$_5$S m/z: [M−Br]$^+$ 420.1588; Found 420.1591. The resultant compound 5H was added to anhydrous EtOH (10 mL), followed by 4-vinylbenzaldehyde (86 mg, 0.35 mmol). The reaction mixture was heated under reflux under N$_2$ for 24 h. After the reaction mixture was cooled to room temperature, ether (20 mL) was slowly added. The mixture was cooled at 0° C. for 15 min. The greenish yellow precipitate was collected by filtration and washed with cold ether (3×30 mL) to afford the final product 5E as a light-yellow powder (140 mg, 71% over two steps). $^1$H NMR (400 MHz, 298 K, CD$_3$OD) δ 9.69 (s, br, 2H), 8.71 (s, 1H), 7.91-7.88 (m, 4H), 7.49 (d, J=8.4 Hz, 2H), 7.43 (d, J=8.4 Hz, 2H), 7.29 (m, 1H), 7.09 (m, 2H), 6.98 (m, 2H), 6.78 (m, 1H), 5.84 (d, J=17.6 Hz, 1H), 5.27 (d, J=11.2 Hz, 1H), 5.09 (m, 1H), 4.81 (d, J=9.6 Hz, 1H), 4.54 (s, 2H), 3.54-3.46 (m, 2H), 3.45-3.37 (m, 1H), 3.35-3.32 (m, 1H), 3.20-3.18 (m, 1H). $^{13}$C NMR (100 MHz, 298 K, CD$_3$OD) δ 169.35, 158.89, 151.87, 143.93, 137.20, 136.98, 136.92, 136.70, 133.80, 130.41, 128.48, 126.66, 121.80, 116.13, 114.98, 114.55, 102.40, 75.60, 71.63, 69.42, 68.70, 61.72, 61.08, 34.60. HRMS (ESI$^+$/QTOF) Calcd for C$_{29}$H$_{32}$BrN$_3$O$_5$S m/z: [M−Br]$^+$ 534.2057; Found m/z 534.2066.

Compound 5F. A solution of compound 39 (100 mg, 0.27 mmol) and 4-(bromomethyl)aniline (57 mg, 0.30 mmol) in EtOH (10 mL) was heated to reflux for 12 h. After the reaction mixture was cooled to room temperature, 20 mL of dichloromethane (20 mL) was added. The precipitate was collected by filtration, washed with fresh dichloromethane (3×20 mL), and then dried under vacuum to afford compound 40 (141 mg, 78%) as a grey powder that was used in the next step directly. $^1$H NMR (400 MHz, 298 K, DMSO-d$_6$) δ 9.76 (s, br, 2H), 7.59 (d, J=9.2 Hz, 4H), 7.47 (d, J=9.2 Hz, 2H), 7.24 (d, J=8.4 Hz, 2H), 7.07 (t, J=8.4 Hz, 1H), 5.77 (m, 1H), 5.33 (m, 2H), 5.15 (m, 1H), 4.69 (s, 2H), 4.21 (m, 6H), 3.69-3.53 (m, 5H), 3.44-3.38 (m, 2H), 3.29-3.22 (m, 2H). HRMS (ESI$^+$/QTOF) Calcd for C$_{22}$H$_{30}$BrN$_3$O$_7$S m/z: [M−Br]$^+$ 480.1799; Found m/z 480.1803. The resultant compound 40 was added to anhydrous EtOH (10 mL), followed by 4-vinylbenzaldehyde (74 mg, 0.30 mmol). The reaction mixture was heated under reflux under N$_2$ for 24 h. After the reaction mixture was cooled to room temperature, ether (20 mL) was slowly added. The mixture was cooled at 0° C. for 15 min. The greenish yellow precipitate was collected by filtration and washed with cold ether (3×30 mL) to afford the final product 5F as a light-yellow powder (97 mg, 54% over two steps). $^1$H NMR (400 MHz, 298 K, CD$_3$OD) δ 8.87 (s, 1H), 8.26 (d, J=9.2 Hz, 2H), 7.84 (d, J=8.0 Hz, 2H), 7.79 (d, J=8.0 Hz, 2H), 7.57 (t, J=8.4 Hz, 1H), 7.32 (d, J=9.2 Hz, 2H), 7.11 (d, J=8.4 Hz, 2H), 6.53 (m, 1H), 6.01 (d, J=17.6 Hz, 1H), 5.67 (d, J=4.2 Hz, 1H), 5.42 (d, J=10.8 Hz, 1H), 4.61 (s, 2H), 4.14 (s, 6H), 3.82-3.77 (m, 1H), 3.74-3.49 (m, 4H), 3.46-3.41 (m, 1H). HRMS (ESI$^+$/QTOF) Calcd for $C_{31}H_{36}BrN_3O_7S$ m/z: [M−Br]$^+$ 594.2268; Found m/z 594.2288.

Figure 29:
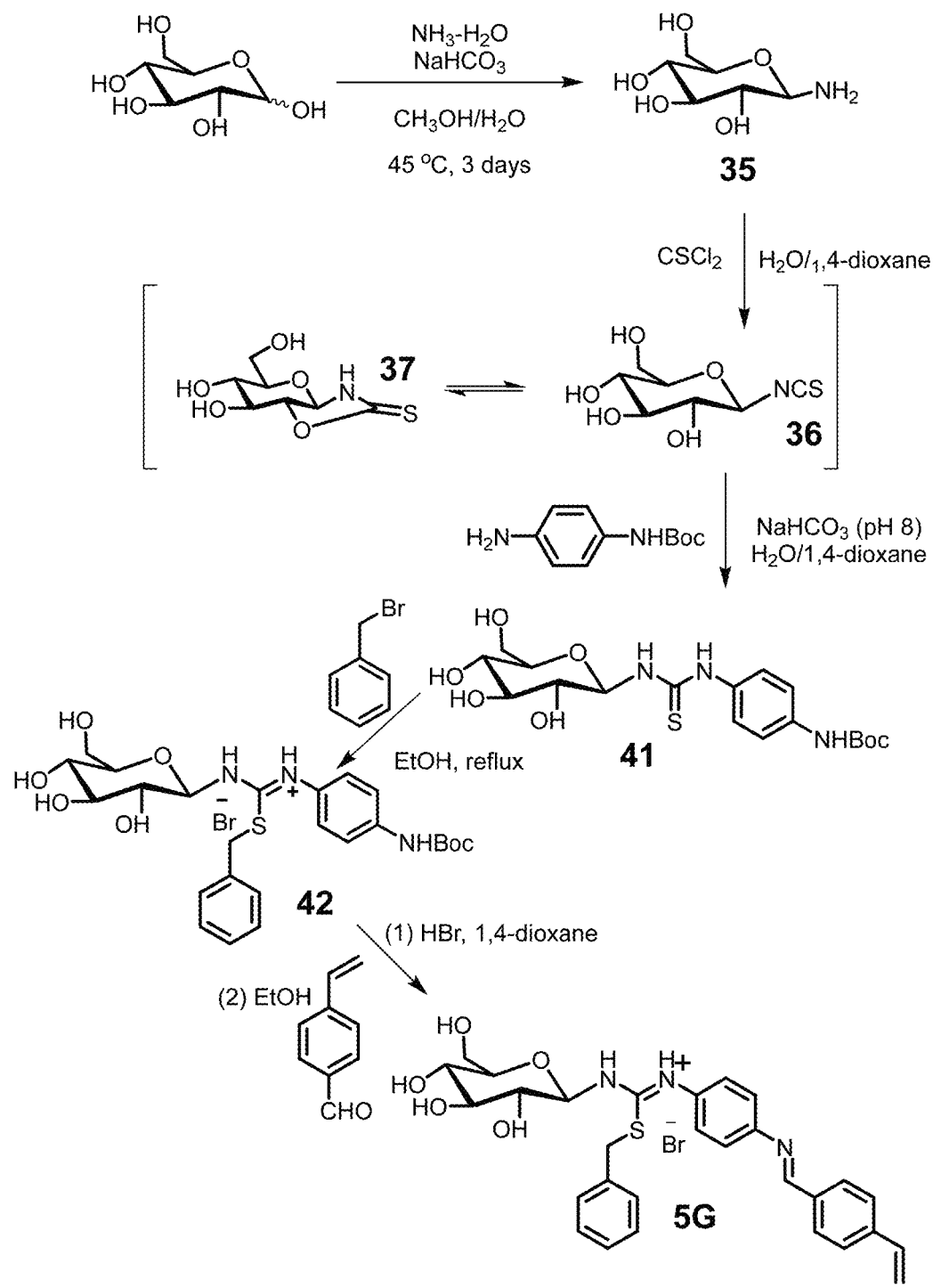
FIG. 29 is the synthesis of 5G.

Synthesis of 5G (FIG. 29)

Compound 41. Compound 41 was synthesized following the same procedure for compound 38 using N-Boc-p-phenylenediamine instead of aniline. The final product was obtained as an off-white powder (yield 56%). $^1$H NMR (400 MHz, 298 K, CD$_3$OD) δ 8.57 (s, br, 2H), 7.14 (d, J=8.0 Hz, 2H), 6.85 and 6.72 (d, J=8.0 Hz, 2H), 4.98 (s, br, 1H), 4.49 (d, J=8.8 Hz, 1H) 3.94-3.92 (m, 1H), 3.75-3.72 (m, 2H), 3.47-3.31 (m, 2H), 3.30-3.27 (m, 1H), 1.49 (s, 9H). $^{13}$C NMR (100 MHz, 298 K, CD$_3$OD) δ 178.47, 154.51, 142.68, 130.21, 120.53, 114.05, 85.98, 77.66, 76.99, 73.25, 71.13, 70.32, 61.31, 53.43, 27.38. HRMS (ESI$^-$/QTOF) Calcd for $C_{18}H_{27}N_3O_7S$ [M+Cl]$^-$ 464.1264; Found 364.1274.

Compound 5G. A solution of compound 41 (400 mg, 0.93 mmol) and benzyl bromide (954 mg, 663 µL, 5.60 mmol) in EtOH (10 mL) was heated to reflux for 12 h. After the reaction mixture was cooled to room temperature, 20 mL of dichloromethane (20 mL) was added. The precipitate was collected by filtration, washed with fresh dichloromethane (3×20 mL), and then dried under vacuum to afford compound 42 (141 mg, 78%) as a grey powder that was used in the next step directly. To a solution of compound 42 (100 mg, 0.167 mmol) in 1,4-dioxane (20 mL) was added 40% HBr (0.83 mmol, 5.0 equiv.) at 0° C. The reaction mixture was stirred under room temperature for 4 h and then the solvent was removed in vacuo. The residue was dissolved in methanol and co-evaporated with methanol (3×30 mL) in vacuo. The resultant powder (deprotected 42, 50 mg, 0.10 mmol) was dissolved in EtOH (5 mL), followed by the addition of 4-vinylbenzaldehyde (40 mg, 0.30 mmol). The reaction mixture was stirred at room temperature for 24 h and then the solvent was removed in vacuo. The residue was washed with ether (3×30 mL) and dried under vacuum to afford the final compound 5G as an off-white powder (49 mg, 79% over two steps). $^1$H-NMR (400 MHz, 298 K, CD$_3$OD/DMSO-d$_6$ 1/3, v/v): δ 9.11 (s, br, 2H), 8.67 (s, 1H), 7.46 (d, J=8.0 Hz, 2H), 7.39 (d, J=8.0 Hz, 2H) 7.27 (t, J=8.0 Hz, 1H), 7.14 (d, J=9.2 Hz, 2H), 7.06 (d, J=8.0 Hz, 2H), 6.95-6.93 (m, 2H), 6.75-6.67 (m, 1H), 6.57 (d, J=9.2 Hz, 2H), 5.82 (d, J=17.6 Hz, 1H), 5.24 (d, J=10.8 Hz, 1H), 5.06 (s, 2H), 4.25 (d, J=8.4 Hz, 1H), 3.64-3.61 (m, 1H), 3.52-3.39 (m, 2H), 3.25-3.23 (m, 1H), 3.20-3.16 (m, 2H), $^{13}$C-NMR (100 MHz, CDCl$_3$): 206.26, 169.28, 158.90, 153.39, 142.98, 137.20, 136.87, 136.63, 130.33, 130.10, 128.37, 126.57, 121.72, 116.03, 114.51, 113.64, 86.02, 78.68, 77.88, 77.56, 73.32, 70.54, 69.38, 61.27; HRMS (ESI$^+$/QTOF) Calcd for $C_{29}H_{32}BrN_3O_5S$ m/z: [M−Br]$^+$ 534.2057; Found 534.2068.

Illustrative Procedure for the Preparation of MINP(SA)

A solution of 6-vinylbenzoxaborole (4) in methanol (10 µL of a 6.4 mg/mL of stock solution, 0.0004 mmol) was added to imine template 5A in methanol (10 µL of a 0.04 mM of stock solution, 0.0004 mmol) in a vial containing methanol (5 mL). After the mixture was stirred for 6 h at room temperature, methanol was removed in vacuo to afford the final sugar-boronate templates 6A. A micellar solution of compound 1 (0.03 mmol), compound 2 (0.02 mmol), divinylbenzene (DVB, 2.8 µL, 0.02 mmol), and 2,2-dimethoxy-2-phenylacetophenone (DMPA, 10 µL of a 12.8 mg/mL solution in DMSO, 0.0005 mmol) in H$_2$O (2.0 mL) was added to the sugar-boronate complex. The mixture was subjected to ultrasonication for 10-15 min until the mixture become clear. Then CuCl$_2$ (10 µL of a 6.7 mg/mL solution in H$_2$O, 0.0005 mmol) and sodium ascorbate (10 µL of a 99 mg/mL solution in H$_2$O, 0.005 mmol) were added to the mixture. After the reaction mixture was stirred slowly at room temperature for 12 h, the reaction mixture was sealed with a rubber stopper, degassed with N$_2$ three times and purged with nitrogen for 15 min, and irradiated in a Rayonet reactor for 12 h. Compound 3 (10.6 mg, 0.04 mmol), CuCl$_2$ (10 µL of a 6.7 mg/mL solution in H$_2$O, 0.0005 mmol), and sodium ascorbate (10 µL of a 99 mg/mL solution in H$_2$O, 0.005 mmol) were added. The progress of reaction was monitored by $^1$H NMR spectroscopy and dynamic light scattering (DLS). After being stirred for another 6 h at room temperature, the reaction mixture was poured into acetone (8 mL). The precipitate collected by centrifugation was washed with a mixture of acetone/water (5 mL/1 mL) three times, followed by acetone (5 mL) two times before being dried in air to afford the MINP(5A). The solid was then rinsed with acetone (5 mL) two times and dried in air to afford the final MINPs. Typical yields were >80%.

Acid Functionalized MINP Catalysts. MINP(5A) obtained above was dissolved in 6 N HCl aqueous solution (2 mL) and the solution was stirred at 95° C. for 2 h. After cooled down to room temperature, the reaction mixture was poured into acetone (8 mL). The precipitate collected by centrifugation was washed with a mixture of acetone/water/CH$_3$OH (5 mL/1 mL/1 mL) three times, acetone (5 mL) twice, and dried in air. The resulting MINP-CHO(5A) (5 mg, 0.0001 mmol) was dissolved in dry DMF (0.5 mL), followed by the addition of 7D (10 µL of 0.1 M stock solution in DMSO, 0.001 mmol). After the reaction mixture was stirred at 50° C. for 6 h, borane-pyridine complex (10 µL of 0.1 M stock solution in dry DMF, 0.001 mmol) was added. The mixture was stirred at 50° C. overnight. After cooled down to room temperature, the DMF solution was poured into acetone (8 mL). The precipitate collected by centrifugation was washed with acetone/methanol (5 mL/1 mL), methanol/HCl (5 mL/0.1 mL, 1M) three times, acetone (5 mL) twice, and dried in air to afford the final MINP(5A+7D).

Figures 30A, 30B:
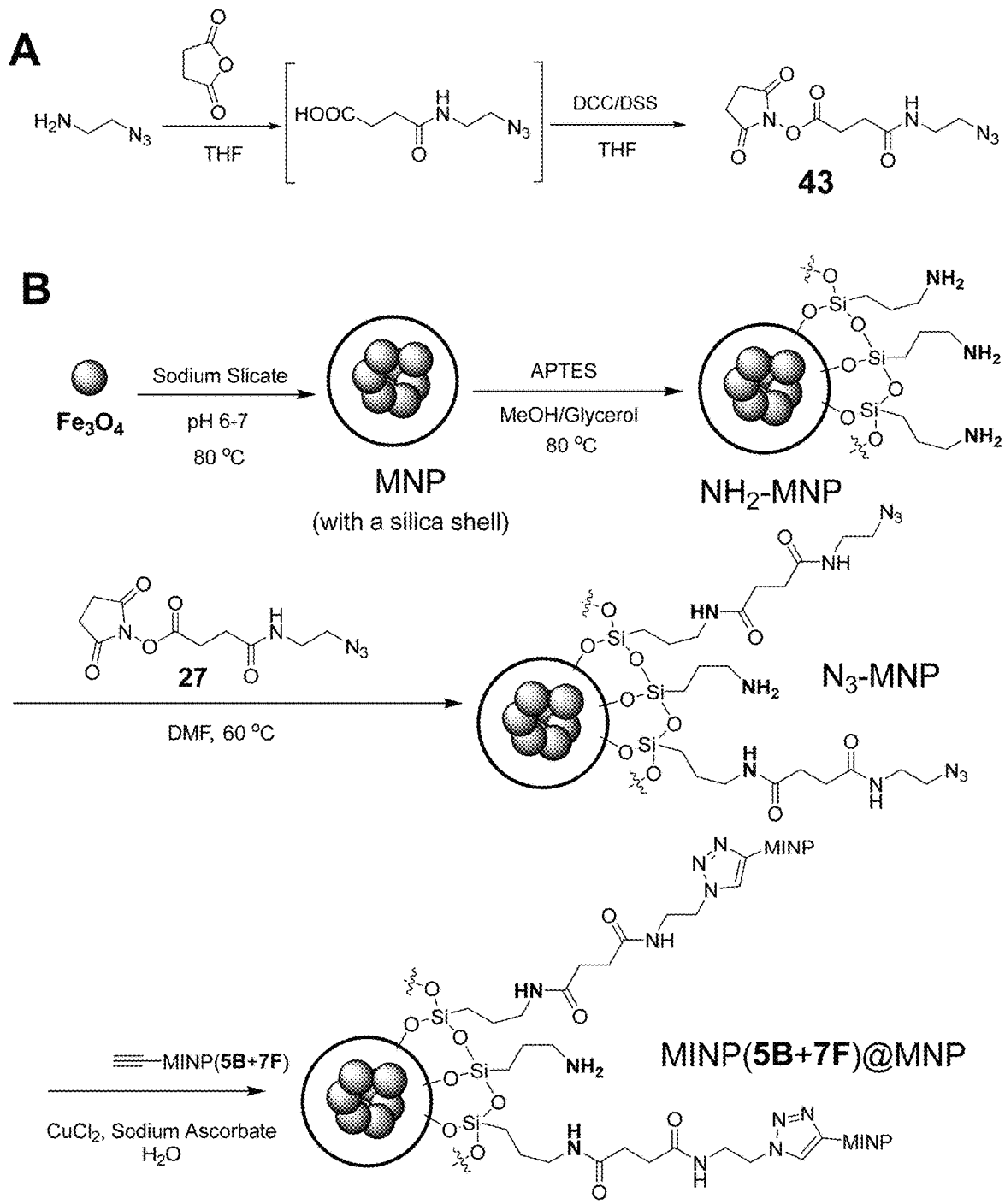
FIG. 30A is the synthesis of surface linker 43.
FIG. 30B is the preparation of MINP(5B+7F)@MNP as a recyclable catalyst.
Figures 31A, 31B, 31C:
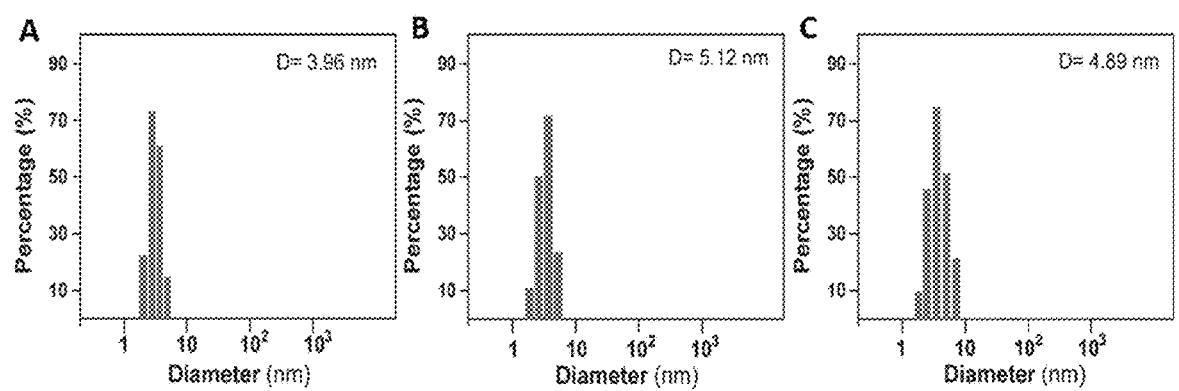
FIG. 31A is the distribution of the hydrodynamic diameters of the cross-linked micelles determined by dynamic light scattering (DLS) after step (a) in FIG. 1A in typical MINP preparation.
FIG. 31B is the distribution of the hydrodynamic diameters of the cross-linked micelles determined by dynamic light scattering (DLS) after step (b) in FIG. 1A in typical MINP preparation.
FIG. 31C is the distribution of the hydrodynamic diameters of the cross-linked micelles determined by dynamic light scattering (DLS) after step (c) in FIG. 1A in typical MINP preparation.
Figure 32:
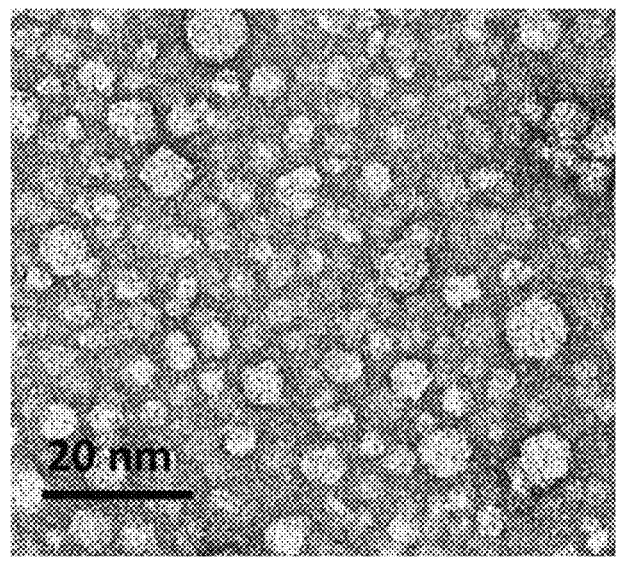
FIG. 32 is a TEM image of typical MINPs.

Preparation of MINP(5B+7F)@MNP (FIG. 30)

Compound 43. 2-Azidoethylamine (1.2 g, 13.94 mmol) was added to a solution of succinic anhydride (1.32 g, 13.24 mmol) and triethylamine (2.53 g, 25 mmol) in anhydrous dichloromethane (40 mL). After the reaction mixture was stirred at 35° C. overnight, diluted HCl (1 M, 50 mL) was added. The mixture was extracted with dichloromethane (3×50 mL). The combined organic phase washed with brine, dried over anhydrous sodium sulfate, and concentrated in vacuo. The residue was purified by column chromatography over silica gel using a mixture of dichloromethane and methanol (20:1 to 10:1) as the eluent to give a yellowish oil (which was used in the next step directly). A portion of the oil (186 mg, 1 mmol), N-hydroxysuccinimide (HOSu) (138 mg, 1.2 mmol), and N,N'-dicyclohexylcarbodiimide (DCC) (247 mg, 1.2 mmol) were added to 10 mL of anhydrous THF. After the reaction mixture was stirred at room temperature for 24 h, the precipitate was removed by filtration. The filtrate was concentrated in vacuo. The residue was purified by column chromatography over silica gel using 10:1 to 2:1 hexane/ethyl acetate as the eluent to afford a yellowish oil (180 mg, 63%). $^1$H NMR (400 MHz, CDCl$_3$) δ 3.44 (s, 4H), 3.00 (t, J=7.6 Hz, 2H) 2.87-2.82 (m, 2H), 2.61 (t, J=7.6 Hz, 2H). $^{13}$C NMR (101 MHz, cdcl$_3$) δ 170.29, 169.09, 168.08, 50.75, 39.02, 30.71, 26.89, 25.57. HRMS (ESI$^+$/QTOF) Calcd for $C_{10}H_{13}N_5O_5$ m/z: [M+H]$^+$ 284.0995; Found, 284.0986.

NH$_2$-MNP. The amino-functionalized MNP was prepared according to literature procedures. A solution of FeSO$_4$.7H$_2$O and FeCl$_3$.6H$_2$O in a 1:2 ratio was prepared in deionized water with the total iron concentration at 0.3 M.

The solution was degassed with nitrogen under ultrasonication for 30 minutes in a three-necked flask and was stirred at 70° C. under nitrogen. Aqueous ammonia solution (25% w/w) was added dropwise to the vigorously stirred solution, with the pH of the solution kept at ~9. The solution was then heated to 85° C. for 1 hour. The $Fe_3O_4$ precipitate was washed twice with anhydrous ethanol and three times with water, and then was dried in vacuo at 40° C. and stored at 4° C. in a refrigerator for subsequent use.

A solution of sodium silicate (95 mg) in deionized water (10 mL) was prepared, with its pH adjusted to 12-13 by 1 M hydrochloric acid. $Fe_3O_4$ nanoparticles (100 mg) prepared above were combined with the silicate solution. The suspension was ultrasonicated for 30 minutes and then stirred at 80° C. with a mechanical stirrer, while 0.1 M hydrochloric acid was added dropwise until the pH of the reaction mixture reached 6-7. The precipitate was washed three times with deionized water and then dispersed in 250 ml of methanol. This step was repeated twice to afford MNP with a silica shell.

MNP (100 mg) was combined with methanol (15 mL), $H_2O$ (15 mL), and glycerol (15 mL) and the mixture was ultrasonicated for 30 minutes. An 100 μL aliquot of 3-aminopropyltrimethoxysilane (APS) was added and the mixture was stirred vigorously at 90° C. for 3 hours. The resulting $NH_2$-MNP was washed with deionized water three times and ethanol twice before dried at room temperature under vacuum.

MINP(5B+7F)@MNP. Surface ligand 43 (100 μL) was added to a suspension of $NH_2$-MNP (50 mg) in DMF (5 mL). The reaction mixture was stirred at 60° C. overnight. The resulting $N_3$-MNP was washed with deionized water three times and ethanol twice before dried at room temperature under vacuum. MINP(5B+7F) was prepared by the procedures described above-except without surface decoration with ligand 3—and purified by dialysis against deionized water. A 10 mg/mL stock solution of such MINP (1.0 mL) was added to a suspension of $N_3$-MNP (10 mg) in water (2 mL), followed by addition of $CuCl_2$ (10 μL of a 10 mM solution) and sodium ascorbate (10 μL of a 50 mM solution in $H_2O$). The reaction mixture was stirred overnight. The resulting MINP(5B+7F)@MNP was washed with water and methanol with 2% acetic acid three times before dried at room temperature under vacuum.

Exemplary Embodiments

The following exemplary embodiments are provided, the numbering of which is not to be construed as designating levels of importance:

Embodiment 1 provides a molecularly-imprinted cross-linked micelle selective for a glycan, the micelle comprising: an imprint of the functional or structural analogue of a glycan; a binding unit and an acid unit, wherein the binding unit is bindable to the glycan; and the acid unit is proximal to a glycosidic bond of the glycan during binding of the glycan to the binding unit.

Embodiment 2 provides the micelle of Embodiment 1, wherein the micelle is obtained from the functional or structural analogue of a glycan as a template.

Embodiment 3 provides the micelle of Embodiment 1 or 2, wherein the functional or structural analogue of the glycan is a monosaccharide.

Embodiment 4 provides the micelle of Embodiment 1 or 2, wherein the functional or structural analogue of the glycan in an oligosaccharide.

Embodiment 5 provides the micelle of Embodiment 1 or 2, wherein the functional or structural analogue of the glycan is glucose, maltose, or maltotriose.

Embodiment 6 provides the micelle of any one of Embodiments 1-5, wherein the acid unit is covalently bound to the micelle.

Embodiment 7 provides the micelle of any one of Embodiments 1-5, wherein the acid unit is noncovalently bound to the micelle.

Embodiment 8 provides the micelle of any one of Embodiments 1-5, wherein the acid unit is bound to the micelle by metal-ligand complexation.

Embodiment 9 provides the micelle of any one of Embodiments 1-8, wherein the acid unit is a double acid.

Embodiment 10 provides the micelle of any one of Embodiments 1-9, wherein the acid unit is a Brønsted acid.

Embodiment 11 provides the micelle of any one of Embodiments 1-9, wherein the acid unit is a carboxylic acid.

Embodiment 12 provides the micelle of any one of Embodiments 1-9, wherein the acid unit is a sulfonic acid.

Embodiment 13 provides the micelle of any one of Embodiments 1-9, wherein the acid unit is a phosphonic acid.

Embodiment 14 provides the micelle of any one of Embodiments 1-9, wherein the acid unit is a Lewis acid.

Embodiment 15 provides the micelle of any one of Embodiments 1-14, wherein the micelle is obtained from cross-linkable surfactants containing one or more functional groups that are polymerizable and cross-linkable.

Embodiment 16 provides the micelle of any one of Embodiments 1-15, wherein the micelle comprises surfactants comprising one or more terminal azido, alkyne, vinyl, and/or thiol groups on the surfactant headgroup.

Embodiment 17 provides the micelle of any one of Embodiments 1-16, wherein the micelle comprises surfactants comprising one or more polymerizable vinyl groups that are polymerizable by free radical polymerization.

Embodiment 18 provides the micelle of any one of Embodiments 1-17, wherein the micelle comprises a surface and a core, and is cross-linked on the surface by covalent bonds.

Embodiment 19 provides the micelle of any one of Embodiments 1-18, wherein the micelle comprises a surface and a core, and is cross-linked in the core by covalent bonds.

Embodiment 20 provides the micelle of any one of Embodiments 1-19, wherein the binding unit comprises a boroxole.

Embodiment 21 provides the micelle of any one of Embodiments 1-19, wherein the binding unit comprises a boronic acid.

Embodiment 22 provides the micelle of any one of Embodiments 1-19, wherein the binding unit comprises a hydrogen-bonding group.

Embodiment 23 provides the micelle of any one of Embodiments 1-19, wherein the binding unit comprises an amide group.

Embodiment 24 provides a material comprising the micelle of any one of Embodiments 1-23, wherein the micelle is bonded to a solid support.

Embodiment 25 provides the material micelle of Embodiment 24, wherein the micelle is covalently or noncovalently bonded to the solid support.

Embodiment 26 provides a method of making the molecularly imprinted micelle of Embodiments 1-23, comprising:
cross-linking the surface of a micelle comprising a cross-linkable surfactant, a functional or structural analogue of a glycan, a functional monomer that binds the glycan or analogue by covalent or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit to the imprinted site by covalent bond formation, metal-ligand complexation, or non-covalent interactions.

Embodiment 27 provides a method of making the molecularly imprinted micelle of Embodiments 1-23, comprising:
cross-linking the surface of a micelle comprising a cross-linkable surfactant, a functional or structural analogue of a glycan, a functional monomer that binds the glycan or analogue by covalent or noncovalent bonds, a free radical cross-linker, and a free radical initiator;
cross-linking the surface of the micelle;
cross-linking the core of the micelle;
removing a portion or the entire functional or structural analogue of the glycan to expose a reactive group in the imprinted site; and
attaching an acid unit to the reactive group by covalent bond formation.

Embodiment 28 provides a method of making the molecularly imprinted micelle of Embodiments 1-23, comprising:
cross-linking the surface of a micelle comprising a cross-linkable surfactant, a functional or structural analogue of a glycan, a functional monomer that binds the glycan or analogue by covalent or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit by metal-ligand complexation to the imprinted site.

Embodiment 29 provides a method of making the molecularly imprinted micelle of Embodiments 1-23, comprising:
cross-linking the surface of a micelle comprising a cross-linkable surfactant, a functional or structural analogue of a glycan, a functional monomer that binds the glycan or analogue by covalent or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit by non-covalent interactions to the imprinted site.

Embodiment 30 provides a method of hydrolyzing an oligosaccharide or polysaccharide comprising contacting an oligosaccharide or polysaccharide with a micelle of any one of Embodiments 1-25.

Embodiment 31 provides the method of any one of Embodiments 26-30, wherein the oligosaccharide or polysaccharide is dissolved and/or suspended in an aqueous buffer.

Embodiment 32 provides the method of any one of Embodiments 26-30, wherein the buffer is a sodium acetate buffer.

Embodiment 33 provides the method of any one of Embodiments 26-30, wherein the oligosaccharide or polysaccharide is dissolved and/or suspended in a weak acid.

Embodiment 34 provides the method of any one of Embodiments 26-30, wherein the weak acid is $H_3PO_4$.

Embodiment 35 provides the method of any one of Embodiments 26-30, wherein the oligosaccharide or polysaccharide is dissolved and/or suspended in an ionic liquid.

Embodiment 36 provides the method of any one of Embodiments 26-30, wherein the oligosaccharide or polysaccharide is dissolved and/or suspended in a mixture of ionic liquids and organic solvent.

Embodiment 37 provides the method of any one of Embodiments 26-30, wherein the mixture comprises 1-ethyl-3-methylimidazolium acetate and DMSO.

Embodiment 38 provides the method of any one of Embodiments 26-30, wherein the oligosaccharide or polysaccharide is dissolved and/or suspended in water.

Embodiment 39 provides the method of any one of Embodiments 26-38, wherein the polysaccharide or polysaccharide is cellulose.

I claim:

1. A molecularly-imprinted cross-linked micelle selective for a glycan, the micelle comprising:
an imprint of the functional or structural analogue of a glycan;
a binding unit and an acid unit, wherein the binding unit is bindable to the glycan;
and the acid unit is proximal to a glycosidic bond of the glycan during binding of the glycan to the binding unit.

2. The micelle of claim 1, wherein the micelle is obtained from the functional or structural analogue of a glycan as a template.

3. The micelle of claim 1, wherein the functional or structural analogue of the glycan is a monosaccharide.

4. The micelle of claim 1, wherein the functional or structural analogue of the glycan is an oligosaccharide or polysaccharide.

5. The micelle of claim 1, wherein the functional or structural analogue of the glycan is glucose, maltose, or maltotriose.

6. The micelle of claim 1, wherein the acid unit is a double acid.

7. The micelle of claim 1, wherein the acid unit is a Brønsted acid.

8. The micelle of claim 7, wherein the acidic unit is a carboxylic acid, sulfonic acid, or a phosphonic acid.

9. The micelle of claim 1, wherein the acid unit is a Lewis acid.

10. The micelle of claim 1, wherein the micelle is obtained from cross-linkable surfactants containing one or more functional groups that are polymerizable and cross-linkable.

11. The micelle of claim 1, wherein the micelle comprises surfactants comprising one or more polymerizable vinyl groups that are polymerizable by free radical polymerization.

12. The micelle of claim 1, wherein the micelle comprises a surface and a core and is cross-linked on the surface by covalent bonds.

13. The micelle of claim 1, wherein the micelle is cross-linked in the core by covalent bonds.

14. The micelle of claim 1, wherein the binding unit comprises a boroxole, a boronic acid, or an amide group.

15. A material comprising the micelle of claim 1, wherein the micelle is covalently or non-covalently bonded to a solid support.

16. A method of making the molecularly imprinted micelle of claim 1 comprising:
cross-linking the surface of a micelle comprising a cross-linkable surfactant, a functional or structural analogue of a glycan, a functional monomer that binds the glycan or analogue by covalent or noncovalent bonds, a free radical cross-linker, and a free radical initiator;
cross-linking the surface of the micelle;
cross-linking the core of the micelle;
removing a portion or the entire functional or structural analogue of the glycan to create an imprinted site; and
attaching an acid unit to the imprinted site by covalent bond formation, metal-ligand complexation, or non-covalent interactions.

17. A method of hydrolyzing an oligosaccharide or polysaccharide, comprising contacting the oligosaccharide or polysaccharide with the micelle of claim 1.

18. The method of claim 17, wherein during the contacting of the oligosaccharide or polysaccharide with the micelle of claim 1, the oligosaccharide or polysaccharide is dissolved and/or suspended in an aqueous buffer, a weak acid, ionic liquids, or in a mixture of ionic liquids and organic solvent.

19. The method of claim 17, wherein during the contacting of the oligosaccharide or polysaccharide with the micelle of claim 1, the oligosaccharide or polysaccharide is dissolved and/or suspended in water.

20. The method of claim 17, wherein the oligosaccharide or polysaccharide is cellulose.

* * * * *

UNITED STATES PATENT AND TRADEMARK OFFICE
CERTIFICATE OF CORRECTION

PATENT NO. : 11,986,808 B2
APPLICATION NO. : 17/368257
DATED : May 21, 2024
INVENTOR(S) : Yan Zhao It is certified that error appears in the above-identified patent and that said Letters Patent is hereby corrected as shown below:

In the Specification

In Column 1, Line 66, delete "ρ" and insert --β-- therefor

In Column 10, Line 23, delete "D" and insert --$D_t$-- therefor

In Column 10, Line 25, delete "kB" and insert --$k_B$-- therefor

In Column 12, Line 19, delete "L" and insert --μL-- therefor

In Column 13, Line 54, delete "(FIG. 1)." and insert --(Fig. 1B).-- therefor

In Column 15, Line 43, delete "Fares," and insert --Farès,-- therefor

In Column 17, Line 14, delete "(FIG. 1)." and insert --(FIG. 1B).-- therefor

In Column 25, Line 21, delete "mMMES" and insert --mM MES-- therefor

In Column 26, Line 9, delete "10a" and insert --10α-- therefor

In Column 26, Line 11, delete "a" and insert --α-- therefor

In Column 26, Line 21, delete "a" and insert --α-- therefor

In Column 32, Line 4, delete "$^1$1H" and insert --$^1$H-- therefor

In Column 32, Line 7, delete "1H)," and insert --3H),-- therefor

In Column 32, Line 9, delete "211)," and insert --2H),-- therefor

Signed and Sealed this
Eleventh Day of February, 2025

Coke Morgan Stewart
*Acting Director of the United States Patent and Trademark Office*

CERTIFICATE OF CORRECTION (continued)
U.S. Pat. No. 11,986,808 B2

In Column 32, Line 57, delete "THE" and insert --THF-- therefor

In Column 34, Line 67, delete "ln/z:" and insert --m/z:-- therefor

In Column 35, Line 19, delete "n/z" and insert --m/z-- therefor

In Column 35, Line 24, delete "N-MR" and insert --NMR-- therefor

In Column 35, Line 26, delete "11H)," and insert --1H),-- therefor

In Column 35, Line 28, delete "411)," and insert --4H),-- therefor

In Column 35, Line 28, delete "3.31-329" and insert --3.31-3.29-- therefor

In Column 35, Line 29, delete "M-z," and insert --MHz,-- therefor

In Column 35, Line 38, delete "H" and insert --$^1$H-- therefor

In Column 35, Line 42, delete "11H)," and insert --1H),-- therefor

In Column 36, Line 5, delete "4H" and insert --$^1$H-- therefor

In Column 36, Line 13, delete "6130," and insert --61.30,-- therefor

In Column 36, Line 27, delete "HRMIS" and insert --HRMS-- therefor

In Column 36, Line 36, delete "1)," and insert --1H),-- therefor

In Column 36, Line 37, delete "11H)," and insert --1H),-- therefor

In Column 36, Line 40, delete "N-MR" and insert --NMR-- therefor

In Column 36, Line 48, delete "754.2564," and insert --754.2564;-- therefor

In Column 37, Line 17, delete "398-3.94" and insert --3.98-3.94-- therefor

In Column 37, Line 19, delete "3M)," and insert --3H),-- therefor

In Column 37, Line 58, delete "13353," and insert --133.53,-- therefor

In Column 37, Line 60, delete "6129," and insert --61.29,-- therefor

In Column 38, Line 13, delete "H);" and insert --1H);-- therefor

In Column 38, Line 15, delete "FIRMS" and insert --HRMS-- therefor

CERTIFICATE OF CORRECTION (continued)
U.S. Pat. No. 11,986,808 B2

In Column 38, Line 16, delete "16:2.0197," and insert --162.0197;-- therefor

In Column 38, Line 34, delete "3H):" and insert --3H);-- therefor

In Column 38, Line 34, delete "298 K" and insert --298 K,-- therefor

In Column 38, Line 35, delete "16211," and insert --162.11,-- therefor

In Column 38, Line 37, delete "FIRMS" and insert --HRMS-- therefor

In Column 38, Line 42, delete "ng," and insert --mg,-- therefor

In Column 38, Line 43, delete "CH$_3$OH/THF/HO" and insert --CH$_3$OH/THF/H$_2$O-- therefor In Column 38, Line 52, delete "J$_2$=28.1" and insert --J$_2$=2.8-- therefor In Column 38, Line 54, delete "(M," and insert --(m,-- therefor In Column 39, Line 7, delete "1H)." and insert --1H),-- therefor In Column 39, Line 24, delete "7.74-7.4:2" and insert --7.74-7.42-- therefor In Column 39, Line 30, delete "6492254." and insert --649.2254.-- therefor In Column 41, Line 51, delete "MINP(SA)" and insert --MINP(5A)-- therefor In the Claims In Column 46, Line 46, in Claim 1, after "glycan;", insert --and--

In Column 46, Line 47, in Claim 1, before "the", delete "and"

In Column 46, Line 63, in Claim 7, delete "Brønsted" and insert --Brønsted-- therefor In Column 47, Line 19, in Claim 16, delete "claim 1" and insert --claim 1,-- therefor